(12) United States Patent
Nebuya et al.

(10) Patent No.: US 11,457,832 B2
(45) Date of Patent: ***Oct. 4, 2022

(54) MEASUREMENT DEVICE, SHAPE ESTIMATION DEVICE, MEASUREMENT METHOD, SHAPE ESTIMATION METHOD, AND NON-TRANSITORY RECORDING MEDIUM RECORDING PROGRAM

(71) Applicant: SCHOOL JURIDICAL PERSON KITASATO INSTITUTE, Tokyo (JP)

(72) Inventors: Satoru Nebuya, Sagamihara (JP); So Hifumi, Sagamihara (JP)

(73) Assignee: SCHOOL JURIDICAL PERSON KITASATO INSTITUTE, Tokyo (JP)

( * ) Notice: Subject to any disclaimer, the term of this patent is extended or adjusted under 35 U.S.C. 154(b) by 837 days.

This patent is subject to a terminal disclaimer.

(21) Appl. No.: 16/372,720

(22) Filed: Apr. 2, 2019

(65) Prior Publication Data

US 2019/0298218 A1    Oct. 3, 2019

Related U.S. Application Data

(63) Continuation-in-part of application No. 14/901,445, filed as application No. PCT/JP2014/067590 on Jul. 1, 2014, now Pat. No. 10,285,618.

(30) Foreign Application Priority Data

Jul. 2, 2013    (JP) ................ 2013-139164

(51) Int. Cl.
*A61B 5/0536* (2021.01)
*A61B 5/00* (2006.01)

(52) U.S. Cl.
CPC ........... *A61B 5/0536* (2013.01); *A61B 5/683* (2013.01); *A61B 5/6823* (2013.01); *A61B 2562/0261* (2013.01)

(58) Field of Classification Search
CPC ..... A61B 5/0536; A61B 5/6823; A61B 5/683; A61B 2562/0261; A61B 5/1128; A61B 5/107
See application file for complete search history.

(56) References Cited

U.S. PATENT DOCUMENTS 6,279,579 B1 *    8/2001    Riaziat ................ A61N 5/1049
                                                                128/897
6,519,862 B1 *    2/2003    Owsley ................ A61B 5/1126
                                                                33/511

(Continued)

FOREIGN PATENT DOCUMENTS

CN    101524273    9/2009
JP    2017-123921    7/2017

(Continued)

OTHER PUBLICATIONS

Extended European Search Report issued in Appln. No. 14820626.1 dated Jul. 14, 2017.

(Continued)

*Primary Examiner* — Rene T Towa
(74) *Attorney, Agent, or Firm* — Nixon & Vanderhye P.C.

(57) ABSTRACT

A measurement device has a measurement belt to which a plurality of electrode pads arranged in a row and a plurality of strain gauges arranged in parallel to the plurality of electrode pads are integrally adhered and configured to be used after being wrapped around a portion serving as a measurement target of a living body; and a processor configured to: acquire an image of the portion serving as the measurement target while applying a current to the plurality of electrode pads and acquiring a voltage signal generated between the electrode pads; and estimate a contour shape of the portion serving as the measurement target and a size of (Continued)

the contour shape on the basis of curvature data acquired via the plurality of strain gauges.

19 Claims, 50 Drawing Sheets

(56) References Cited

U.S. PATENT DOCUMENTS

| | | |
|---|---|---|
| 2005/0059903 A1 | 3/2005 | Izumi |
| 2009/0084674 A1 | 4/2009 | Holzhacker et al. |
| 2010/0198101 A1 | 8/2010 | Song et al. |
| 2011/0007937 A1 | 1/2011 | Yan et al. |
| 2012/0271193 A1* | 10/2012 | Li ........................ A61B 5/0536 600/547 |
| 2013/0190577 A1* | 7/2013 | Brunner ............... A61B 5/0205 600/301 |
| 2016/0302690 A1 | 10/2016 | Nebuya et al. |

FOREIGN PATENT DOCUMENTS

| | | |
|---|---|---|
| JP | 2017-125718 | 7/2017 |
| WO | WO 2007/070997 | 6/2007 |

OTHER PUBLICATIONS

International Search Report issued in PCT/JP2014/067590 dated Sep. 16, 2014 (w/ translation).
Office Action issued in U.S. Appl. No. 14/901,445 dated Jun. 22, 2018.
Supplementary European Search Report issued in App. No. 14820626.1 dated Feb. 13, 2017.

* cited by examiner

MEASUREMENT DEVICE, SHAPE ESTIMATION DEVICE, MEASUREMENT METHOD, SHAPE ESTIMATION METHOD, AND NON-TRANSITORY RECORDING MEDIUM RECORDING PROGRAM

CROSS REFERENCE TO RELATED APPLICATIONS

This U.S. patent application is a Continuation-In-Part application of U.S. non-provisional application Ser. No. 14/901,445, filed on Feb. 8, 2016, which is a National Stage Entry of PCT International Application NO. PCT/JP2014/067590, filed on Jul. 1, 2014. Priority is claimed on Japanese Patent Application No. 2013-139164, filed on Jul. 2, 2013, Japanese Patent Application No. 2016-3892, filed on Jan. 12, 2016, and Japanese Patent Application No. 2016-3764, filed on Jan. 12, 2016, the contents of each of which are incorporated herein by reference.

TECHNICAL FIELD

The present invention relates to an electrical impedance tomography (EIT) measurement device, a measurement device, a shape estimation device, a method for acquiring a shape of a cross-section, a method of estimating a contour shape, and a non-transitory recording medium for recording program for measuring a living body.

BACKGROUND ART

An electrical impedance tomography (hereinafter simply referred to as EIT) measurement device is technology for causing a weak current to flow from pairs of electrodes adhered to a body surface and imaging a conductivity distribution or a distribution of a conductivity change within a living body from a potential difference occurring in the body surface.

EIT has an advantage in that size reduction, long-time measurement, and real-time measurement are facilitated without a problem of radiation exposure as compared with X-ray computed tomography (CT) because it is possible to acquire a tomographic image by applying only a weak current.

In EIT measurement, in general, 8 to 64 electrodes are used. These electrodes are adhered to the periphery of a measurement target portion and connected to a measurement circuit by routing signal cables individually connected to the electrodes. Recently, methods of unifying a plurality of electrodes and signal cables as a module and facilitating the attachment and detachment of the electrodes and the setting of a measurement device have been attempted.

Further, in such methods, technology for connecting a large number of electrode cables used in EIT to electrodes by performing modularization for every two or more pieces or technology for modularizing electrodes for every two or more pieces to simplify a procedure of connecting a required large number of electrodes to a body surface during EIT measurement are proposed (for example, see Patent Literatures 1 and 2).

Recently, a technology for solving various problems using wearable devices incorporated into clothing or worn on the body as implants or accessories is required. For example, it is considerable to utilize the wearable devices to estimate a shape of the living body or other objects. In Patent Literature 3, a technology using a measurement belt with strain gauges to estimate the contour shape of the living body and measure the perimeter according to the estimated contour shape is disclosed.

CITATION LIST

Patent Literatures

[Patent Literature 1]
  Japanese Unexamined Patent Application, First Publication No. 2012-228514
[Patent Literature 2]
  Japanese Unexamined Patent Application, First Publication No. 2009-523037
[Patent Literature 3]
  PCT International Publication No. WO 2015/002210

SUMMARY OF INVENTION

Technical Problem

However, in the above-described EIT measurement, information indicating a positional relation in which a plurality of electrode pads are arranged is not included in a tomographic image generated on the basis of electrical signals acquired through the plurality of electrode pads. That is, the tomographic image generated by the EIT measurement device is generated by virtualizing a relative positional relation between the electrode pads, and an absolute positional relation between coordinate positions in the tomographic image and positions in an actual tomographic image in a measurement target is not specified.

In this case, it is not possible for an operator (a person who performs medical treatment) of the EIT measurement device to accurately diagnose various measurement targets having a different shape or size of a contour on the basis of a generated tomographic image.

On the other hand, even if the operator of the EIT measurement device performs an operation of finding a shape of a measurement target portion by performing an operation of measuring a ratio (referred to as an e value) of a vertical length of the measurement target portion to a horizontal length using a dedicated caliper or the like, there is a possibility not only of labor becoming complicated, but also of a measurement error increasing. In addition, in this technique, it is difficult to handle a patient who cannot easily stand.

The present invention provides an EIT measurement device, an EIT measurement method, and a program capable of performing simple and more accurate diagnosis even for various measurement targets having a different shape or size of a contour.

Solution to Problem

According to a first aspect of the present invention, there is provided a measurement device including: a measurement belt to which a plurality of electrode pads arranged in a row and a plurality of strain gauges arranged in parallel to the plurality of electrode pads are integrally adhered and configured to be used after being wrapped around a portion serving as a measurement target of a living body; and a processor configured to: acquire an image of the portion serving as the measurement target while applying a current to the plurality of electrode pads and acquiring a voltage signal generated between the electrode pads; and estimate a contour shape of the portion serving as the measurement target and a size of the contour shape on the basis of curvature data acquired via the plurality of strain gauges, wherein the processor is further configured to: set coordinate positions of a first reference point and a second reference point as predetermined initial coordinate values, the coordinate position of the first reference points indicating a position of the strain gauge among the plurality of strain gauges arranged in the row at a first half side of the portion serving as the measurement target of the living body and the coordinate position of the second reference point indicating a position of a virtual strain gauge defined to be disposed between adjacent strain gauges among the plurality of strain gauges arranged in the row at a second half side opposite to the first half side of the portion serving as the measurement of the living body; calculate relative coordinate values indicating coordinate positions of subordinate potions according to the curvature data, the coordinate positions of the subordinate points indicating positions of one or more strain gauges with respect to the coordinate positions of adjacent first reference point and adjacent second reference point, and the one or more strain gauges being disposed between the strain gauges indicated by the adjacent first reference point and adjacent second reference point; change coordinate positions of the first reference point different from the first reference point and the second reference point such that coordinate positions between a first subordinate point and a second subordinate point become closest, the first subordinate point being the subordinate point whose coordinate position is determined from the relative coordinate value with respect to the coordinate position of the first reference point, the second subordinate point being the subordinate point whose coordinate position is determined from the relative coordinate value with respect to the coordinate position of the second reference point, and the first and second subordinate points indicating the position of the same strain gauge; determine the coordinate positions of two subordinate points indicating positions of strain gauges disposed adjacently at both sides of each strain gauge indicated by each reference point as the coordinate position of a center point between the first subordinate point and the second subordinate point after the coordinate positions of the first reference point and the second reference point are changed; and estimate a contour shape based on the relative positional relation of the positions of the first and second reference and subordinate points using a predetermined function curve.

According to a second aspect of the present invention, in the measurement device according to the first aspect, the processor may be configured to enlarge or reduce the specified contour shape such that a perimeter of the estimated contour shape matches a separately measured perimeter of the portion serving as the measurement target after the contour shape is determined.

According to a third aspect of the present invention, in the measurement device according to the first aspect, the processor may be configured to regard the virtual strain gauge as being arranged on the symmetric axis of the portion serving as the measurement target to determine a relative positional relationship for the plurality of strain gauges, when no strain gauge is arranged at a position arranged at the opposite side of the strain gauge whose coordinate position is determined by the first reference point on the true symmetric axis of the portion serving as the measurement target on the measurement belt wrapped around the portion serving as the measurement target.

According to a fourth aspect of the present invention, in the measurement device according to the first aspect, the processor may be configured to set a plurality of supplementary points for determining a curve connecting a position of one strain gauge and a position of another strain gauge adjacent to the one strain gauge when the contour shape is determined, and a distance from an origin of the plurality of supplementary points may be determined by a predetermine function at an angle formed by the supplementary points, the origin, and the position of the one strain gauge.

According to a fifth aspect of the present invention, the measurement device according to the first aspect may further include a perimeter measurement electrode pad arranged in parallel to the plurality of electrode pads and adhered to the measurement belt; and a perimeter measurement unit configured to measure a perimeter of the portion serving as the measurement target on the basis of a voltage signal acquired via the perimeter measurement electrode pad.

According to a sixth aspect of the present invention, there is provided a measurement method including: winding a measurement belt to which a plurality of electrode pads arranged in a row and a plurality of strain gauges arranged in parallel to the plurality of electrode pads are integrally adhered around a portion serving as a measurement target of a living body; acquiring an image of the portion serving as the measurement target while applying a current to the plurality of electrode pads and acquiring a voltage signal generated between the electrode pads; determining a relative positional relation for every strain gauge; and estimating a contour shape of the portion serving as the measurement target and a size of the contour shape on the basis of curvature data acquired via the plurality of strain gauges, wherein the determining method further includes: setting coordinate positions of a first reference point and a second reference point as predetermined initial coordinate values, the coordinate position of the first reference points indicating a position of the strain gauge among the plurality of strain gauges arranged in the row at a first half side of the portion serving as the measurement target of the living body and the coordinate position of the second reference point indicating a position of a virtual strain gauge defined to be disposed between adjacent strain gauges among the plurality of strain gauges arranged in the row at a second half side opposite to the first half side of the portion serving as the measurement of the living body; calculating relative coordinate values indicating coordinate positions of subordinate potions according to the curvature data, the coordinate positions of the subordinate points indicating positions of one or more strain gauges with respect to the coordinate positions of adjacent first reference point and adjacent second reference point, and the one or more strain gauges being disposed between the strain gauges indicated by the adjacent first reference point and adjacent second reference point; changing coordinate positions of the first reference point different from the first reference point and the second reference point such that coordinate positions between a first subordinate point and a second subordinate point become closest, the first subordinate point being the subordinate point whose coordinate position is determined from the relative coordinate value with respect to the coordinate position of the first reference point, the second subordinate point being the subordinate point whose coordinate position is determined from the relative coordinate value with respect to the coordinate position of the second reference point, and the first and second subordinate points indicating the position of the same strain gauge; determining the coordinate positions of two subordinate points indicating positions of strain gauges disposed adjacently at both sides of each strain gauge indicated by each reference point as the coordinate position of a center point between the first subordinate point and the second subordinate point after the coordinate positions of the first reference point and the second reference point are changed, and estimating a contour shape based on the relative positional relation of the positions of the first and second reference and subordinate points using a predetermined function curve.

According to a seventh aspect of the present invention, a non-transitory storage medium storing a program for causing a computer of a measurement device, which includes a measurement belt to which a plurality of electrode pads arranged in a row and a plurality of strain gauges arranged in parallel to the plurality of electrode pads are integrally adhered and configured to be used after being wrapped around a portion serving as a measurement target of a living body to: acquire an image of the portion serving as the measurement target while applying a current to the plurality of electrode pads and acquiring a voltage signal generated between the electrode pads; determine a relative positional relation for every strain gauge; and estimate a contour shape of the portion serving as the measurement target and a size of the contour shape on the basis of curvature data acquired via the plurality of strain gauges, wherein the program further causes the processor to: set coordinate positions of a first reference point and a second reference point as predetermined initial coordinate values, the coordinate position of the first reference points indicating a position of the strain gauge among the plurality of strain gauges arranged in the row at a first half side of the portion serving as the measurement target of the living body and the coordinate position of the second reference point indicating a position of a virtual strain gauge defined to be disposed between adjacent strain gauges among the plurality of strain gauges arranged in the row at a second half side opposite to the first half side of the portion serving as the measurement of the living body; calculate relative coordinate values indicating coordinate positions of subordinate potions according to the curvature data, the coordinate positions of the subordinate points indicating positions of one or more strain gauges with respect to the coordinate positions of adjacent first reference point and adjacent second reference point, and the one or more strain gauges being disposed between the strain gauges indicated by the adjacent first reference point and adjacent second reference point; change coordinate positions of the first reference point different from the first reference point and the second reference point such that coordinate positions between a first subordinate point and a second subordinate point become closest, the first subordinate point being the subordinate point whose coordinate position is determined from the relative coordinate value with respect to the coordinate position of the first reference point, the second subordinate point being the subordinate point whose coordinate position is determined from the relative coordinate value with respect to the coordinate position of the second reference point, and the first and second subordinate points indicating the position of the same strain gauge; determine the coordinate positions of two subordinate points indicating positions of strain gauges disposed adjacently at both sides of each strain gauge indicated by each reference point as the coordinate position of a center point between the first subordinate point and the second subordinate point after the coordinate positions of the first reference point and the second reference point are changed, and estimate a contour shape based on the relative positional relation of the positions of the first and second reference and subordinate points using a predetermined function curve.

According to an eighth aspect of the present invention, there is provided a measurement device including: a measurement belt having a plurality of first electrodes arranged on a longitudinal direction of the measurement belt, a second electrode, and a plurality of curvature sensors arranged on a longitudinal direction of the measurement belt, the measurement belt being configured to be wrapped around a portion serving as a measurement target of a living body; and a processor configured to: detect predetermined physical effect applied to the measurement belt; determine whether there is one of the first electrode among the plurality of first electrodes whose impedance with respect to the second electrode is equal to or lower than a predetermined impedance value; and estimate a contour shape of the portion serving as the measurement target and a size of the contour shape on the basis of curvature data acquired via the plurality of curvature sensors, when the predetermined physical effect is detected and the first electrode among the plurality of first electrodes whose impedance with respect to the second electrode is equal to or lower than the predetermined impedance value is confirmed, wherein the processor is further configured to: set coordinate positions of a plurality of reference points as predetermined initial coordinate values, each of the coordinate positions of the plurality of reference points indicating a position of one curvature sensor among the plurality of curvature sensors arranged in the row; calculate relative coordinate values indicating coordinate positions of subordinate points according to the curvature data, the coordinate positions of the subordinate points indicating positions of one or more curvature sensors with respect to the coordinate positions of adjacent reference points of the plurality of reference points, and the one or more curvature sensors being disposed between the curvature sensors indicated by the adjacent reference points of the plurality of reference points, change coordinate positions of a first reference point and a second reference point different from the first reference point among the plurality of reference points such that coordinate positions between a first subordinate point and a second subordinate point becomes closest, the first subordinate point being the subordinate point whose coordinate position is determined from the relative coordinate value with respect to the coordinate position of the first reference point, the second subordinate point being the subordinate point whose coordinate position is determined from the relative coordinate value with respect to the coordinate position of the second reference point, and the first and second subordinate points indicating the position of the same curvature sensor, determine the coordinate positions of two subordinate points indicating positions of curvature sensors disposed adjacently at both sides of each curvature sensor indicated by each reference point as the coordinate position of a center point between the first subordinate point and the second subordinate point after the coordinate positions of the first reference point and the second reference point are changed; and estimate a contour shape based on the relative positional relation of the positions of the reference and subordinate points using a predetermined function curve.

According to a ninth aspect of the present invention, in the measurement device according to the eighth aspect, the processor may be configured to detect a movement of the belt.

According to a tenth aspect of the present invention, in the measurement device according to the eighth aspect, the processor may be configured to detect a pressure force applied on a predetermined part of the belt.

According to an eleventh aspect of the present invention, the measurement device according to the eighth aspect may further include a perimeter measurement unit configured to measure a perimeter of the portion serving as the measurement target according to the impedance between the first electrode among the plurality of first electrodes and the second electrode.

According to a twelfth aspect of the present invention, in the measurement device according to the eleventh aspect, the perimeter measurement unit may be configured to measure the perimeter of the portion serving as the measurement target, when the predetermined physical effect is detected and the first electrode among the plurality of first electrodes whose impedance with respect to the second electrode is equal to or lower than the predetermined impedance value is confirmed.

According to a thirteenth aspect of the present invention, in the measurement device according to the eleventh aspect, the processor may be further configured to: estimate a partial shape of part of the circumference of the portion serving as the measurement target according to the curvature data acquired by the plurality of curvature sensors; determine the part of the circumference of the portion serving as the measurement target corresponding to the estimated partial shape according to the perimeter; and estimate a contour shape of the whole circumference of the portion serving as the measurement target using the partial shape according to the determination result indicating the part of the circumference of the portion serving as the measurement target corresponding to the estimated partial shape and an assumption that the contour shape is axial symmetry.

According to a fourteenth aspect of the present invention, in the measurement device according to the eighth aspect, the measurement belt may have a buckle having a needle and a plurality of holes through which the needle can be penetrated, the plurality of first electrodes may be disposed at positions around the plurality of holes respectively, and the second electrode may be disposed on the needle.

According to a fifteenth aspect of the present invention, the measurement device according to the eighth aspect may further include: a first shield disposed at a first side of the plurality of first electrodes with respect to the measurement belt on either of a front surface or a rear surface of the measurement belt; and a second shield disposed at a second side of the second electrode opposite to the first side with respect to the measurement belt, wherein the first shield and the second shield are configured to restrict a flow of an electromagnetic wave.

According to a sixteenth aspect of the present invention, the measurement device according to the fifteenth aspect may further include a voltage application unit configured to apply AC voltages with a same phase to at least one of the plurality of first electrodes and the first shield, and apply AC voltage with a same phase to the second electrode and the second shield.

According to a seventeenth aspect of the present invention, there is provided a measurement device including: a sheet having a base member on which a plurality of curvature sensors are disposed, the plurality of curvature sensors being spaced from each other at a predetermined space, and the sheet being configured to be covered on a measurement target; and a processor configured to: acquire curvature information of the plurality of curvature sensors; and estimate a shape of the base member according to the curvature information, wherein the processor is further configured to: set coordinate positions of a plurality of reference points as predetermined initial coordinate values, each of the coordinate positions of the plurality of reference points indicating a position of one curvature sensor among the plurality of curvature sensors arranged on the sheet; calculate relative coordinate values indicating coordinate positions of subordinate points according to the curvature data, the coordinate positions of the subordinate points indicating positions of one or more curvature sensors with respect to the coordinate positions of adjacent reference points of the plurality of reference points, and the one or more curvature sensors being disposed between the curvature sensors indicated by the adjacent reference points of the plurality of reference points, change coordinate positions of a first reference point and a second reference point different from the first reference point among the plurality of reference points such that coordinate positions between a first subordinate point and a second subordinate point becomes closest, the first subordinate point being the subordinate point whose coordinate position is determined from the relative coordinate value with respect to the coordinate position of the first reference point, the second subordinate point being the subordinate point whose coordinate position is determined from the relative coordinate value with respect to the coordinate position of the second reference point, and the first and second subordinate points indicating the position of the same curvature sensor, determine the coordinate positions of two subordinate points indicating positions of curvature sensors disposed adjacently at both sides of each curvature sensor indicated by each reference point as the coordinate position of a center point between the first subordinate point and the second subordinate point after the coordinate positions of the first reference point and the second reference point are changed; and estimate a contour shape based on the relative positional relation of the positions of the reference and subordinate points using a predetermined function curve.

According to an eighteenth aspect of the present invention, in the measurement device according to the seventeenth aspect, the processor may be configured to estimate a shape of the measurement target covered by the sheet according to the estimated shape of the sheet.

According to a nineteenth aspect of the present invention, in the measurement device according to the seventeenth aspect, the processor may be configured to estimate a shape of clothes manufactured by the sheet according to the curvature information of the plurality of curvature sensors; and estimate a movement of the measurement target wearing the clothes according to the shape of the clothes.

According to a twentieth aspect of the present invention, in the measurement device according to the seventeenth aspect, the sheet may be formed by a plurality of electroconductive yarns.

According to a twenty-first aspect of the present invention, in the measurement device according to the twentieth aspect, the plurality of electroconductive yarns may be configured to be insulate from each other, and the plurality of curvature sensors may be disposed at the intersection points of the plurality of electroconductive yarns respectively.

Advantageous Effects of Invention

It is possible to perform simple and more accurate diagnosis even for various measurement targets having a different shape or size of a contour.

DESCRIPTION OF EMBODIMENTS

First Embodiment

Hereinafter, an EIT measurement device according to the first embodiment will be described with reference to the drawings.

Figure 1:
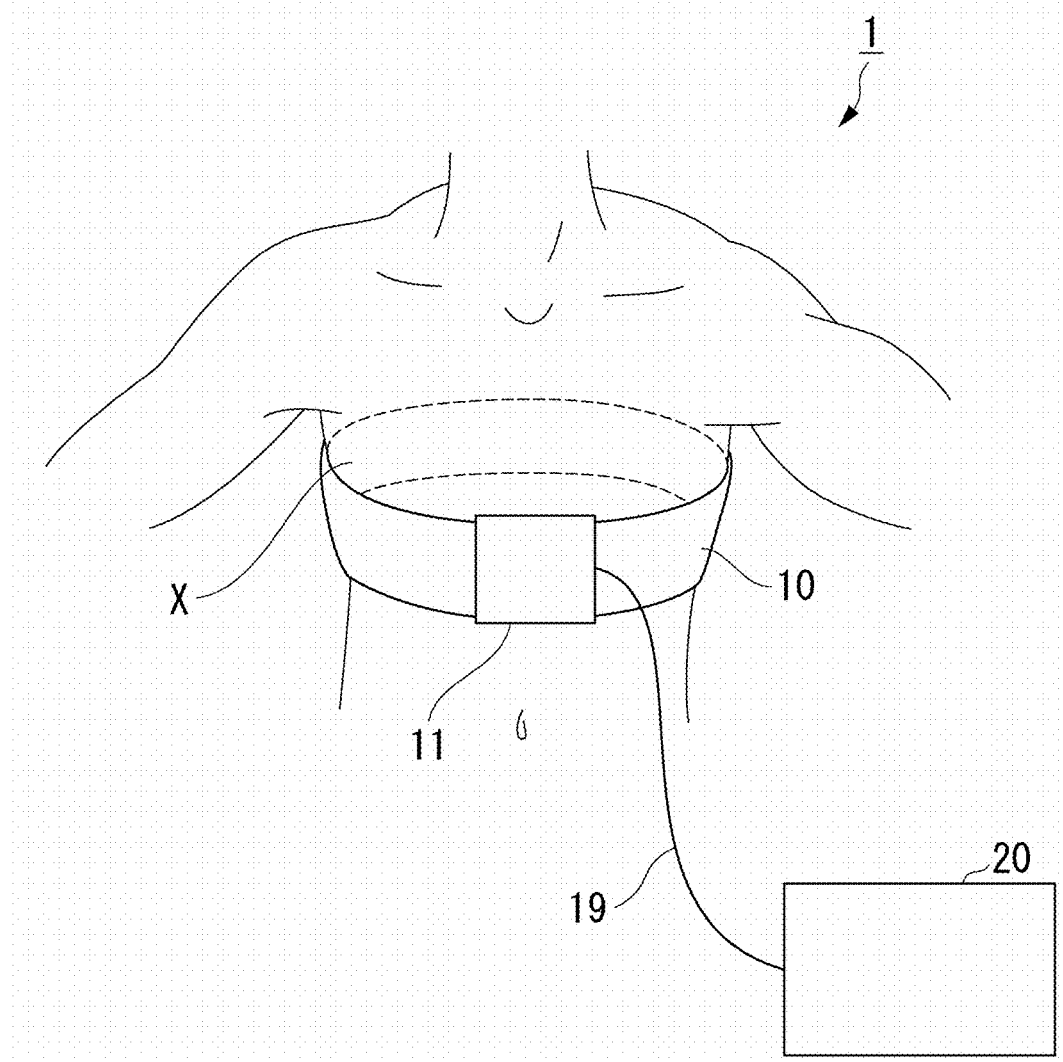
FIG. 1 is a diagram illustrating an entire configuration of an EIT measurement device according to a first embodiment.

FIG. 1 is a diagram illustrating an entire configuration of the EIT measurement device according to the first embodiment. In FIG. 1, the EIT measurement device 1 is illustrated.

The EIT measurement device 1 includes a measurement belt 10 and an EIT measurement main body unit 20. As illustrated in FIG. 1, the measurement belt 10, for example, is wrapped around a portion (hereinafter referred to as a measurement target portion X) serving as a measurement target such as a chest portion of a measurement target person (living body) and used. The measurement belt 10 is connected to the EIT measurement main body unit 20 via a measurement circuit 11 and a signal cable 19.

The measurement belt 10 may be configured with an adjustable wrapping length to be used after being wrapped around a head portion, an arm, a leg, or the like in addition to the chest portion. The measurement belt 10 is configured such that electrode pads for performing EIT measurement, etc. are provided on the same flexible substrate and the electrode pads, etc. can be integrally handled as will be described below (for example, see Japanese Patent Application No. 2010-205988).

The EIT measurement main body unit 20 is a functional unit for performing a predetermined calculation process based on an electrical signal acquired via the measurement belt 10 and the measurement circuit 11 and displaying a tomographic image of a portion (measurement target portion X) of a measurement target person around which the measurement belt 10 is wrapped. An operator of the EIT measurement device 1 can set a condition or the like for EIT measurement via a manipulation input unit provided in the EIT measurement main body unit 20 or recognize a tomographic image via a monitor (image display unit) provided in the EIT measurement main body unit 20. A detailed functional configuration of the EIT measurement main body unit 20 will be described below.

Figure 2:
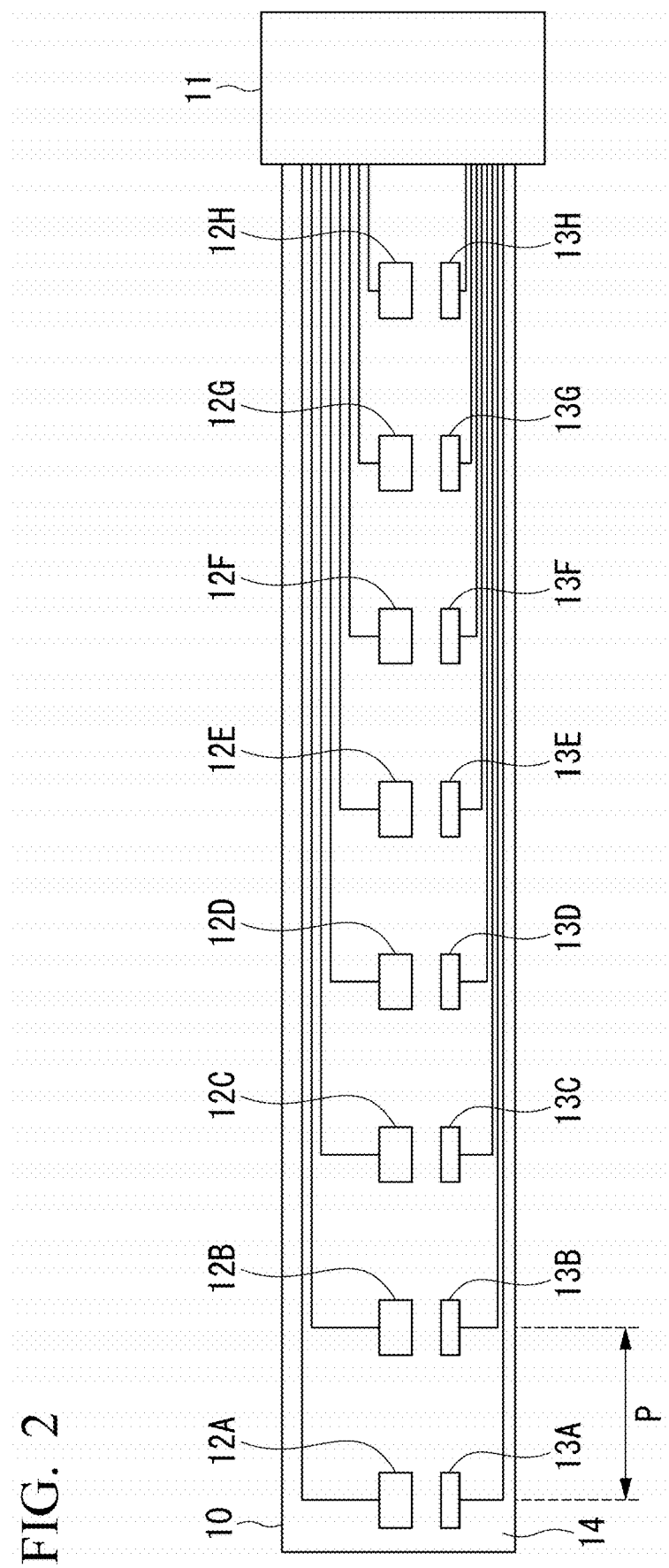
FIG. 2 is a diagram illustrating a functional configuration of a measurement belt according to the first embodiment.

FIG. 2 is a diagram illustrating a functional configuration of the measurement belt according to the first embodiment.

As illustrated in FIG. 2, the measurement belt 10 has a configuration in which eight electrode pads 12A to 12H are disposed (periodically arranged) in a row at distances P of regular intervals on a belt-shaped flexible substrate 14. Also, eight strain gauges 13A to 13H are periodically arranged at distances P of regular intervals in parallel to the eight electrode pads 12A to 12H on the same flexible substrate 14.

The measurement belt 10 is used after being wrapped around the measurement target unit X of the measurement target person while the plurality of electrode pads 12A to 12H and the strain gauges 13A to 13H are integrally adhered. When the measurement belt 10 is wrapped, the electrode pads 12A to 12H have a mechanism in contact with a body surface around the periphery of the measurement target portion X.

Through this configuration, it is possible to significantly reduce the time and effort spent attaching the electrode pads and improve operation efficiency of EIT measurement because the operator of the EIT measurement device 1 can start measurement by merely performing an operation of attaching the measurement belt 10 by wrapping the measurement belt 10 around the measurement target portion X.

Also, the measurement belt 10 may be formed with the flexible substrate 14 further covered with non-conductive belt-like fabric to reduce a burden on the measurement target person during measurement.

In addition, in this case, in the measurement belt 10, a portion in contact with the electrode pads 12A to 12H in the above-described fabric belt is constituted of a conductive gel or a conductive fiber electrode, and the measurement device 1 may perform EIT measurement via the conductive gel or the conductive fiber electrode between the electrode pads 12A to 12H and the body surface. Accordingly, the components of the measurement belt 10 can be configured so that only the fabric portion can be extracted to be washed or disposed of and the usability in terms of hygiene can be further improved.

In addition, the measurement belt 10 may have a strain gauge of the same characteristic at the same position of a backside of each of the strain gauges 13A to 13H. It is possible to implement temperature correction automation, high sensitivity, and high accuracy of the strain gauges 13A to 13H using a two-active-gauge method of connecting a pair of strain gauges of each measurement position to one bridge circuit.

Alternatively, the measurement belt 10 may have the temperature sensor at the same position of the backside of each of the strain gauges 13A to 13H. The measurement device 1 may perform temperature correction of curvature data on the basis of temperature data acquired by the temperature sensor in terms of curvature data acquired by the strain gauges 13A to 13H. Accordingly, it is possible to implement high sensitivity and high accuracy of the strain gauges 13A to 13H.

Also, the measurement circuit 11 is an electrical circuit configured to mediate the exchange of an electrical signal with the EIT measurement main body unit 20, the electrode pads 12A to 12H, and the strain gauges 13A to 13H. For example, in the measurement circuit 11, a circuit configured to amplify the electrical signal output in the strain gauges 13A to 13H or perform analog/digital (A/D) conversion on the electrical signal is provided.

Figure 3:
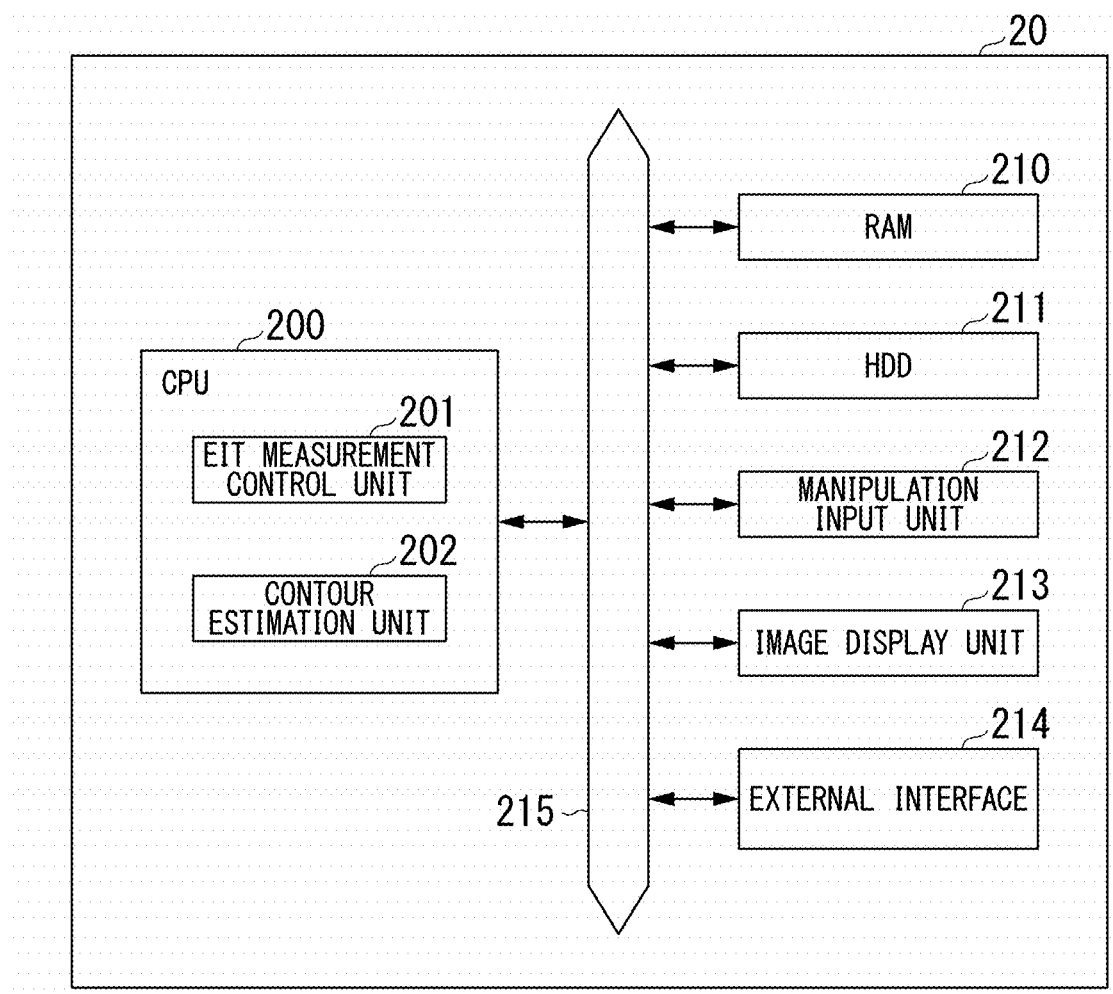
FIG. 3 is a diagram illustrating a functional configuration of an EIT measurement main body according to the first embodiment.

FIG. 3 is a diagram illustrating a functional configuration of an EIT measurement main body according to the first embodiment.

The EIT measurement main body unit 20 according to this embodiment is constituted of a general-purpose personal computer (PC) or a general peripheral device (PC monitor or the like).

As illustrated in FIG. 3, the EIT measurement main body unit 20 includes a central processing unit (CPU) 200 responsible for overall operation, a random access memory (RAM) 210 serving as a work area of the CPU 200 when a measurement program or the like for use in EIT measurement is executed, and a hard disk drive (HDD) 211 serving as a storage means configured to store various programs and a tomographic image, etc. acquired by the EIT measurement control unit 201.

Also, a manipulation input unit 212, for example, is constituted of a mouse, a keyboard, a touch panel, etc. and receives inputs of various types of manipulations by the operator. The image display unit 213 is a liquid crystal display or the like, and displays necessary information during EIT measurement, an acquired tomographic image, etc.

An external interface 214 is a communication interface for performing communication with the external device. In particular, in this embodiment, the external interface 214 is a functional unit connected to the measurement belt 10 via a dedicated communication cable and acquires various signals from the measurement belt 10.

The CPU 200, the RAM 210, the HDD 211, the manipulation input unit 212, the image display unit 213, and the external interface 214 are mutually electrically connected via a system bus 215.

As illustrated in FIG. 3, the CPU 200 performs functions as the EIT measurement control unit 201 and the contour estimation unit 202 while a predetermined measurement program is executed.

The EIT measurement control unit 201 acquires a tomographic image of a measurement target portion X while applying a current to the plurality of electrode pads 12A to 12H and acquiring voltage signals generated between the electrode pads 12A to 12H.

In addition, the contour estimation unit 202 estimates a contour shape of the measurement target portion X and a size of the contour shape on the basis of the curvature data acquired via the strain gauges 13A to 13H.

Figure 4:
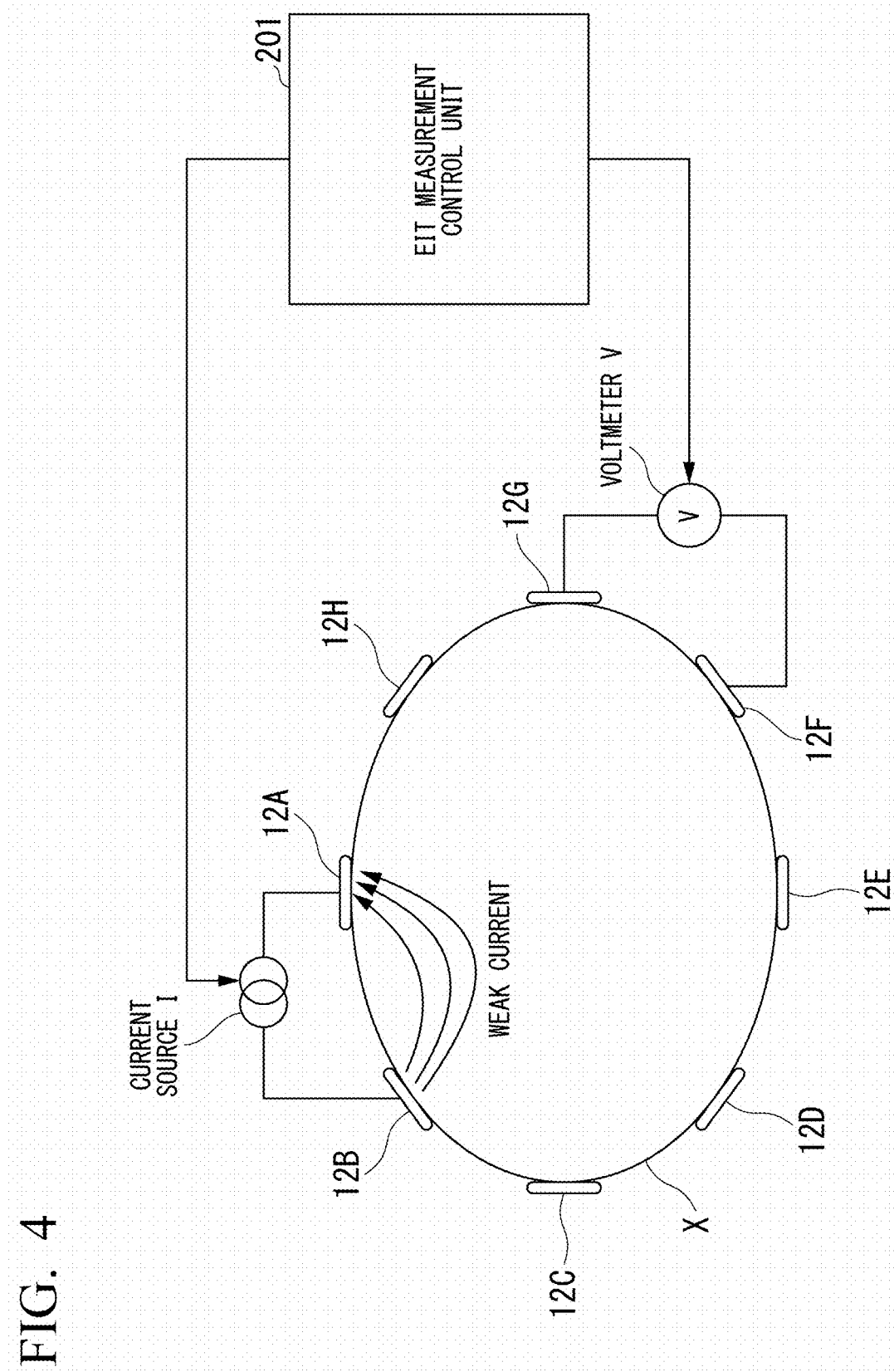
FIG. 4 is a first diagram illustrating a function of an EIT measurement control unit according to the first embodiment.

FIG. 4 is a first diagram illustrating a function of an EIT measurement control unit according to the first embodiment.

Figure 5:
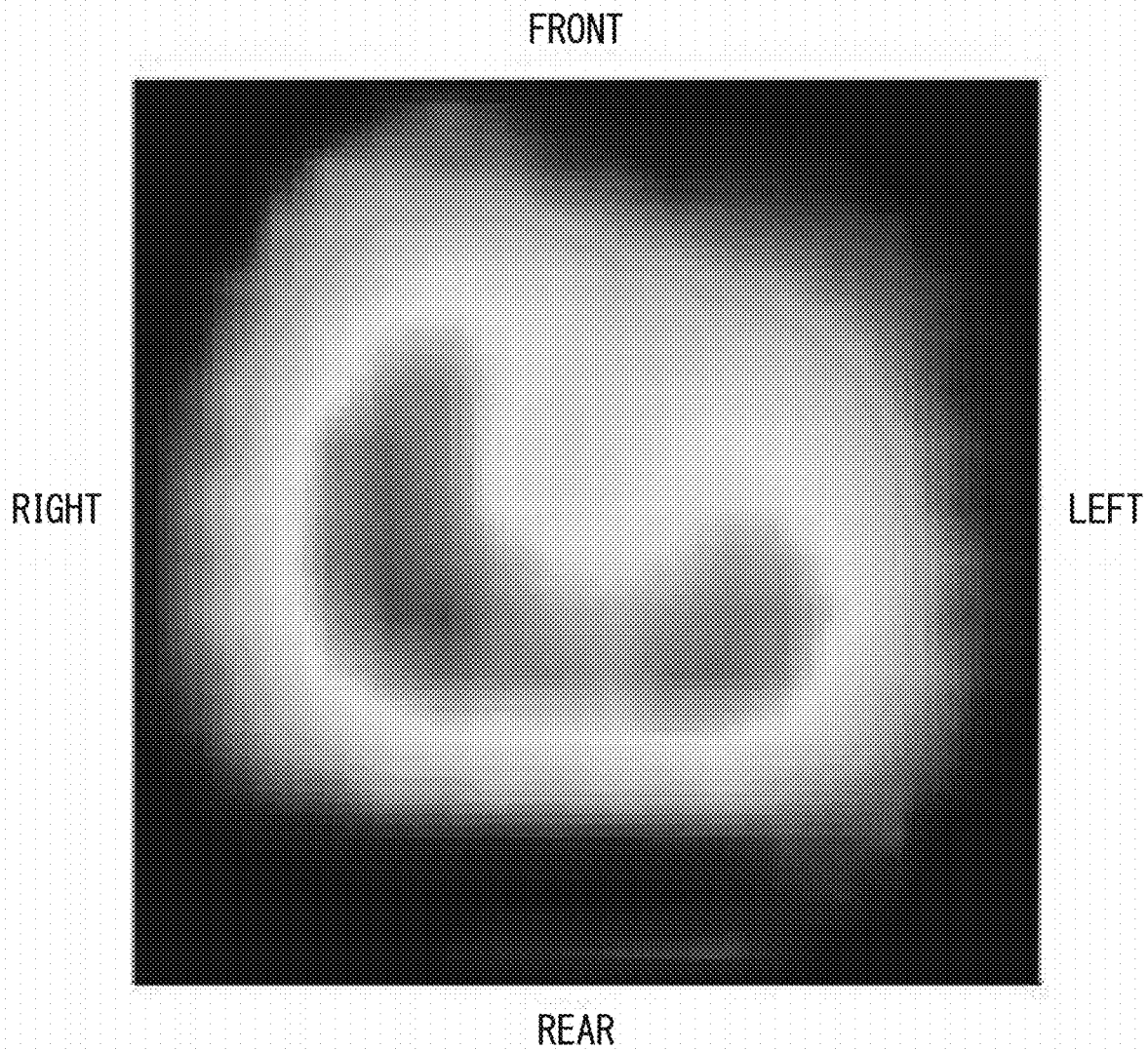
FIG. 5 is a second diagram illustrating a function of the EIT measurement control unit according to the first embodiment.

Also, FIG. 5 is a second diagram illustrating a function of the EIT measurement control unit according to the first embodiment.

Hereinafter, the function of the EIT measurement control unit 201 will be described with reference to FIGS. 4 and 5. FIG. 4 illustrates, for example, a state in which the measurement belt 10 is wrapped around the chest of the measurement target person and the electrode pads 12A to 12H are in contact with the body surface as an example of the measurement target portion X. As illustrated in FIG. 4, a configuration in which a current source I and a voltmeter V are connected between the electrode pads 12A to 12H is formed and the EIT measurement control unit 201 has a function of controlling the current source I and the voltmeter V.

The EIT measurement control unit 201 controls a predetermined weak current to flow between a pair of electrode pads (for example, between the electrode pads 12A and 12B) among the electrode pads 12A to 12H via the current source I. The EIT measurement control unit 201 measures potential differences occurring between the other electrode pads (electrode pads 12C to 12H) via the voltmeter V while the weak current flows through the pair of electrode pads. It is possible to acquire a resistivity distribution in a fault of the measurement target portion X by sequentially changing and rotating the electrode pads through which the current flows to the electrode pads 12B and 12C, 12C and 12D, . . . .

The EIT measurement control unit 201, for example, generates a tomographic image using a general reverse projection method on the basis of a resistivity distribution in a fault plane serving as a measurement target acquired as described above. The EIT measurement control unit 201 allows the operator to view a tomographic image by displaying the generated tomographic image on the image display unit 213. Also, well-known technology may be used as a technique of generating the tomographic image in the EIT measurement control unit 201.

FIG. 5 illustrates an example of the tomographic image generated by the EIT measurement control unit 201. FIG. 5 is a tomographic image in a chest portion of the measurement target person acquired by the EIT measurement control unit 210 and shows a darker shade in a region having higher electrical impedance. According to FIG. 5, a state in which lung fields from which electrical impedance is highly measured according to the presence of air are located on the left and right can be seen.

Also, as a technique in which the EIT measurement control unit 201 generates the tomographic image, a technique using a finite element method (FEM) in addition to the above-described reverse projection method or a technique of combining the finite element method and the reverse projection method is considered. The EIT measurement control unit 201 can image only a relative change based on a certain state when the reverse projection method is used, or can form a tomographic image based on absolute electrical resistivity [$\Omega$m] in a fault plane by using the finite element method.

The tomographic image acquired as in FIG. 5 is generated only on the basis of electrical signals acquired via the electrode pads 12A to 12H, and does not include information indicating any positional relation in which the electrode pads 12A to 12H are actually arranged. That is, the tomographic image is only a tomographic image generated by virtualizing a relative positional relation between the electrode pads 12A to 12H.

Accordingly, because an absolute positional relation between each coordinate position in the tomographic image and each position in an actual fault plane is not specified in a measurement target in the tomographic image acquired by the EIT measurement control unit 201, the operator is not able to perform accurate diagnosis on the basis of the tomographic image.

Therefore, the EIT measurement device 1 according to this embodiment first performs a process of estimating a shape of a contour of the fault plane of the measurement target portion X using the strain gauges 13A to 13H provided in the measurement belt 10 and the contour estimation unit 202. The above-described EIT measurement control unit 201 generates the tomographic image based on the shape of the contour estimated by the contour estimation unit 202.

Figure 6:
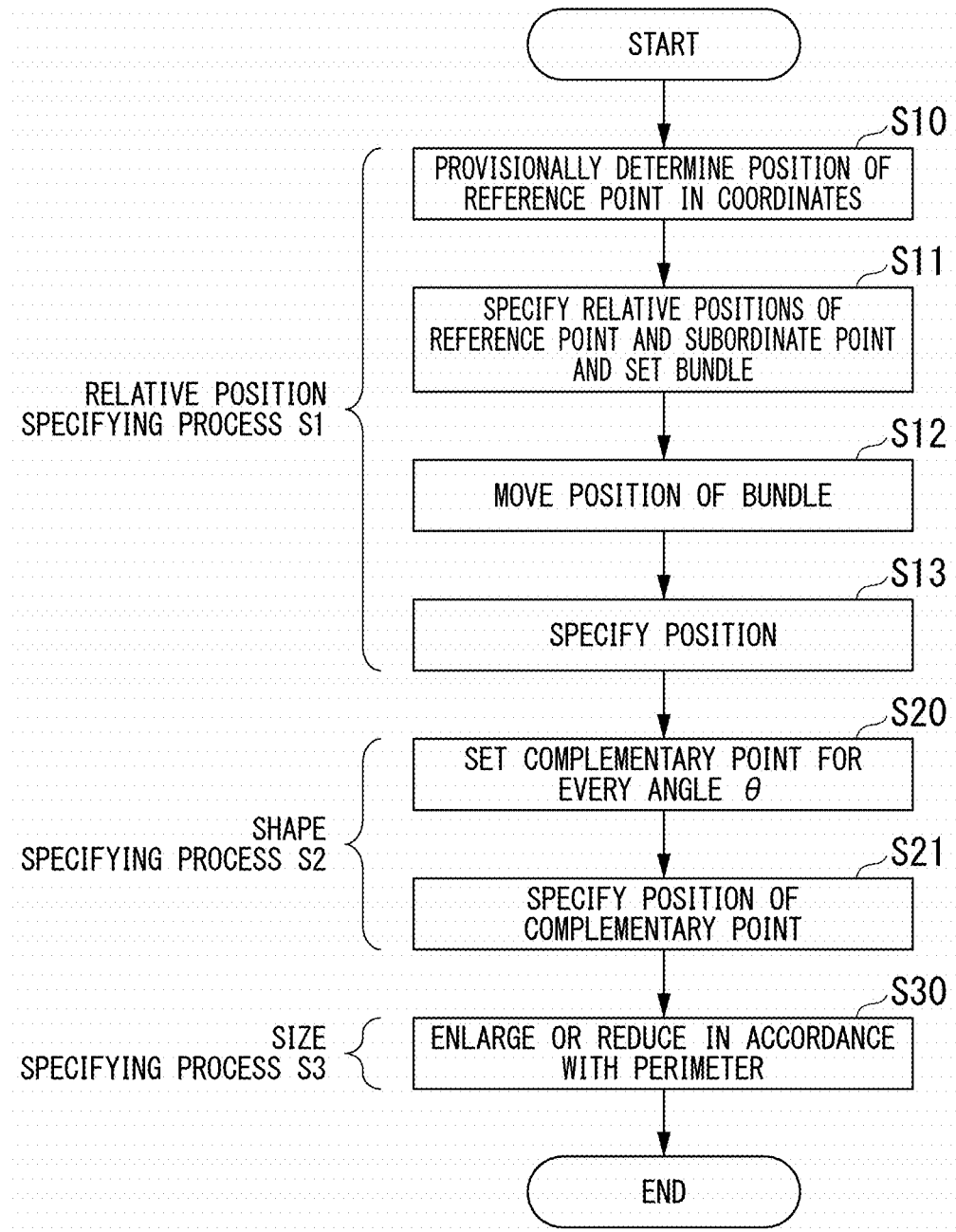
FIG. 6 is a diagram illustrating a processing flow of a contour estimation unit according to the first embodiment.

FIG. 6 is a diagram illustrating a processing flow of the contour estimation unit according to the first embodiment.

Also, FIGS. 7 to 15 are first to ninth diagrams illustrating specific content of each process.

Next, a process in which the contour estimation unit 202 according to this embodiment estimates a contour shape of a fault plane of the measurement target portion X will be specifically described.

As illustrated in FIG. 6, the contour estimation unit 202 estimates a contour shape of the measurement target portion X and a size of the contour shape through a relative position specifying process S1, a shape specifying process S2, and a size specifying process S3. Hereinafter, content of the processes S1 to S3 will be described in detail with reference to FIGS. 6 and 7 to 15.

(Relative Position Specifying Process)

First, the contour estimation unit 202 specifies the relative positional relation for each of the strain gauges 13A to 13H in the relative position specifying process S1.

Figure 7:
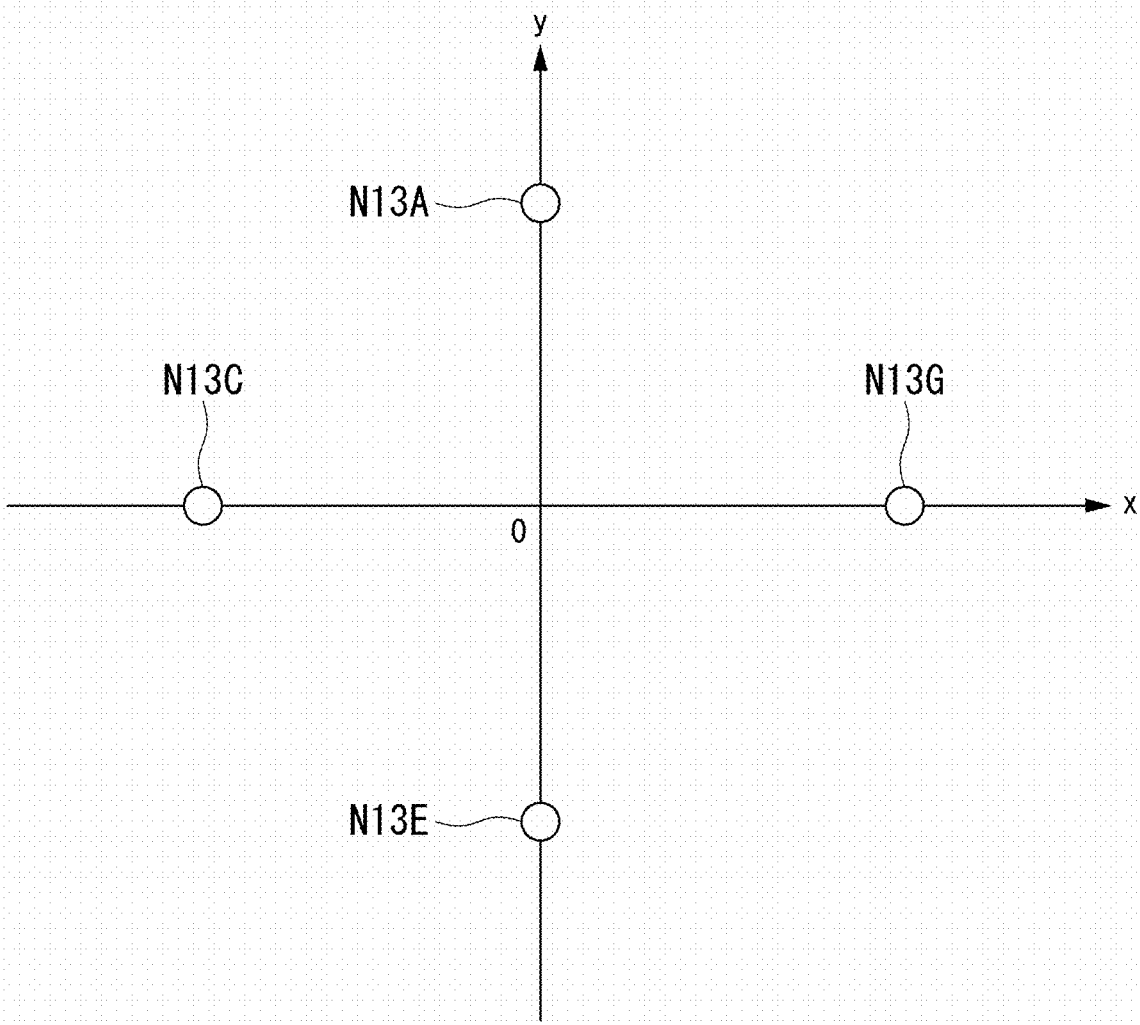
FIG. 7 is a first diagram illustrating specific content of a process of the contour estimation unit according to the first embodiment.

Specifically, as illustrated in FIG. 7, in the first step S10 (FIG. 6), the contour estimation unit 202 first performs a process of setting predetermined xy coordinates and provisionally determining reference points N13A, N13C, N13E, and N13G virtually indicating coordinate positions of the xy coordinates for alternately designated strain gauges (strain gauges 13A, 13C, 13E, and 13G) among the strain gauges 13A to 13H disposed in a row in a longitudinal direction of the measurement belt 10 on the predetermined xy coordinates.

Here, the contour estimation unit 202 specifies coordinate positions of the reference points N13A, N13C, N13E, and N13G up, down, left, and right on x- and y-axes around an origin O, for example, as illustrated in FIG. 7, in the above-described provisional determination process. Specifically, the contour estimation unit 202, for example, reads initial coordinate values pre-stored for each of the reference points N13A to N13G from the HDD 211 and sets the initial coordinate values on coordinates around the origin O. Here, for example, the initial coordinate values for the reference point N13A are stored as (0 [cm], 50 [cm]), the initial coordinate values for the reference point N13C are stored as (−50 [cm], 0 [cm]), the initial coordinate values for the reference point N13E are stored as (0 [cm], −50 [cm]), the initial coordinate values for the reference point N13G are stored as (50 [cm], 0 [cm]), etc.

Next, in a second step S11 (FIG. 6), the contour estimation unit 202 specifies a relative positional relation between the reference points N13A to N13G and subordinate points virtually indicating positions of two strain gauges arranged at both sides of each of the strain gauges 13A to 13G indicated by the reference points N13A to N13G.

Also, a combination of one reference point (for example, N13A) and two subordinate points (for example, N13B1 and N13H2) of both sides of the reference point associated through a relative positional relation is defined as a "bundle" of one set.

In the second step S11, the contour estimation unit 202 specifies a relative positional relation from the reference point N13A by designating points virtually indicating positions of the strain gauges 13B and 13H arranged at both sides of the strain gauge 13A when the measurement belt 10 is wrapped around the measurement target person as subordinate points N13B1 and N13H2 with respect to the reference point N13A indicating a position of the strain gauge 13A. Here, when a relative positional relation of each subordinate point for the reference point is specified, the contour estimation unit 202 receives and refers to curvature data acquired from the strain gauges 13A to 13H from the measurement device 11.

Figure 8:
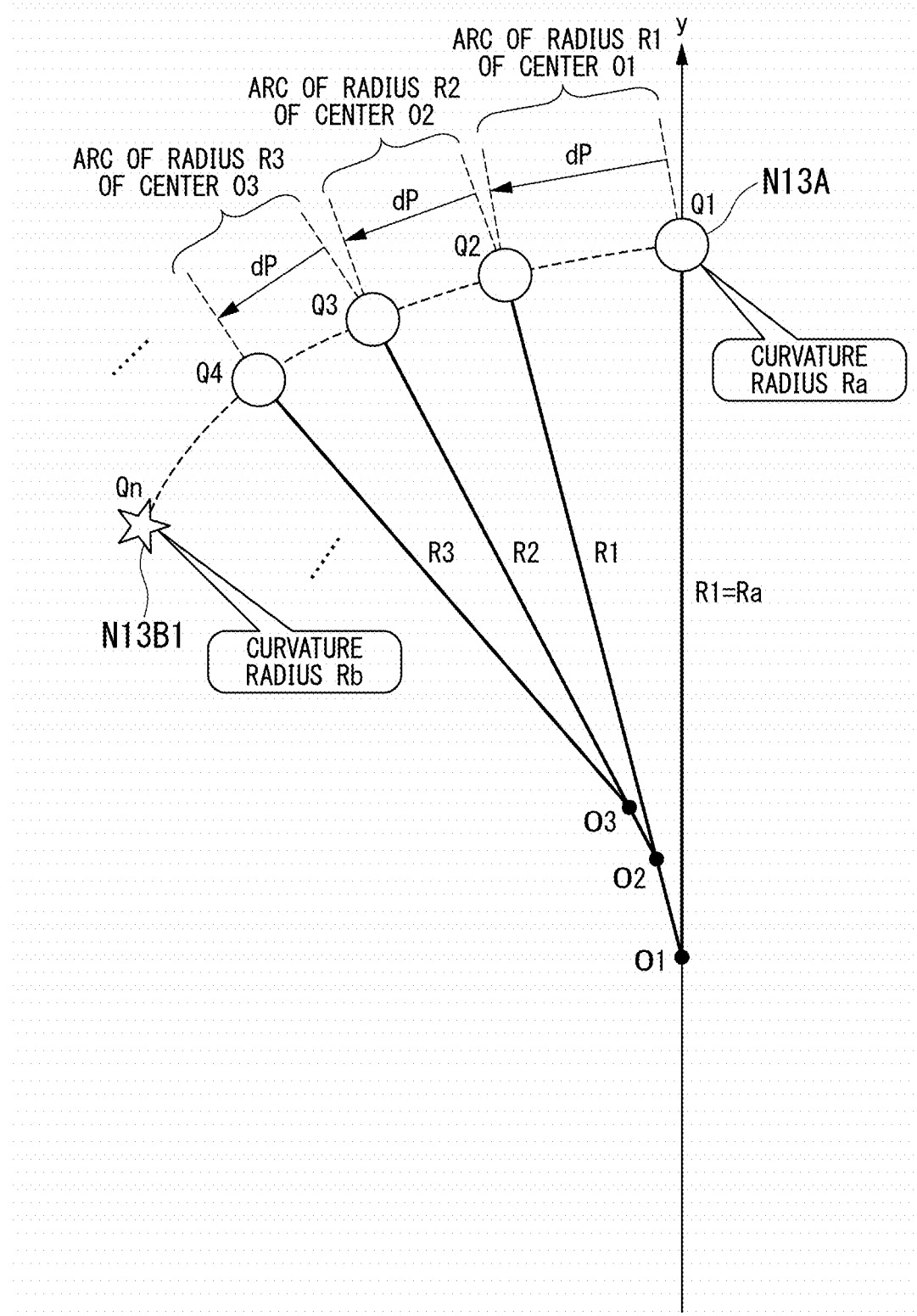
FIG. 8 is a second diagram illustrating specific content of a process of the contour estimation unit according to the first embodiment.

FIG. 8 illustrates a specific process in which the contour estimation unit 202 specifies a relative positional relation of a subordinate point N13B1 for a reference point N13A as an example.

First, the HDD 211 stores an interval between the strain gauge 13A and the strain gauge 13B as a distance P as known data. The contour estimation unit 202 reads the distance P indicating the interval between the strain gauge 13A and the strain gauge 13B by referring to the HDD 211. In addition, the contour estimation unit 202 acquires a curvature radius at each arrangement position from curvature data detected by the strain gauges 13A and 13B.

Here, it is assumed that a curvature radius at a position at which the strain gauge 13A is arranged is Ra and a curvature radius at a position at which the strain gauge 13B is arranged is Rb.

Next, the contour estimation unit 202 calculates a preset micro distance dP on the basis of a distance P indicating an interval between the strain gauge 13A and the strain gauge 13B. This micro distance dP is obtained by sub-dividing a distance P of an interval at which the strain gauges 13A to 13H are arranged into n equal parts (n is an integer of 2 or more). The contour estimation unit 202 specifies a coordinate position of a point Q2 close to the subordinate point N13B1 by a distance dP from a point Q1 (FIG. 8) at which the reference point N13A is arranged.

Here, the contour estimation unit 202 specifies a center O1 determined by the curvature radius R1 based on the point Q1 on a straight line connected between the point Q1 (=reference point N13A) and the origin O from the fact that the curvature radius at the point Q1 (=reference point N13A) is R1 (=Ra) and specifies a coordinate position of the point Q2 separated a micro distance dP in a direction of the subordinate point N13B1 from the point Q1 as a point on an arc determined by the center O1 and the radius R1 (see FIG. 8).

Also, the contour estimation unit 202 may perform a process of specifying a coordinate position of the point Q2 by approximating the micro distance dP between the point Q1 and the point Q2 to a distance of a straight line between the point Q1 and the point Q2 without setting the micro distance dP as a length of an arc when the micro distance dP is set to be sufficiently small.

Next, the contour estimation unit 202 calculates a curvature radius R2 at the point Q2 by assuming that the curvature radius gradually changes from Ra to Rb from the reference point N13A to the subordinate point N13B1. For example, when the micro distance dP is set by dividing the distance P into n equal parts, the contour estimation unit 202 calculates the curvature radius R2 at the point Q2 according to a formula of R2=Ra+(Rb−Ra)/n.

Next, the contour estimation unit 202 specifies a coordinate position of a point Q3 close to the subordinate point N13B1 by a micro distance dP from the point Q2. Here, the contour estimation unit 202 specifies a center O2 determined by the curvature radius R2 based on the point Q2 on a straight line connected between the point Q2 and the center O1 from the fact that the curvature radius at the point Q2 is R2 and specifies a coordinate position of the point Q3 separated by a micro distance dP in a direction of the subordinate point N13B1 from the point Q2 as a point on an arc determined by the center O2 and the radius R2 (see FIG. 8).

The contour estimation unit 202 specifies Q3, Q4, ... and a coordinate position for every micro distance dP while iterating the above process and determines a point Qn when a sum of micro distances dP is a distance P as the subordinate point N13B1. Also, a general formula for obtaining a curvature radius Ri at a point Qi ($1 \le i \le n$) is given as Ri=Ra+(Rb−Ra)×i/n.

Through the above process, relative coordinate values for the subordinate point N13B1 indicating the relative positional relation between the reference point N13A and the subordinate point N13B1 are specified. Likewise, the contour estimation unit 202 specifies relative coordinate values for the subordinate point N13H2. Thus, the contour estimation unit 202 associates the reference point N13A for which a relative positional relation is specified and two subordinate points N13B1 and N13H2 as a bundle of one set.

Through the above-described process, the contour estimation unit 202 can specify a relative positional relation of a subordinate point for a reference point under the assumption that an actual shape of a body surface is precisely reflected (the assumption that the curvature radius at each point between the strain gauges moderately changes).

Figure 9:
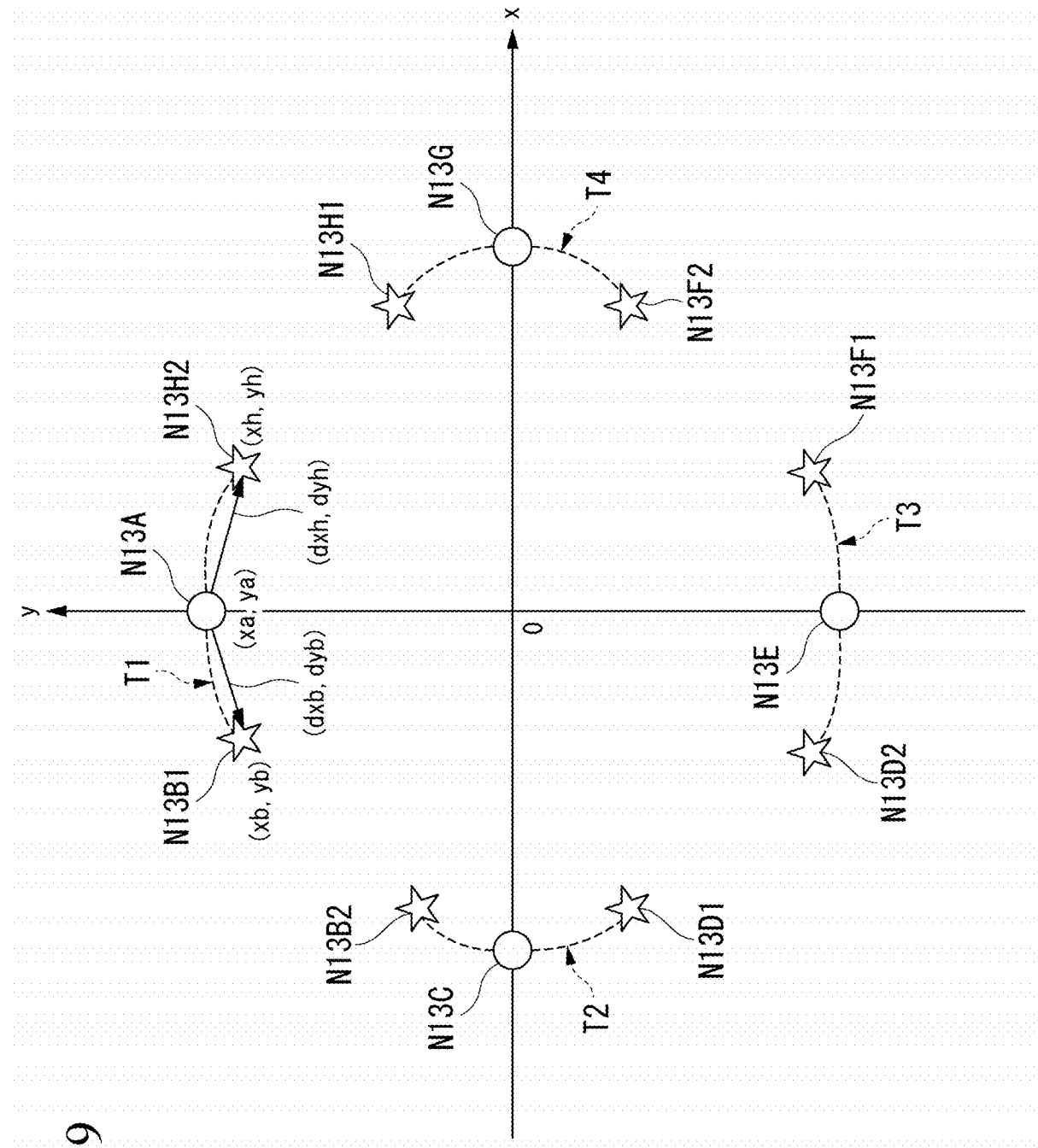
FIG. 9 is a third diagram illustrating specific content of a process of the contour estimation unit according to the first embodiment.

FIG. 9 is a diagram illustrating the reference points N13A to N13G and the subordinate points N13B1 to N13H2 related to the reference points N13A to N13G on the xy coordinates.

As illustrated in FIG. 9, the contour estimation unit 202 specifies coordinate positions (xb, yb) and (xh, yh) of the two subordinate points N13B1 and N13H2 from the relative coordinate values (dxb, dyb) and (dxh, dyh) based on the coordinate position (xa, ya) of the reference point N13A. The contour estimation unit 202 associates a coordinate position (xa, ya) of the reference point N13A and coordinate positions (xb, yb) and (xh, yh) of the two subordinate points N13B1 and N13H2 as information of a bundle T1 and temporarily stores the information in the RAM 210. In this step, the coordinate position (xb, yb) of the subordinate point N13B1 can be calculated by xb=xa+dxb and yb=xa+dyb.

As described above, in the bundle T1, the relative positional relation between the reference point N13A and the two subordinate points N13B1 and N13H2 associated with the reference point N13A is specified.

Likewise, the contour estimation unit 202 associates information of a coordinate position of the reference point N13C with information of coordinate positions of the two subordinate points N13D1 and N13B2 associated with the reference point N13C as information of a bundle T2 and temporarily stores the information in the RAM 210.

Further, the contour estimation unit 202 associates information of coordinate positions of the reference points N13E and N13G and information of coordinate positions of the two subordinate points N13F1 and N13D2 and the two subordinate points N13H1 and N13F2 associated with the reference points N13E and N13G as information of a bundle T3 and a bundle T4 and temporarily stores the information in the RAM 210.

Here, as described above, in the bundle T1, the subordinate point N13B1 is a point virtually indicating the position of the strain gauge 13B arranged adjacent to the strain gauge 13A. On the other hand, in the bundle T2, the subordinate point N13B2 is a point virtually indicating the position of the strain gauge 13B arranged adjacent to the strain gauge 13C.

Assuming that only one electrode pad is located between strain gauges corresponding to a position of the reference point and the total number of electrode pads adhered to the body is eight, the two subordinate points N13B1 and N13B2 belonging to different bundles (T1 or T2) indicate the position of the same strain gauge 13B. Therefore, in this case, the two subordinate points N13B1 (first subordinate point) and N13B2 (second subordinate point) are originally considered to be indicated by the same coordinate position.

In addition, in FIG. 9, the subordinate point N13D1 belonging to the bundle T2 and the subordinate point N13D2 belonging to the bundle T3 indicate the position of the same strain gauge 13D. Likewise, the subordinate points N13F1 and N13F2 indicate the position of the same strain gauge 13F and the subordinate points N13H1 and N13H2 indicate the position of the same strain gauge 13H.

Therefore, similar ideas are established for the subordinate points N13D1 and N13D2, the subordinate points N13F1 and N13F2, and the subordinate points N13H1 and N13H2.

Here, as the third step S12, the contour estimation unit 202 performs a process of moving a position on xy coordinates by changing coordinate positions of points (a reference point and a subordinate point) included in each of the bundles T1 and T2 so that the subordinate point N13B1 included in the bundle T1 matches the subordinate point N13B2 which is the subordinate point included in the bundle T2 and indicates the position of the same strain gauge 13B as the subordinate point N13B1 included in the bundle T1. At this time, the contour estimation unit 202 changes a coordinate position of each point while a relative positional relation between a reference point and a subordinate point included in each of the bundle T1 and the bundle T2 is maintained.

Figure 10:
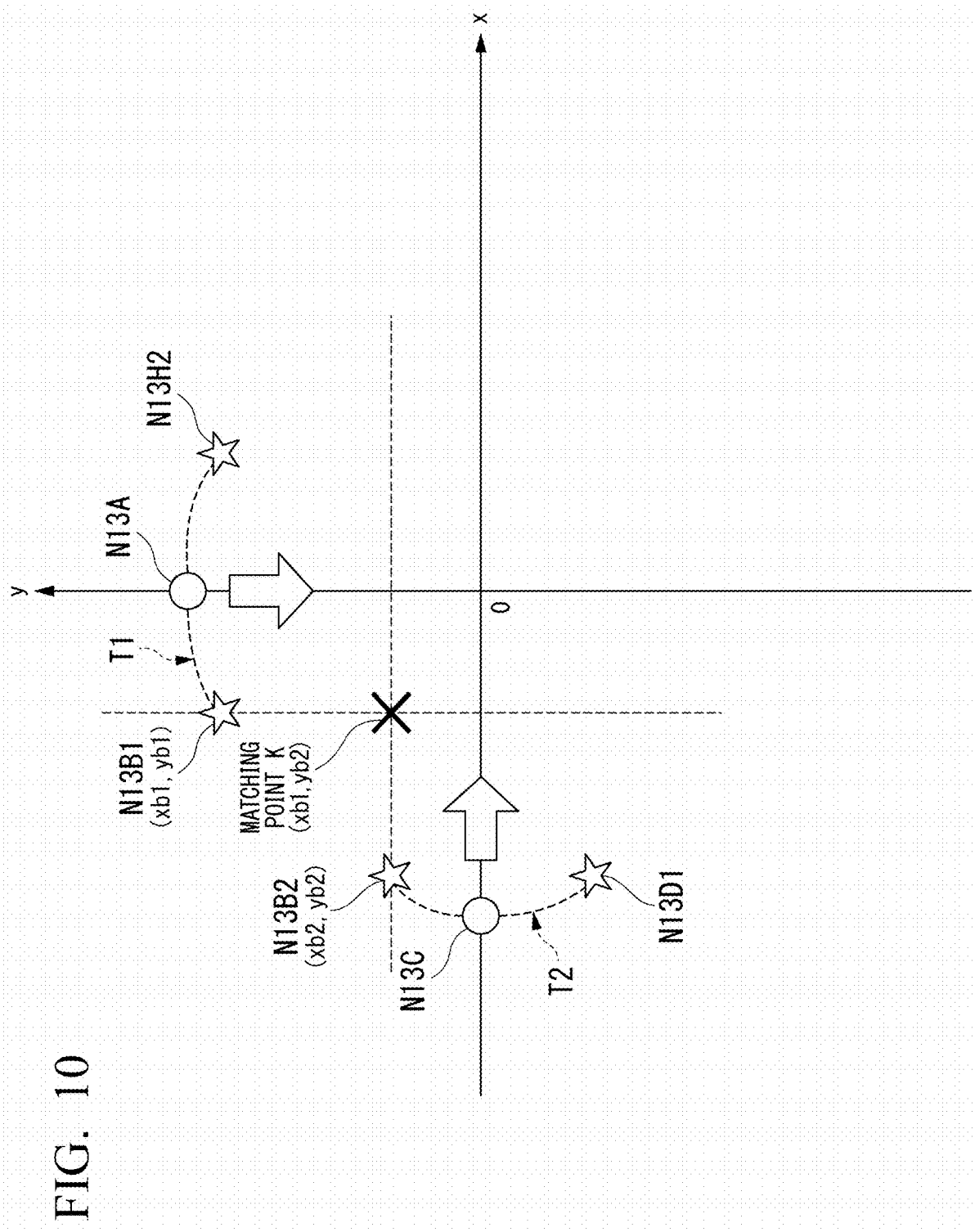
FIG. 10 is a fourth diagram illustrating specific content of a process of the contour estimation unit according to the first embodiment.

FIG. 10 illustrates a process in which the contour estimation unit 202 causes coordinate positions of the subordinate points N13B1 and N13B2 indicating the position of the same strain gauge 13B to match by changing coordinate positions of points (a reference point and a subordinate point) included in the bundle T1 and the bundle T2. Specifically, as illustrated in FIG. 10, the contour estimation unit 202 performs a process of changing a coordinate position to move the bundle T1 along the y axis in parallel. The term "to move in parallel," for example, indicates a process of adding or subtracting the same value even for y coordinate values of the subordinate points N13B1 and N13H2 simultaneously when the coordinate position is changed by adding a predetermined value to the y coordinate value of the reference point N13A or subtracting the predetermined value from the y coordinate value of the reference point N13A and changing a coordinate position while maintaining a relative positional relation of each point. However, the contour estimation unit 202 can perform a process of changing a coordinate position to move the bundle T1 in parallel by substantially performing a process of changing only the coordinate position of the reference point N13A because coordinate positions of the subordinate points N13B1 and N13H2 are specified according to relative coordinate values based on a coordinate position of the reference point N13A in this embodiment.

Likewise, the contour estimation unit 202 performs a process of changing the coordinate position to move the bundle T2 to the origin O in parallel along the x-axis.

Here, when the bundles T1 and T2 are moved in parallel along the y-axis and the x-axis, the contour estimation unit 202 specifies a coordinate position of a matching point K (FIG. 10) at which the subordinate points N13B and N13B2 overlap. Here, the contour estimation unit 202 specifies the coordinate position of the matching point K as (xb1, yb2) when a coordinate position at a current time point of the subordinate point N13B1 is (xb1, yb1) and a coordinate position at a current time point of the subordinate point N13B2 is (xb2, yb2).

The contour estimation unit 202 performs a process of calculating a difference (yb1−yb2) between the y coordinate values of each subordinate point N13B1 and the matching point K and subtracting the difference (yb1−yb2) from the y coordinate value of the reference point N13A included in the bundle T1. Likewise, the contour estimation unit 202 performs a process of calculating a difference (xb1−xb2) between the x coordinate values of each subordinate point N13B2 and the matching point K and adding the difference (xb1−xb2) to the x coordinate value of the reference point N13C included in the bundle T2.

Thus, the contour estimation unit 202 changes coordinate positions of the bundles T1 and T2 so that coordinate positions of the subordinate points N13B1 and N13B2 match.

Figure 11:
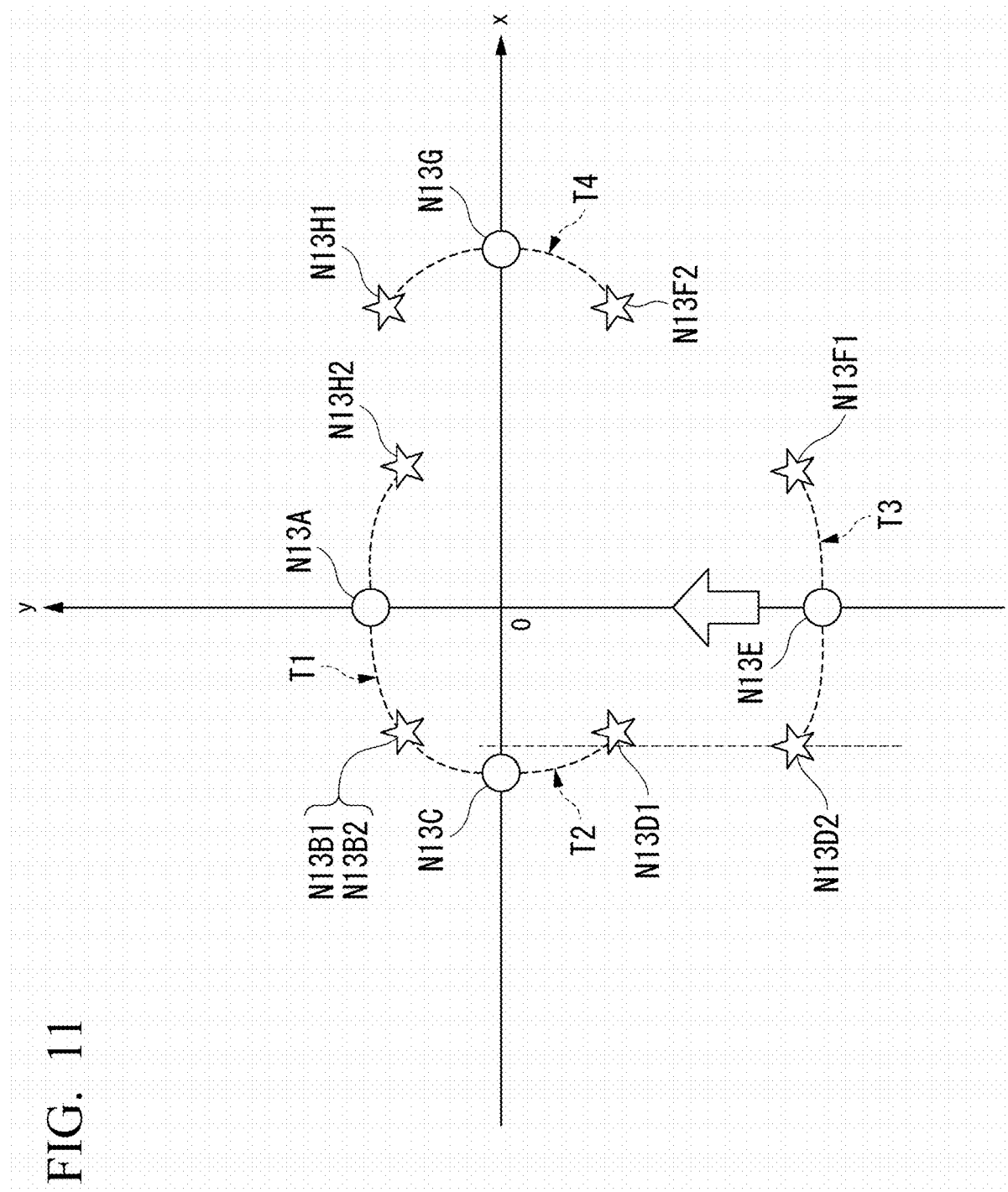
FIG. 11 is a fifth diagram illustrating specific content of a process of the contour estimation unit according to the first embodiment.

Next, FIG. 11 illustrates a process in which the contour estimation unit 202 causes positions of the subordinate points N13D1 and N13D2 indicating the position of the same strain gauge 13D to match by changing a coordinate position of each point included in the bundle T3.

As illustrated in FIG. 11, the contour estimation unit 202 performs a process of changing a coordinate position of each point of the bundle T3 so that the subordinate point N13D2 of the bundle T3 is closest to the subordinate point N13D1 of the bundle T2 when the bundle T3 is moved in parallel along the y-axis. Also, because the coordinate position of the bundle T2 is already fixed in this step, coordinate positions of the subordinate points N13D1 and N13D2 do not completely match and have some error.

After this process, the contour estimation unit 202 further performs a process of changing a coordinate position of each point of the bundle T4 so that the subordinate point N13F2 of the bundle T4 is closest to the subordinate point N13F1 of the bundle T3 when the bundle T4 is moved in parallel along the x-axis. In this step, as described above, the coordinate positions of the subordinate points N13F1 and N13F2 do not completely match because the coordinate position of the bundle T3 is already fixed. Also, the coordinate positions of the subordinate point N13H1 of the bundle T4 and the subordinate point N13H2 of the bundle T1 do not match.

Accordingly, in this step, error amounts of coordinate positions at a pair of subordinate points N13B1 and N13B2, a pair of subordinate points N13D1 and N13D2, a pair of subordinate points N13F1 and N13F2, and a pair of subordinate points N13H1 and N13H2 become non-uniform. Consequently, the contour estimation unit 202 finely adjusts coordinate positions of the bundles T1 to T4 again so that an error amount of a coordinate position at a pair of subordinate points becomes regular. For example, the contour estimation unit 202 performs micro movement while the relative positional relation of each point included in the bundles T1 to T4 is maintained for each of the bundles T1 to T4 and stops micro movement at a point in time at which the error amount is uniform while calculating the error amount for every micro movement.

Figure 12:
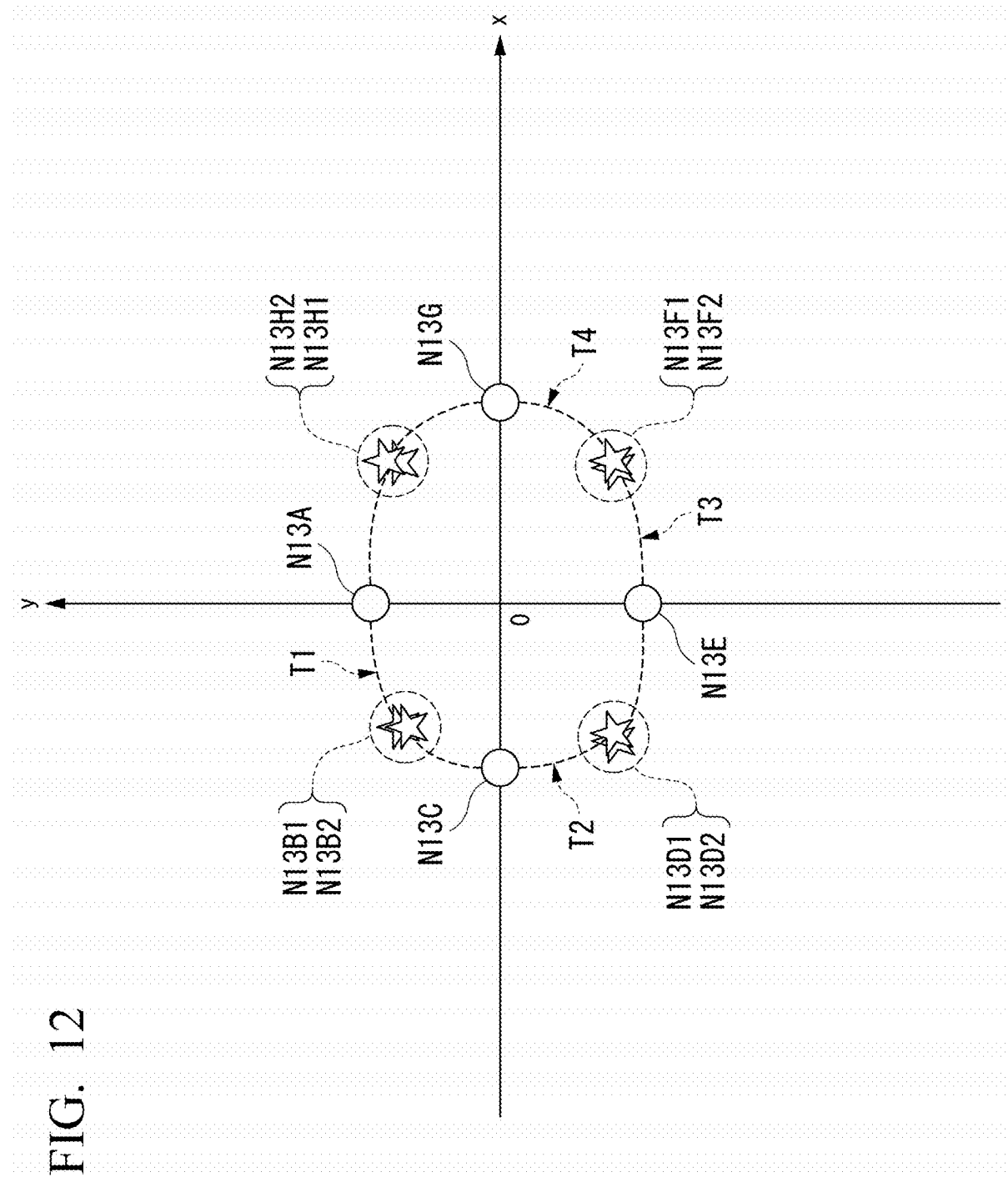
FIG. 12 is a sixth diagram illustrating specific content of a process of the contour estimation unit according to the first embodiment.

FIG. 12 illustrates a state immediately after parallel movement for the bundles T1 to T4 is completed.

As illustrated in FIG. 12, when error amounts of coordinate positions at a pair of subordinate points N13B1 and N13B2, a pair of subordinate points N13D1 and N13D2, a pair of subordinate points N13F1 and N13F2, and a pair of subordinate points N13H1 and N13H2 become uniform, final positions of the bundles T1 to T4 are specified.

The contour estimation unit 202 calculates a center point between coordinate positions indicated by the subordinate points N13B1 and N13B2 and specifies the coordinate position of the calculated center point as a point N13B indicating a position of the strain gauge 13B (the fourth step S13 in FIG. 6). The contour estimation unit 202 also performs a similar process on the other pairs of subordinate points (a pair of N13D1 and N13D2, a pair of N13F1 and N13F2, and a pair of N13H1 and N13H2).

Figure 13:
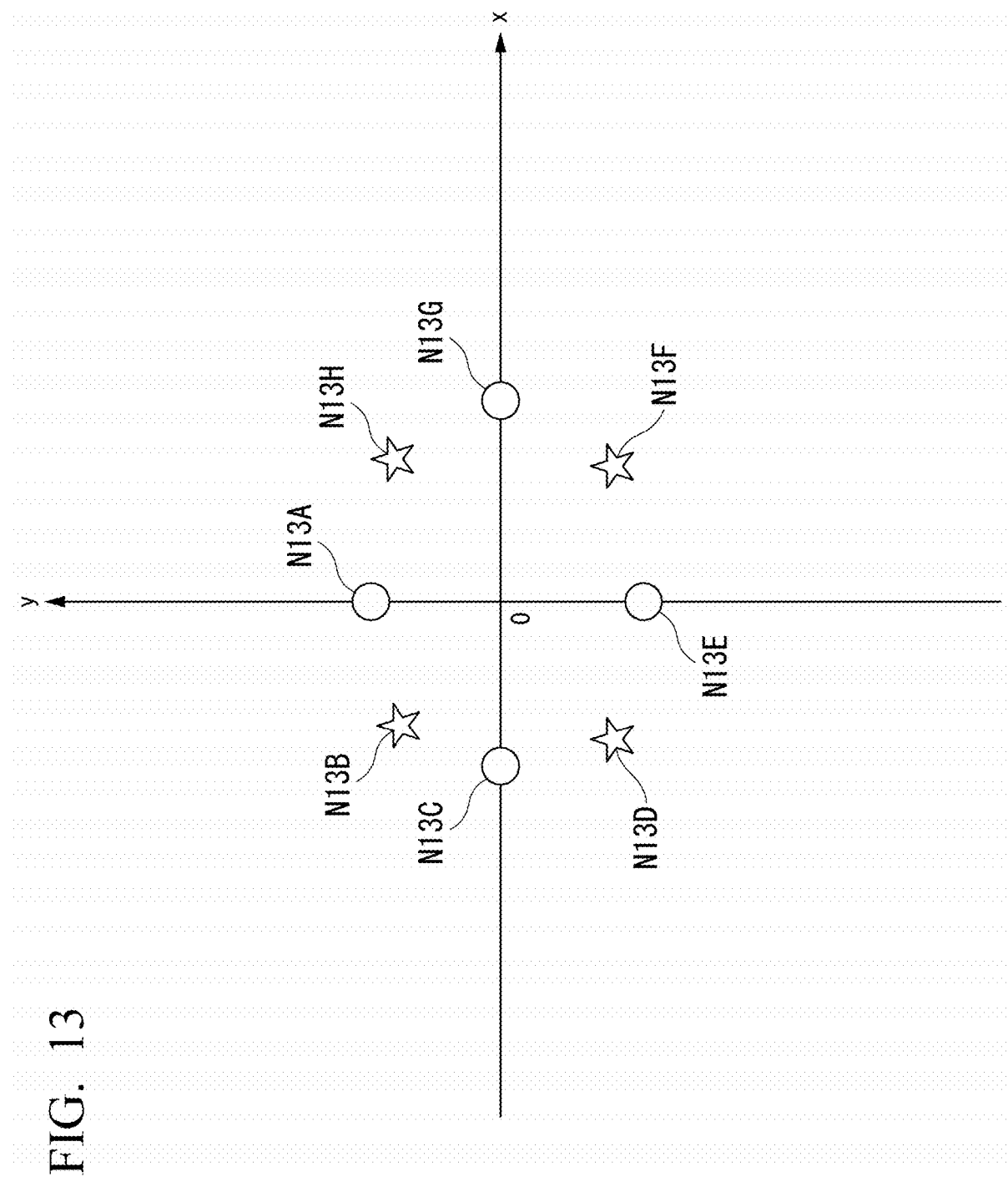
FIG. 13 is a seventh diagram illustrating specific content of a process of the contour estimation unit according to the first embodiment.

FIG. 13 illustrates a state immediately after a process of the above-described fourth step S13 is completed.

As illustrated in FIG. 13, the contour estimation unit 202 specifies points N13A to N13H indicating a relative positional relation between the strain gauges 13A to 13H on coordinates through processing of the relative position specifying process S1 (the first step S10 to the third step S12).

Also, in the process described using FIGS. 10 to 13, more generally, when coordinate positions of reference points (N13A to N13G) at which the bundles T1 to T4 are shown are moved in a direction of the origin O, coordinate positions after movement of the reference point and the subordinate point constituting each bundle are calculated so that a distance of a coordinate position of each subordinate point indicating the same strain gauge at each bundle of a state in which the relative positional relation between the reference point and the subordinate point maintains the relative positional relation before the movement is closest. The contour estimation unit 202 specifies the center point between the subordinate points indicating the same strain gauge as a point indicating the position of the strain gauge.

(In Terms of Shape Specifying Process)

The contour estimation unit 202 according to this embodiment executes the shape specifying process S2 of specifying a contour shape of a measurement target portion X while coupling the strain gauges 13A to 13H by a predetermined function curve after a relative positional relation between the strain gauges 13A to 13H is specified by completing the relative position specifying process S1 (FIG. 6).

Figure 14A:
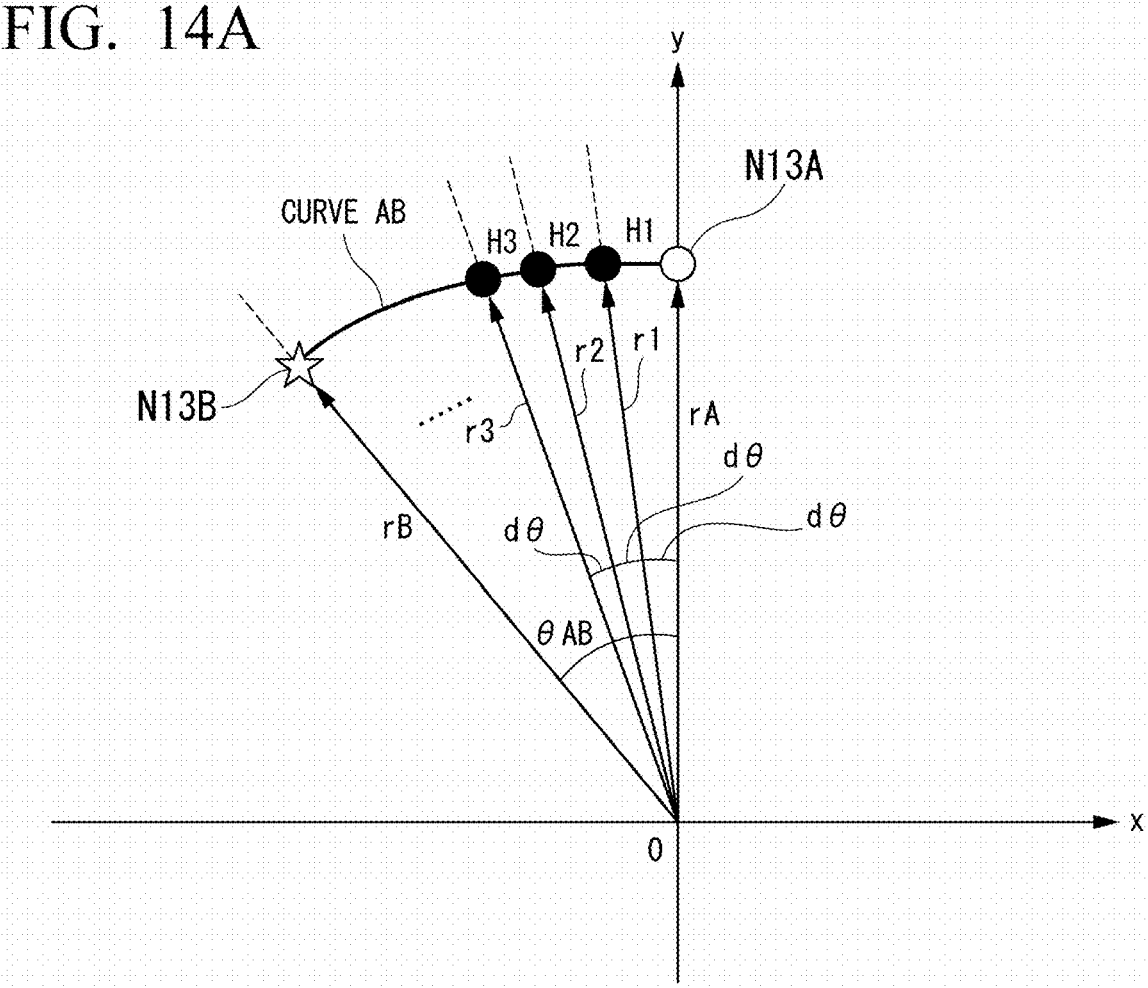
FIG. 14A is an eighth diagram illustrating specific content of a process of the contour estimation unit according to the first embodiment.
Figure 14B:
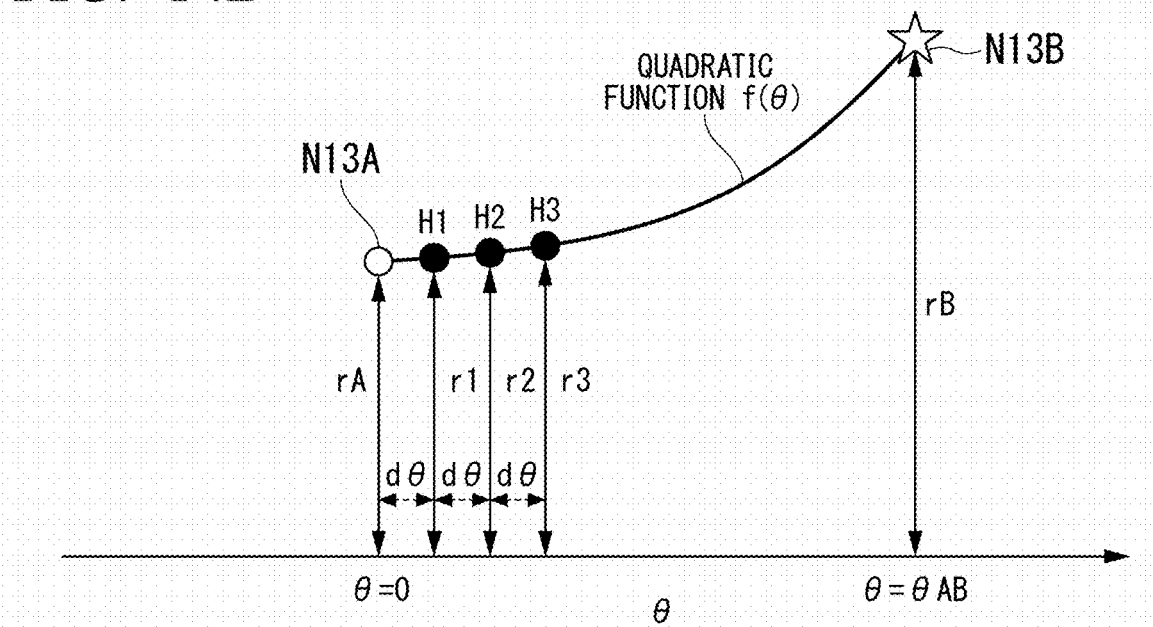
FIG. 14B is an eighth diagram illustrating specific content of a process of the contour estimation unit according to the first embodiment.

FIGS. 14A and 14B are diagrams illustrating a specific content of a processing of the shape specifying process S2.

As illustrated in FIG. 14A, the contour estimation unit 202 specifies a curve AB connected between a point N13A indicating a position of a strain gauge 13A and a point N13B indicating a position of a strain gauge 13B adjacent to the strain gauge 13A. Here, the curve AB specified by the contour estimation unit 202 is obtained by estimating a shape of a contour between the strain gauge 13A and the strain gauge 13B.

Specifically, the contour estimation unit 202 performs a process of setting a plurality of complementary points H1, H2, . . . for specifying the curve AB between the point N13A and the point N13B.

First, the contour estimation unit 202 specifies an angle θAB formed by a line segment having a length rA connected between the point N13A and the origin O and a line segment having a length rB connected between the point N13B and the origin O with respect to the origin O (see FIG. 14A).

Next, the contour estimation unit 202 specifies a preset micro angle dθ after referring to the HDD 211. This micro angle dθ indicates an angle obtained by fine division by equally dividing the angle θAB into m equal parts (m is an integer of 2 or more). The contour estimation unit 202 specifies the complementary point H1 on a straight line obtained by inclining the line segment connected between the point N13A and the origin O by the micro angle dθ. Subsequently, the contour estimation unit 202 specifies the complementary point H2 on a straight line obtained by further inclining the line segment by the micro angle dθ. As described above, the contour estimation unit 202 specifies the complementary points H1, H2, . . . for a plurality of straight lines passing through the origin O specified for every micro angle dθ (see FIG. 14A) (step S20 in FIG. 6).

Here, the contour estimation unit 202 specifies positions of the complementary points H1, H2, . . . on the basis of a predetermined function (quadratic function f(θ)). This quadratic function f(θ) is a function of angles θ formed by the complementary points H1, H2, . . . , the origin O, and the point N13A indicating a position of the strain gauge 13A and specifies lengths r1, r2, . . . of the line segments connecting the complementary points H1, H2, . . . and the origin O as a solution.

Also, because coordinate positions of the point N13A and the point N13B are specified through the relative position specifying process S1, the contour estimation unit 202 calculates a distance rA between the point N13A and the origin O and a distance rB between the point N13B and the origin O from the specified coordinate positions. The contour estimation unit 202 sets the quadratic function f(θ) so that the constraint conditions of f(θ)=rA and f(θAB)=rB are satisfied (see FIG. 14B).

For example, an angle formed by the complementary point H1, the origin O, and the point N13A indicating the position of the strain gauge 13A is dθ. Consequently, as illustrated in FIG. 14B, a length r1 of the line segment connecting the complementary point H1 and the origin O is calculated by r1=f(dθ). Likewise, a length r2 of the line segment connecting the complementary point H2 and the origin O is calculated by r2=f(2×dθ).

The contour estimation unit 202 specifies positions for all the complementary points H1, H2, . . . by iterating the above-described process (step S21 in FIG. 6).

Thus, the contour estimation unit 202 can specify a curve AB connecting the complementary points H1, H2, . . . . Likewise, the contour estimation unit 202 specifies all curves between other strain gauges such as a curve BC connecting the strain gauge 13B and the strain gauge 13C. The contour estimation unit 202 can finally specify a closed curve which connects all the strain gauges 13A to 13H, that is, a shape of a contour of the measurement target portion X.

(In Terms of Size Specifying Process)

The contour estimation unit 202 according to this embodiment executes a size specifying process S3 of specifying a size of a shape of a contour so that the size matches a size of a portion serving as an actual measurement target after the shape of the contour of the portion serving as the measurement target is estimated by completing the shape specifying process S2 (FIG. 6).

Specifically, the contour estimation unit 202 performs a process of enlarging or reducing the estimated contour shape so that a perimeter of the contour shape estimated in the shape specifying process S2 matches a separately measured perimeter of the measurement target portion X in the size specifying process S3 (step S30 in FIG. 6).

Here, the separately measured perimeter is a perimeter of the measurement target portion X, for example, actually measured using a measure or the like, separately from EIT measurement using the EIT measurement device 1.

Figure 15:
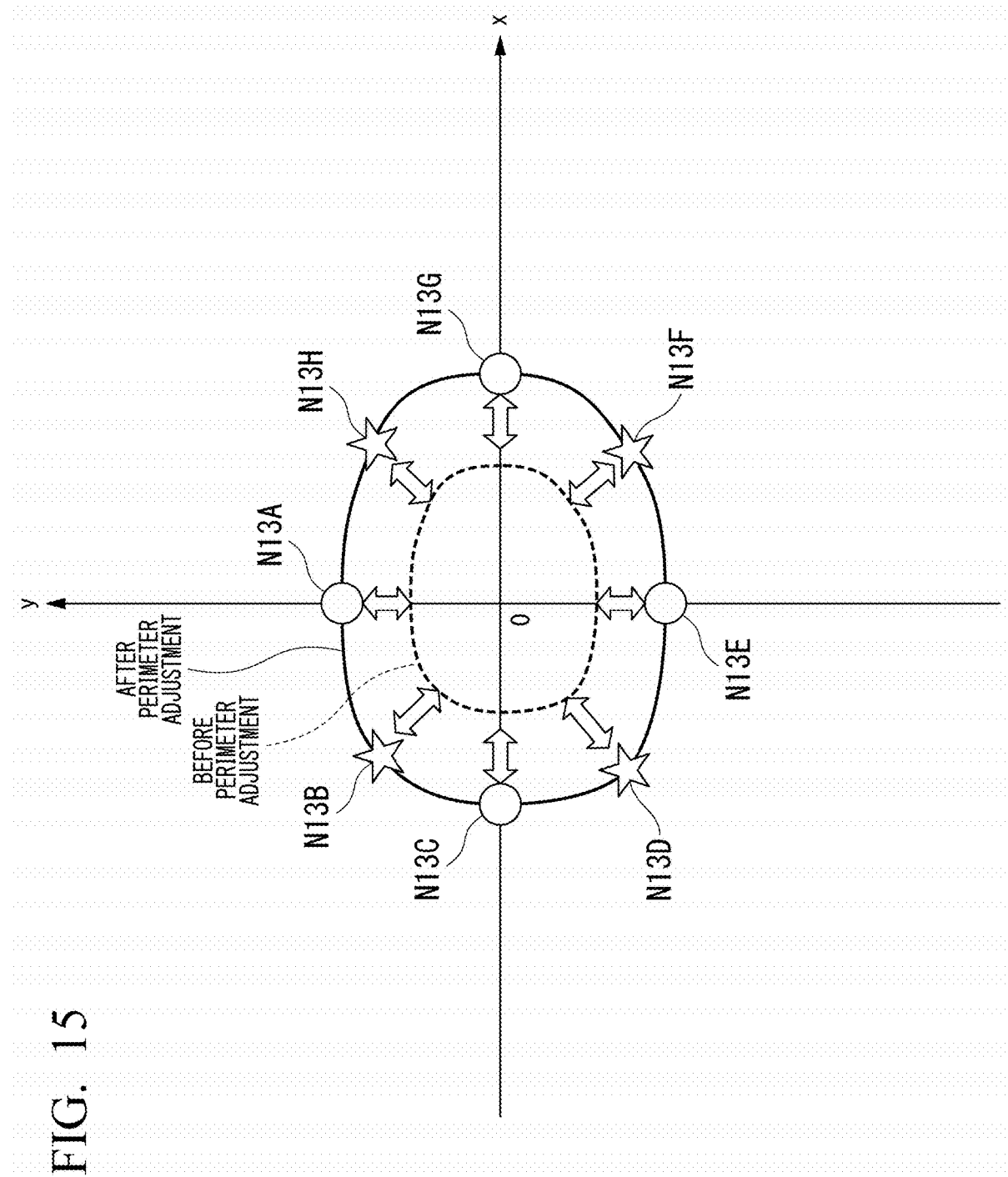
FIG. 15 is a ninth diagram illustrating specific content of a process of the contour estimation unit according to the first embodiment.

FIG. 15 illustrates a state of a process in which the contour estimation unit 202 enlarges or reduces the estimated contour shape.

The contour estimation unit 202 calculates the perimeter of the contour for which the shape is estimated in the shape specifying process S2 and compares the calculated perimeter with the perimeter of the measurement target portion X separately measured using the measure or the like. When the perimeter of the estimated contour is different from the actually measured perimeter, the perimeter of the estimated contour and the above-described actually measured perimeter are adjusted to match by enlarging or reducing the entire size while the estimated contour shape is maintained.

The contour estimation unit 202 estimates a contour shape of the measurement target portion X and a size of the contour shape through the above process.

(Effects)

Figure 16:
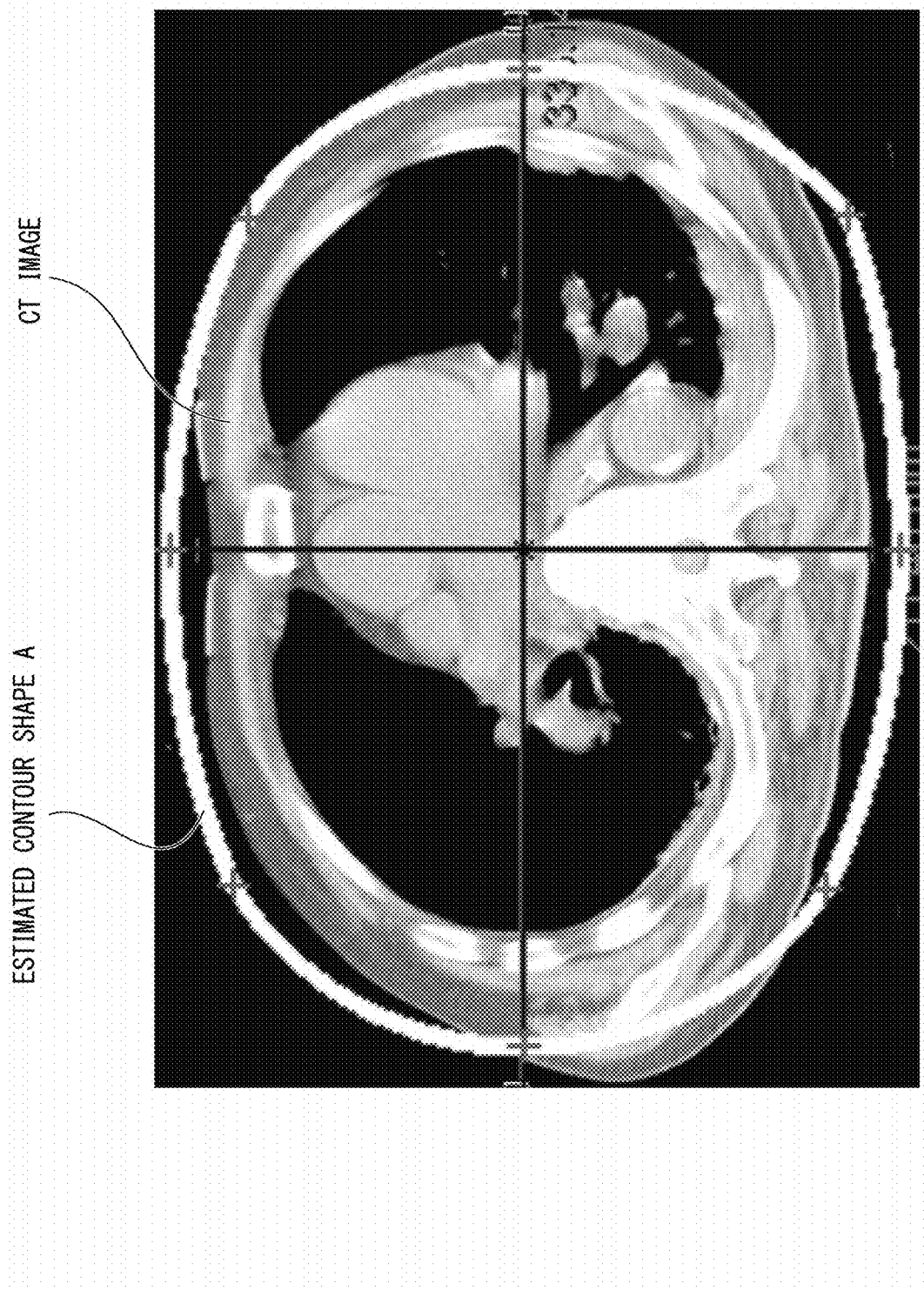
FIG. 16 is a diagram illustrating a processing result of the contour estimation unit according to the first embodiment.

FIG. 16 is a diagram illustrating a processing result of the contour estimation unit according to the first embodiment.

FIG. 16 illustrates a diagram in which a contour shape A of a thorax of a measurement target person estimated by the contour estimation unit 202 through the above-described processes S1 to S3 and a CT image acquired through a separate X ray CT of the thorax are superimposed. As illustrated in FIG. 16, a contour shape A estimated by the contour estimation unit 202 on the basis of the strain gauges 13A to 13H provided in the measurement belt 10 approximately matches a contour shape of the thorax shown in the CT image.

Figure 17A:
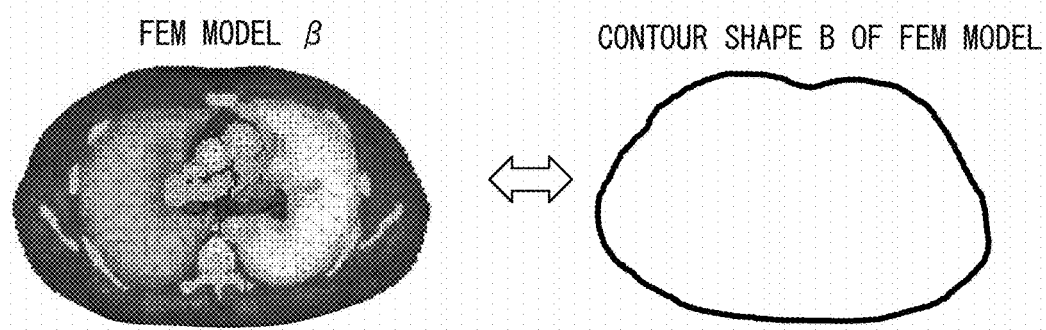
FIG. 17A is a diagram illustrating an example of an image generation process by the EIT measurement control unit according to the first embodiment.
Figure 17B:
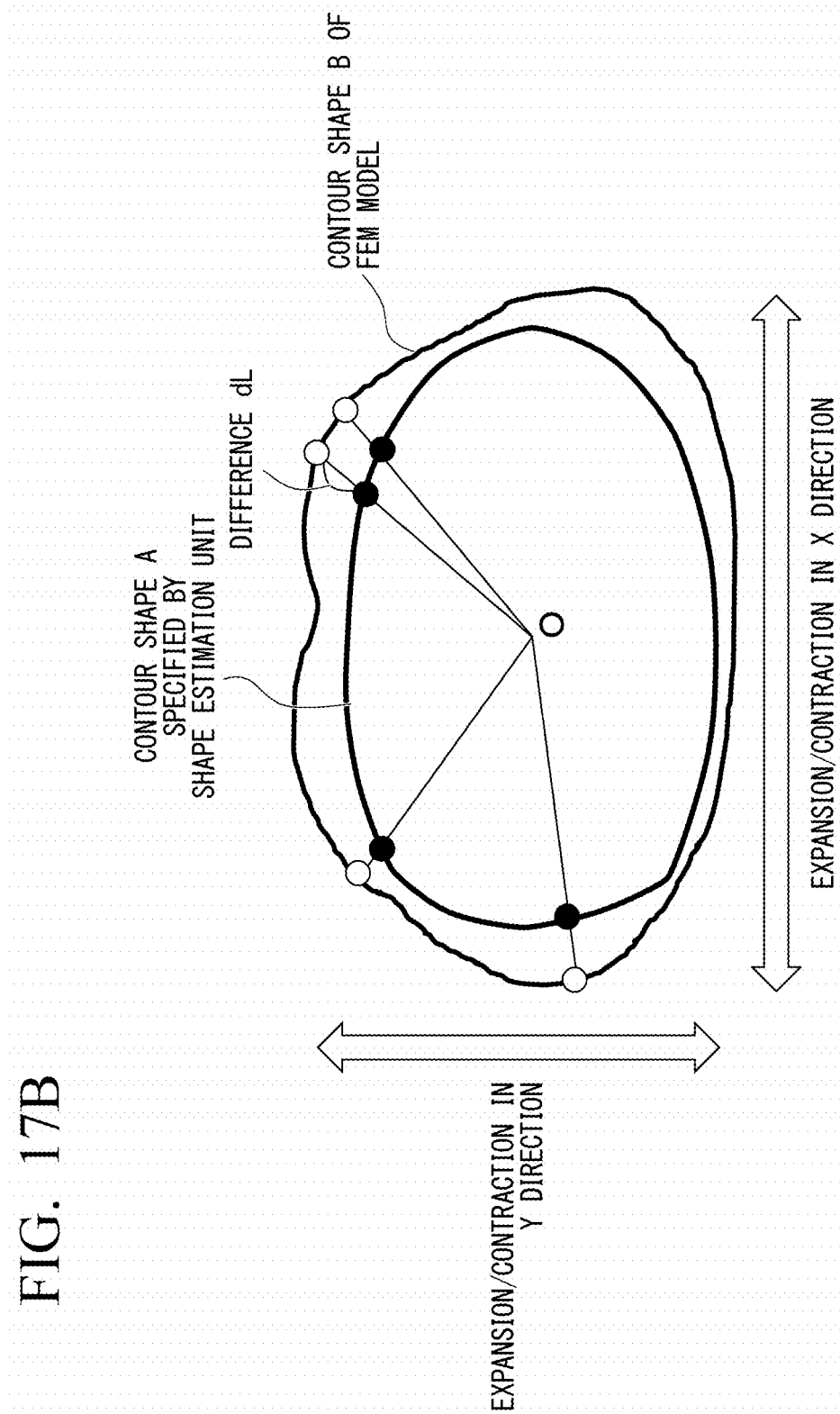
FIG. 17B is a diagram illustrating an example of an image generation process by the EIT measurement control unit according to the first embodiment.

FIGS. 17A and 17B are first and second diagrams illustrating examples of an image generation process by the EIT measurement control unit according to the first embodiment.

Here, a specific technique in which the EIT measurement control unit 201 generates a tomographic image on the basis of the contour shape A estimated by the contour estimation unit 202 will be briefly described. Here, the case in which the EIT measurement control unit 201 generates a tomographic image on the basis of the above-described finite element method is considered.

First, the EIT measurement control unit 201 designates a predetermined FEM model β (the left of FIG. 17A) pre-stored in the HDD 211. This FEM model β is pre-created on the basis of a CT image or the like of another measured person, and the same portion (for example, a chest portion) as that of the measurement target portion X in EIT measurement is designated. The EIT measurement control unit 201 superimposes the contour shape A estimated by the contour estimation unit 202 with the contour shape B (the right of FIG. 17A) of the designated FEM model f to compare the contour shapes A and B (see FIG. 17B).

Next, the EIT measurement control unit 201 performs a process of expanding/contracting the contour shape B at a fixed ratio in each of an X direction and a Y direction so that a difference between the contour shape A and the contour shape B is minimized. Specifically, the EIT measurement control unit 201 integrates a difference dL between a position of each point (a point indicated by a black dot in FIG. 17B) constituting the contour shape A and a point (a point indicated by a white dot in FIG. 17B) corresponding to each point indicated by the black dot on the contour shape B in the whole periphery and calculates an expansion/contraction ratio (rx, ry) for the X and Y directions in which an integrated value of the difference dL is minimized.

Subsequently, the EIT measurement control unit 201 applies the calculated expansion/contraction ratio (rx, ry) to the initially designated FEM model β and generates an FEM model β' expanded/contracted in each of the X direction and the Y direction at the same ratio.

The EIT measurement control unit 201 acquires a tomographic image based on a contour shape and a size of the measurement target portion X by applying a finite element method for the FEM model β' to voltage signals acquired via the electrode pads 12A to 12H.

Also, a plurality of different FEM model β1, β2, . . . created on the basis of CT images of a plurality of measured persons may be pre-stored in the HDD 211. In this case, the EIT measurement control unit 201 may perform a process of selecting an FEM model closest to the contour shape A estimated by the contour estimation unit 202. Specifically, the EIT measurement control unit 201 selects an FEM model β a having a perimeter matching the perimeter of the contour shape A, for example, in a chest portion, among the plurality of FEM models β1, β2, . . . . An expansion/contraction process similar to that described above is performed on the FEM model β a in which the perimeter matches.

As described above, the operator can estimate a contour shape of a measurement target portion X in a measurement target person by merely wrapping the measurement belt 10 around the measurement target portion X using the EIT measurement device 1 and acquire a tomographic image based on the estimated contour shape.

Therefore, the operator can perform an accurate diagnosis on the basis of a tomographic image even when a shape or a size is different for every measurement target because it is possible to specify an absolute positional relation between the tomographic image and a portion serving as a measurement target.

According to the EIT measurement device according to the first embodiment, it is possible to simply perform a more accurate diagnosis even for various measurement targets having a different shape or size of a contour.

Also, the EIT measurement device 1 according to the first embodiment is not limited to the above-described aspect but can be modified as follows.

For example, a process in which the contour estimation unit 202 specifies a relative positional relation between the strain gauges 13A to 13H by moving the bundles T1 to T4 in parallel in the third step S12 (see FIGS. 10 to 12) is not limited to the content of the above-described process.

For example, the order in which the bundles T1 to T4 are moved in parallel by the contour estimation unit 202 is optional, and processing content is not particularly limited as long as a shift from the state illustrated in FIG. 9 to the state illustrated in FIG. 12 is possible.

Also, the contour estimation unit 202 is assumed to estimate a contour between points indicating the strain gauges 13A to 13H between which the relative positional relation is specified with a plurality of supplementary points on the basis of a quadratic function in step S21 of the shape specifying process S2 (see FIGS. 14A and 14B). However, as a modified example of this embodiment, a position of the supplementary point may be specified with another function (a linear function, a cubic function, or the like) besides the quadratic function. Also, a function of enabling a proper function or a necessary parameter to be appropriately selected from among a plurality of function candidates on the basis of an empirical rule or the like may be provided.

Also, according to the above description, an aspect in which the EIT measurement main body unit 20 is connected to the measurement circuit 11 of the measurement belt 10 via the signal cable 19 is provided. However, other modified examples of this embodiment are not limited to the aspect. For example, an aspect in which the EIT measurement main body unit 20 is mounted on the measurement circuit 11 may be provided.

In this case, the measurement circuit 11 equipped with the function of the EIT measurement main body unit 20 may further have a function of wireless or wired communication with an external device and a function of transmitting an acquired tomographic image to various terminal devices (a smartphone, a tablet type computer, a small size game machine, etc.) wirelessly or by wire.

Second Embodiment

Next, an EIT measurement device 1 according to the second embodiment will be described with reference to the drawings. Also, the same function components as those of the first embodiment are assigned the same reference signs and description thereof will be omitted.

Figure 18:
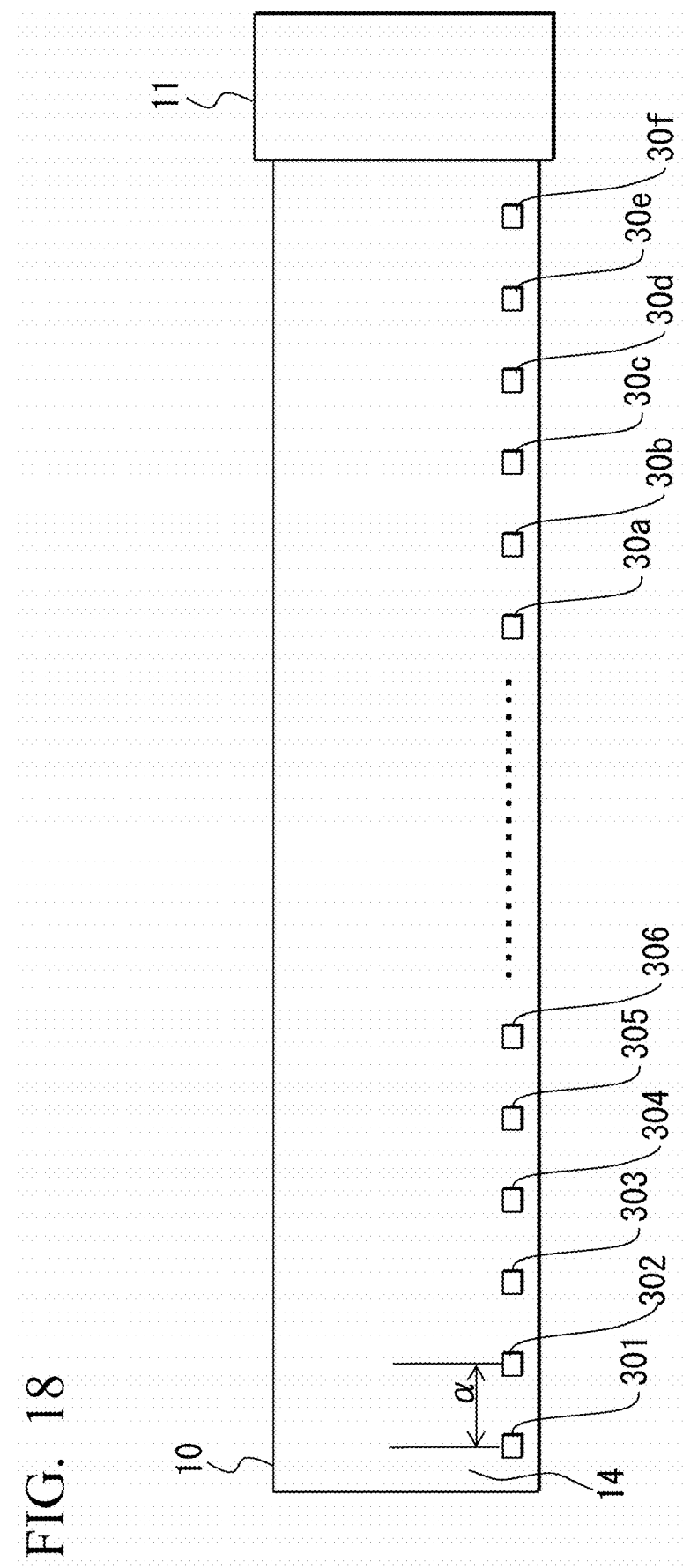
FIG. 18 is a diagram illustrating a functional configuration of a measurement belt according to a second embodiment.

FIG. 18 is a diagram illustrating a functional configuration of a measurement belt according to the second embodiment.

Also, the notation of electrode pads 12A to 12H and strain gauges 13A to 13H is omitted to avoid a complexity in the drawings in FIG. 18, but the electrode pads 12A to 12A and the strain gauges 13A to 13H are configured to be actually periodically arranged on a flexible substrate 14 as in the first embodiment.

As illustrated in FIG. 18, a measurement belt 10 according to this embodiment includes perimeter measurement electrode pads 301, 302, . . . , 30*f* attached to the measurement belt 10 and periodically arranged at intervals α in a longitudinal direction of the measurement belt 10 (in parallel to the electrode pads 12A to 12H or the like).

Figure 19:
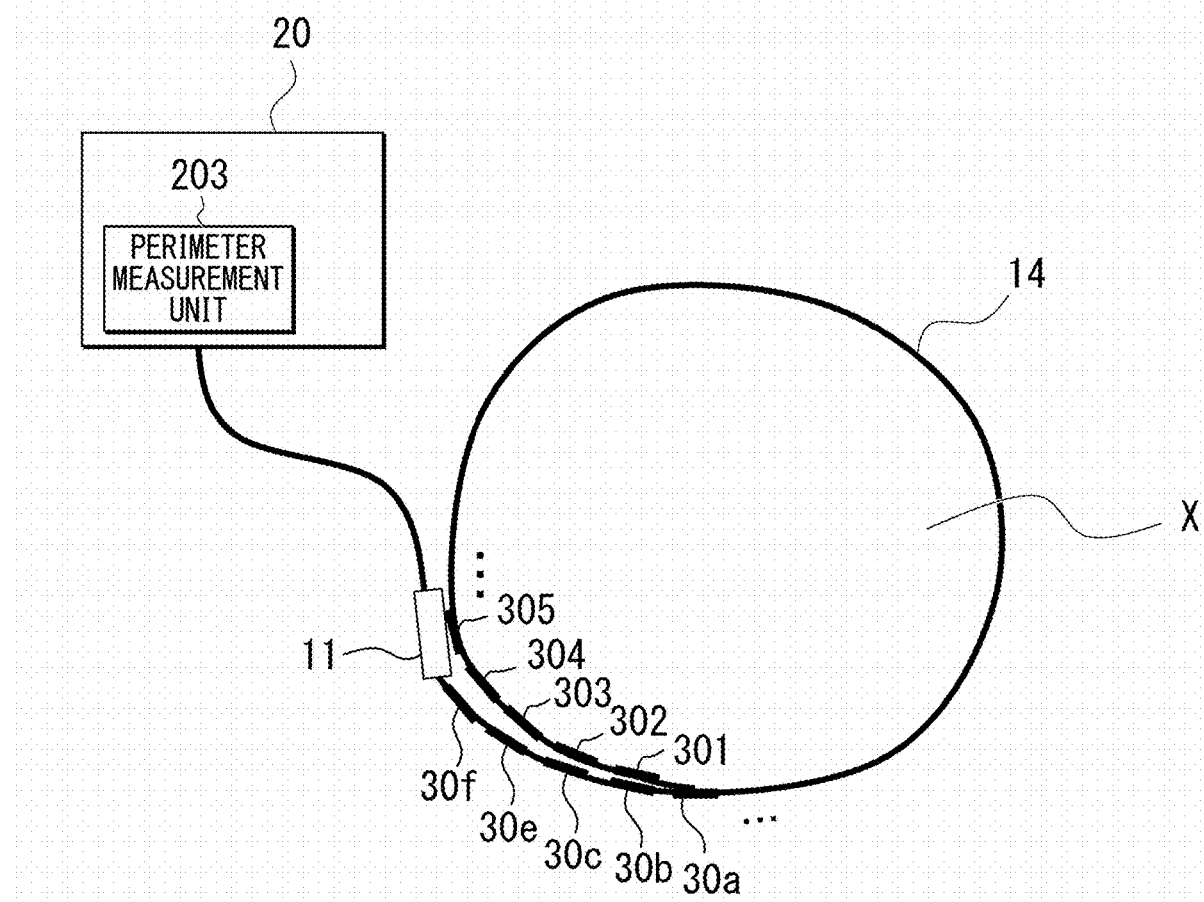
FIG. 19 is a diagram illustrating a function of a perimeter measurement unit according to the second embodiment.

FIG. 19 is a diagram illustrating a function of a perimeter measurement unit according to the second embodiment.

As illustrated in FIG. 19, the EIT measurement main body unit 20 according to this embodiment further includes a perimeter measurement unit 203. The perimeter measurement unit 203 has a function of measuring a perimeter of a measurement target portion X on the basis of a voltage signal acquired via the perimeter measurement electrode pads 301 to 30*f*. In terms of the perimeter measurement unit 203, an aspect in which a CPU 200 responsible for the overall operation of the EIT measurement main body unit 20 performs the function of the perimeter measurement unit 203 when a measurement program is executed as in the EIT measurement control unit 201 and the contour estimation unit 202 in the first embodiment may be provided.

The perimeter measurement unit 203 pre-recognizes intervals α (FIG. 18) of the perimeter measurement electrode pads 301 to 30*f* periodically pre-arranged on the measurement belt 10. The perimeter measurement unit 203 measures electrical impedance for every electrode pair in the perimeter measurement electrode pads 301 to 30*f*.

For example, because the perimeter measurement electrode pad 301 and the perimeter measurement electrode pad are in close contact with each other at the time of the state as illustrated in FIG. 19, the electrical impedance between the perimeter measurement electrode pads 301 and 30*b* is reduced on the basis of capacitance coupling of the two electrodes. Similar results are obtained even between 302 and 30*c*, 303 and 30*e*, and 304 and 30*f* which are other electrode pairs. On the other hand, because the perimeter measurement electrode pads 30*a* and 305 do not form capacitance coupling with other electrode pads, the perimeter measurement unit 203 detects high electrical impedance values for the perimeter measurement electrode pads 30*a* and 305.

Also, the interval α between the perimeter measurement electrode pads is not required to be absolutely the same as an interval between the electrode pads, and the perimeter length measurement accuracy can be improved by reducing the interval α.

Thus, the perimeter measurement unit 203 specifies a region where a position overlaps when the measurement belt 10 is wrapped from a difference of an electrical impedance value for each of pairs of the perimeter measurement electrode pads 30I to 30f and determines a perimeter of the measurement target portion X.

Because the EIT measurement device 1 can simultaneously acquire the perimeter of the measurement target portion X along with the EIT measurement, the operator of the EIT measurement device 1 can save time and trouble (see step S30 in FIG. 6) of actually and separately measuring the perimeter of the measurement target portion X using a measure or the like in the first embodiment.

Consequently, according to the EIT measurement device according to the second embodiment, it is possible to further simplify a procedure of performing EIT measurement.

Also, when the perimeter differs according to a measurement target person or a portion serving as a measurement target, for example, an aspect in which a plurality of measurement belts 10 for which a distance between electrode pads or the like changes are prepared, a measurement belt having an optimum length is selected from among the plurality of measurement belts 10, and the selected measured belt is used may be provided. Also, the measurement belt 10 may be provided with a stretchable mechanism (a rubber band or the like).

Also, the measurement belt 10 according to each embodiment is configured to have the eight electrode pads 12A to 12H and the eight strain gauges 13A to 13H periodically arranged in the longitudinal direction as described above, and content of the processes S1 to S3 in the contour estimation unit 202 has been described under the assumption that the number of arranged strain gauges 13A to 13H is eight.

However, an aspect in which the EIT measurement device 1 according to another embodiment, for example, has 16 or 32 electrode pads and 16 or 32 strain gauges may be provided. For example, when the measurement belt 10 is not provided with a stretchable mechanism, the number of electrode pads 12A to 12H in contact with the body surface of the measurement target portion X or the number of strain gauges 13A to 13H disposed in parallel to the electrode pads 12A to 12H among a plurality of electrode pads 12A to 12H or a plurality of strain gauges 13A to 13H pre-provided in the measurement belt 10 according to a size of the measurement target portion X is considered to change.

In this aspect, for example, the contour estimation unit 202 reads a coordinate position of a predetermined reference point indicating a position of a strain gauge designated for every predetermined interval at a distance of one or more strain gauges in a periodic arrangement on the measurement belt 10 from the HDD 211 and specifies the read coordinate position as initial coordinate values (first step S10).

Relative coordinate values specifying a coordinate position of a subordinate point indicating a position of any strain gauge arranged between strain gauges indicated by the reference point for a coordinate position of the reference point are calculated on the basis of the curvature data acquired via the strain gauge (second step S11).

Hereinafter, it is possible to specify the relative positional relation of each strain gauge by performing the third step S12 and the fourth step S13 described in the first embodiment.

Third Embodiment

As described above, in the relative position specifying process S1 according to the first embodiment, an EIT measurement device 1 arranges references points N13A and N13E on the x-axis and arranges reference points N13C and N13G on the y-axis orthogonal to the x-axis when virtual positions on the xy coordinates of alternately designated strain gauges (strain gauges 13A, 13C, 13E, and 13G (FIG. 2)) are provisionally determined (see FIG. 7). That is, the EIT measurement device 1 according to the first embodiment performs calculation under the assumption that four (strain gauges 13A, 13C, 13E, and 13G) of the strain gauges periodically arranged on the measurement belt 10 are constantly arranged on axes (x- and y-axes) orthogonal to each other when the measurement belt 10 is wrapped around the measurement target portion X.

However, the periodic intervals (distances P) between the strain gauges 13A to 13H periodically arranged in the measurement belt 10 are fixed and a perimeter of the measurement target portion X changes according to a physique of the measurement target person. Accordingly, some of the strain gauges 13A to 13H are not necessarily arranged on mutually orthogonal axes. Accordingly, the EIT measurement device 1 according to the first embodiment is likely to cause an error in a shape estimation result when some of the strain gauges are not located on mutually orthogonal axes.

On the other hand, the EIT measurement device 1 according to the third embodiment can precisely estimate a contour shape even when some of the strain gauges are not located on mutually orthogonal axes.

Hereinafter, the EIT measurement device 1 according to the third embodiment will be described in detail with reference to the drawings.

Figure 20:
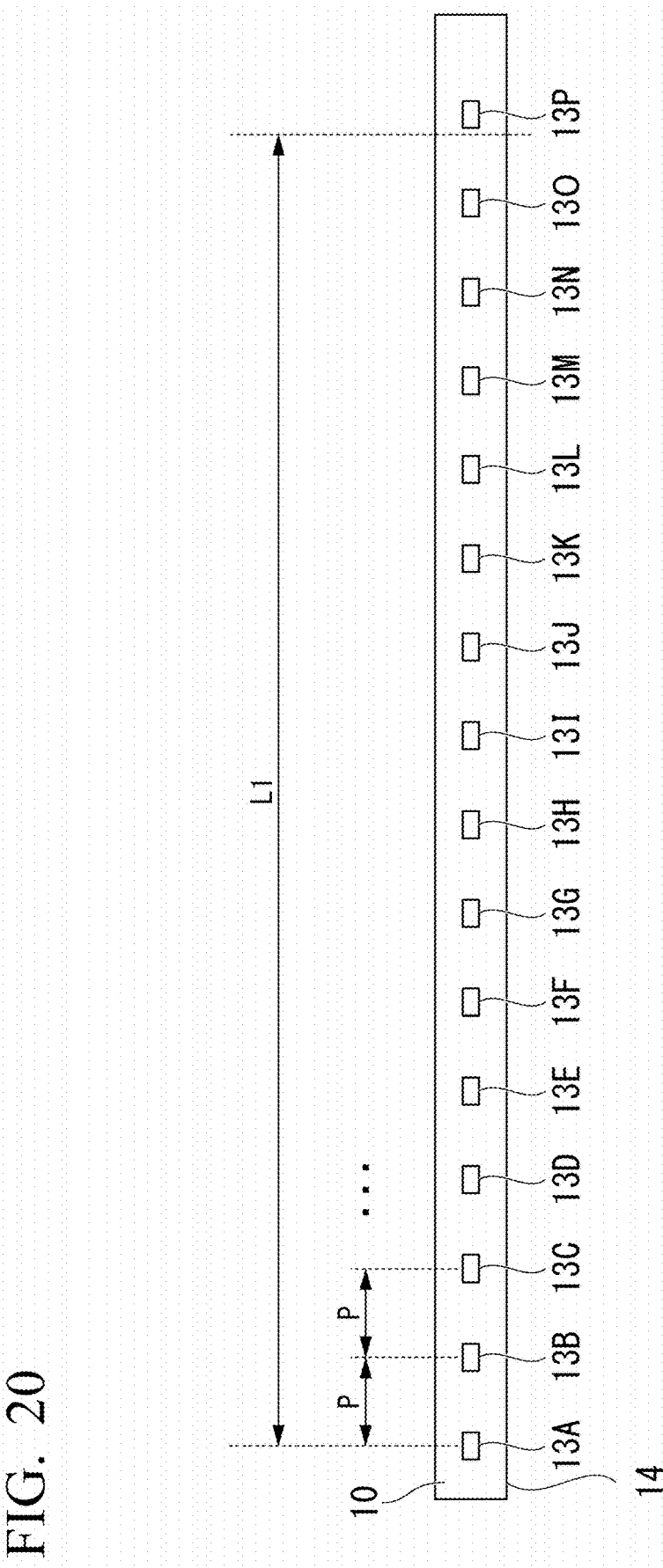
FIG. 20 is a diagram illustrating a functional configuration of a measurement belt according to a third embodiment.

FIG. 20 is a diagram illustrating a functional configuration of a measurement belt according to the third embodiment.

As illustrated in FIG. 20, in the measurement belt 10, sixteen strain gauges 13A to 13P are periodically arranged at distances P of regular intervals on a belt-shaped flexible substrate 14. Also, the notation of a measurement circuit 11 and electrode pads 12A to 12H is omitted to avoid a complexity of the drawings in FIG. 20, but the measurement circuit 11 and the electrode pads 12A to 12H are actually provided as in the first embodiment.

In the following description, the case in which the measurement belt 10 is wrapped around a chest portion of a chest circumference L1 serving as a measurement target object X will be described. Here, the chest circumference L1 has a length shorter than a length from the strain gauge 13A arranged at one end of the measurement belt 10 to the strain gauge 13P arranged at the other end (see FIG. 20).

Figure 21:
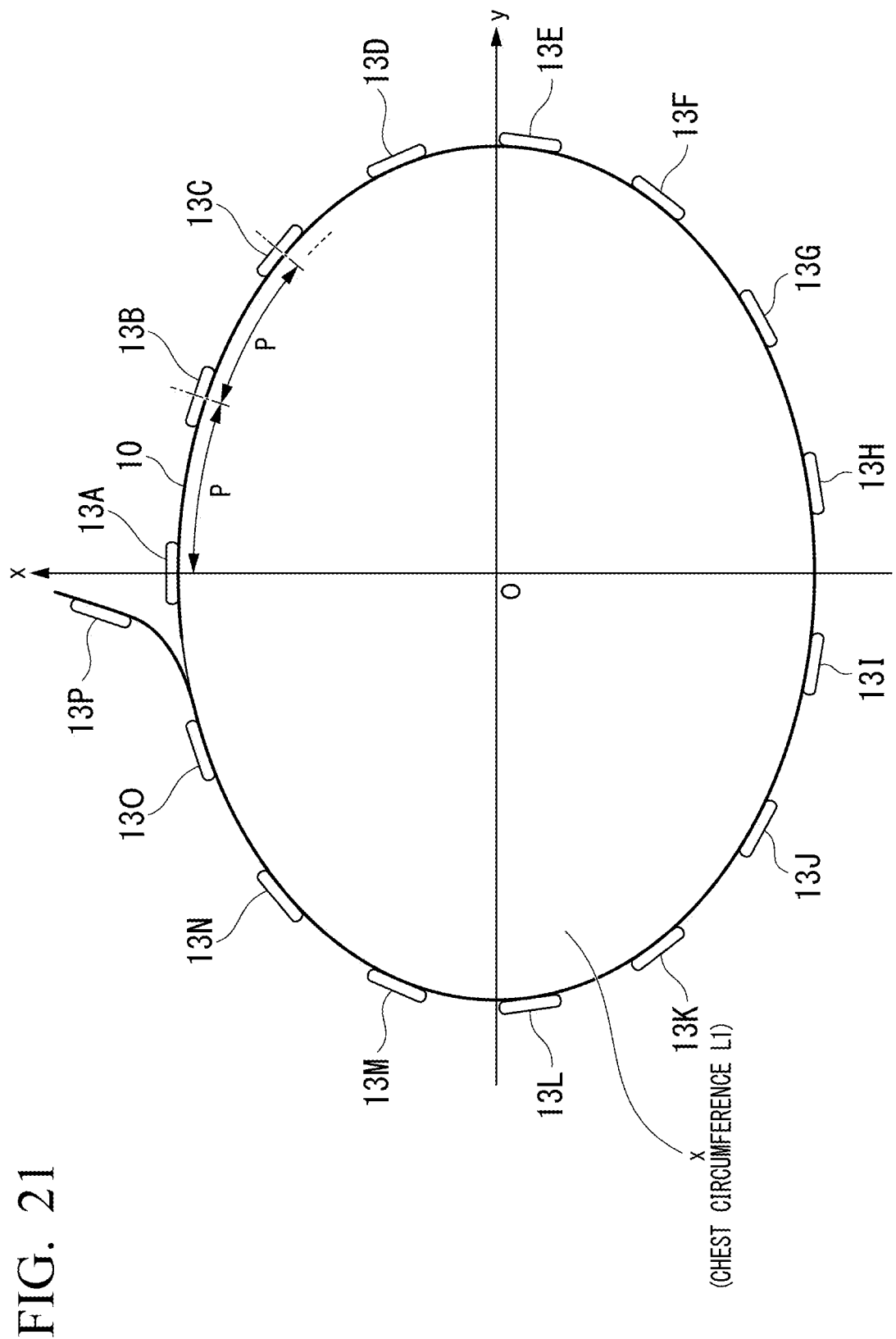
FIG. 21 is a diagram illustrating a state in which the measurement belt is wrapped according to the third embodiment.

FIG. 21 is a diagram illustrating a state in which the measurement belt is wrapped according to the third embodiment.

As illustrated in FIG. 21, the measurement belt 10 is wrapped while the strain gauge 13A arranged at the end of the measurement belt 10 is aligned with a center (sternum body) of the chest portion of the measurement target object X. In this case, because an integer multiple (16 times in this embodiment) of an interval (distance P) for each of the strain gauges 13A to 13P does not match the chest circumference L1, strain gauges other than the strain gauge 13A are arranged at positions shifted from the x-axis and the y-axis when the x-axis is defined as a symmetric axis in a front-back direction of the measurement target object X (measurement target person) and the y-axis is defined as a symmetric axis in a left-right direction.

Accordingly, as in the EIT measurement device 1 according to the first embodiment, an error occurs when a contour (thorax) estimation process is performed under the assumption that four of the strain gauges are constantly arranged on the x-axis and the y-axis which are mutually orthogonal.

Therefore, even in this case, the contour estimation unit 202 according to this embodiment executes the following process to enable the contour of the measurement target object X to be estimated with high precision.

Figure 22:
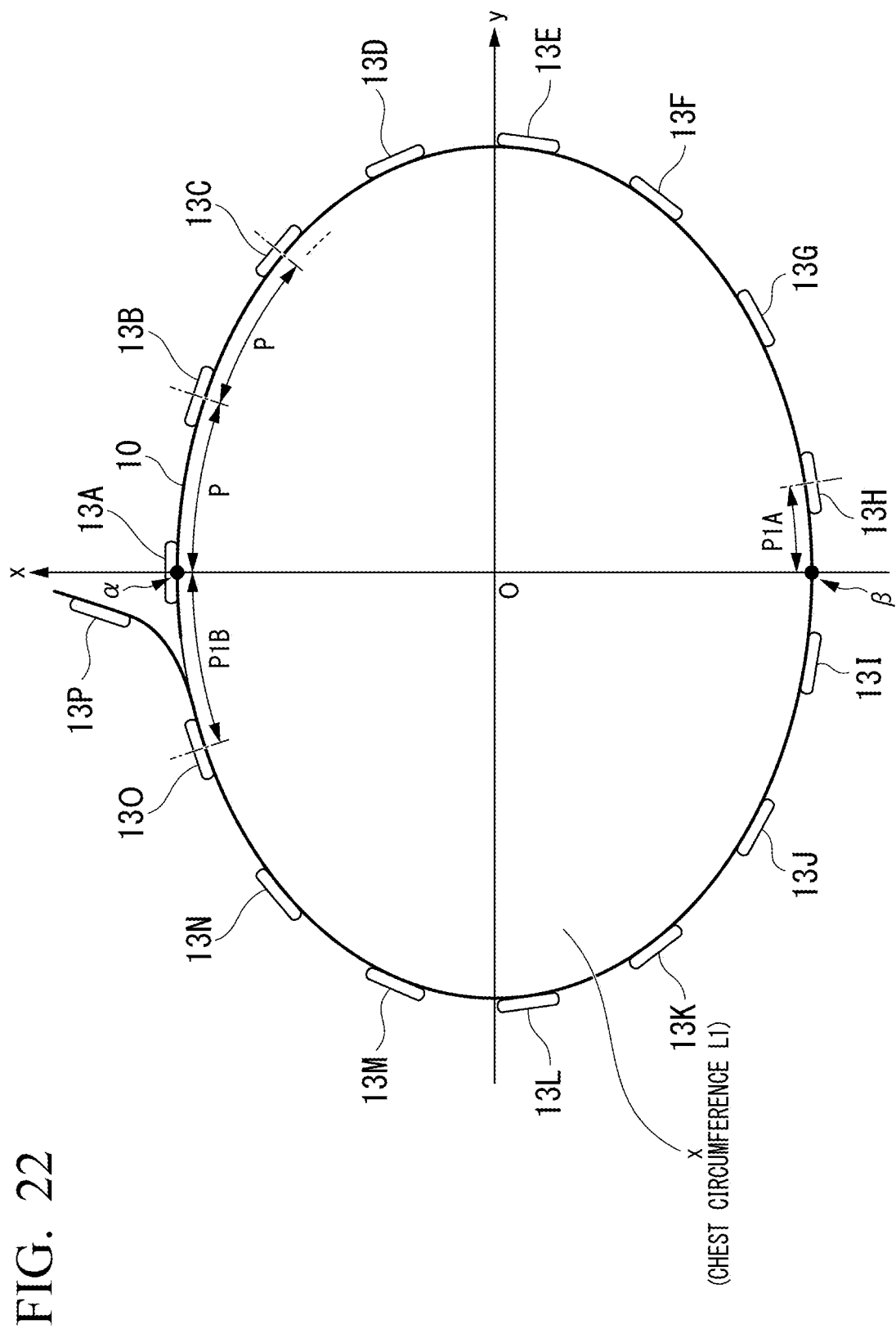
FIG. 22 is a diagram illustrating a function of a contour estimation unit according to the third embodiment.

FIG. 22 is a diagram illustrating a function of a contour estimation unit according to the third embodiment.

An operator who handles the EIT device 1 according to this embodiment first arranges the strain gauge (the strain gauge 13A in this embodiment) arranged at one end side of the measurement belt 10 at the center (on the sternum body) of the chest portion of the measurement target object X (measurement target person) as a first base point α.

Next, the operator wraps the measurement belt 10 around the measurement target object X while the first base point α in the measurement belt 10 is fixed on the sternum body of the measurement target object X.

When the chest circumference L1 of the measurement target object X does not match an integer multiple of a distance P as described above, the strain gauges 13A to 13P are arranged to be asymmetrical to the measurement target object X. Therefore, as illustrated in FIG. 22, no strain gauge is arranged at the center (spine protrusion) of the back of the measurement target object X. Therefore, the operator specifies a position on the measurement belt 10 matching a position of the spine protrusion of the measurement target object X as a second base point β. Specifically, the operator specifies a pair of strain gauges (strain gauges 13H and 13I in this embodiment) arranged with interleaving the spine protrusion of the measurement target object X among the strain gauges 13A to 13P. Further, the operator measures a distance P1A from the strain gauge (strain gauge 13H) to the spine protrusion (second base point β) of the measurement target object X.

Subsequently, when the measurement belt 10 is wrapped around the measurement target object X, the operator specifies a position of the strain gauge (the strain gauge 13O in this embodiment) closest to the first base point α among strain gauges in contact with the measurement target object X at the other end of the measurement belt 10. Specifically, the operator measures a distance P1B from the strain gauge 13O to the first base point α. Thereby, it is possible to specify a positional relation between strain gauges 13A to 13O on the measurement belt 10, the first base point α, and the second base point β which are prescribed separately.

Also, in this case, the strain gauge 13P arranged in the remaining portion of the other end of the measurement belt 10 is not used in a process of estimating a shape of a contour.

The contour estimation unit 202 of the EIT measurement device 1 according to this embodiment receives inputs of the distance P1A from the strain gauge 13H to the second base point β and the distance P1B from the strain gauge 13O to the first base point α measured by the operator. The operator manipulates the manipulation input unit 212 of the EIT measurement device 1and inputs strain gauge identification information (information for specifying the strain gauges 13H and 13O) and information indicating the measured distances P1A and P1B to the EIT measurement device 1.

FIGS. 23 to 27 are first to fifth diagrams illustrating specific content of a process of the contour estimation unit according to the third embodiment.

Next, a process in which the contour estimation unit 202 according to this embodiment estimates a contour shape of a fault plane of the measurement target portion X will be specifically described.

(In Terms of Relative Position Specifying Process)

As in the first embodiment, the contour estimation unit 202 specifies the relative positional relation for each of the strain gauges 13A to 13O in the relative position specifying process S1.

Figure 23:
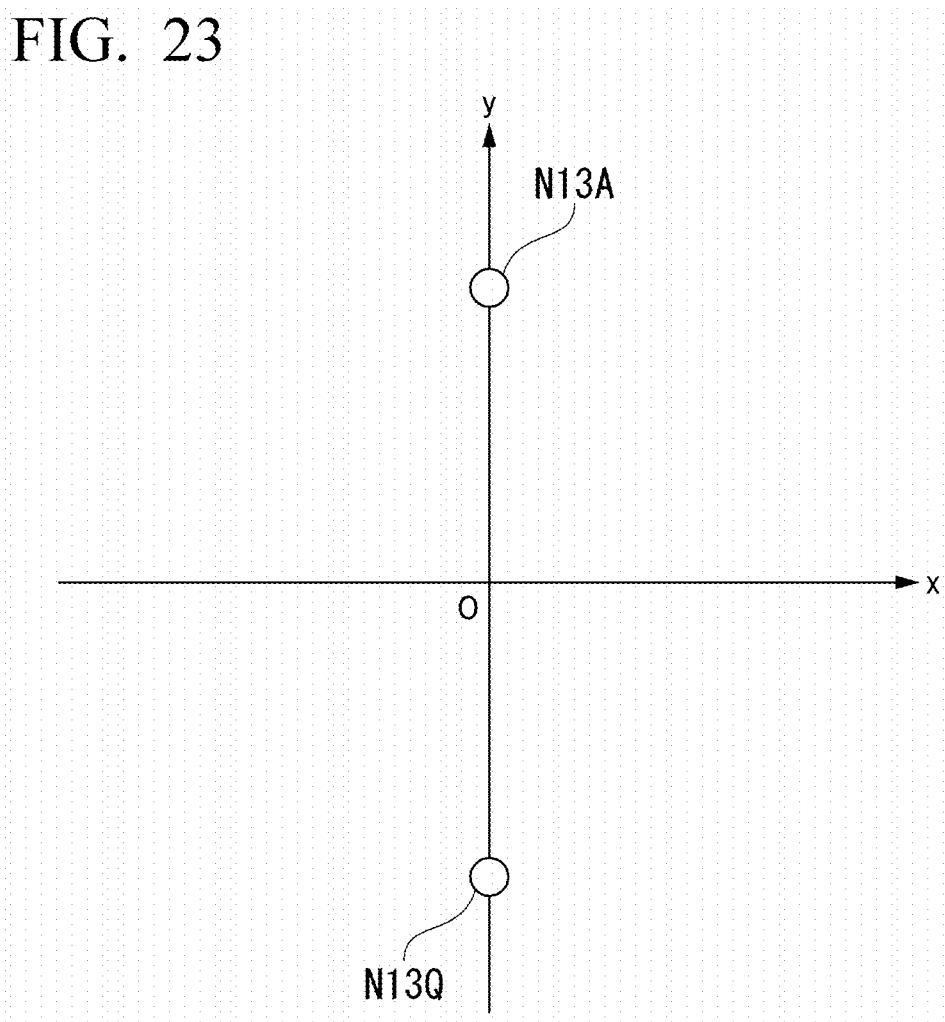
FIG. 23 is a first diagram illustrating specific content of a process of the contour estimation unit according to the third embodiment.

Specifically, as illustrated in FIG. 23, the contour estimation unit 202 first sets predetermined xy coordinates and provisionally determines a reference point N13A indicating a coordinate position on the xy coordinates for the strain gauge 13A on the xy coordinates by arranging the strain gauge 13A arranged at the first base point α on the y-axis in the first step S10 (FIG. 6).

Next, the contour estimation unit 202 provisionally determines a reference point on the xy coordinates corresponding to a strain gauge arranged at the second base point β. Here, no strain gauge is actually located on the second base point β (see FIG. 22). Accordingly, the contour estimation unit 202 regards a virtual strain gauge 13Q as being located at the second base point β and provisionally determines a reference point N13Q indicating a position of the virtual strain gauge 13Q on the y-axis. That is, both of the strain gauge 13A arranged on the first reference point α and the strain gauge 13Q (virtually) arranged on the second reference point β are arranged on the symmetric axis along the front-back direction of the measurement target object X, that is, the symmetric axis which connects the sternum body and the spine protrusion. Accordingly, the contour estimation unit 202 provisionally determines the position on the xy coordinates by designating that the reference point N13A and the reference point N13Q are located on the axis (y-axis) corresponding to the symmetric axis along the front-back direction of the measurement target object X.

As described above, in the first step S10 of the relative position specifying process S1, the contour estimation unit 202 according to this embodiment specifies a coordinate position of a reference point indicating the strain gauge 13A arranged on the symmetric axis of the measurement target object X (an axis connecting the sternum body and the spine protrusion) among a plurality of strain gauges 13A to 13P as predetermined initial coordinate values. In addition, the contour estimation unit 202 regards the virtual strain gauge 13Q as being arranged on the second base point β and executes the relative position specifying process S1 when no strain gauge is arranged at a position (second base point β) arranged on the above-described symmetric axis of the measurement target object X in the measurement belt 10 around which the measurement target object X is wrapped.

Here, the contour estimation unit 202 specifies coordinate positions of an upper reference point N13A and a lower reference point N13Q on the y-axis around the origin O. Specifically, the contour estimation unit 202 reads initial coordinate values pre-stored for each of the reference points N13A and N13Q from the HDD 211 to set the initial coordinate values on coordinates around the origin O. For example, initial coordinate values (0 [cm], 50 [cm]) for the reference point N13A, initial coordinate values (0 [cm], −50 [cm]) for the reference point N13Q, etc. are stored in the HDD 211.

Next, in the second step S11 (FIG. 6), the contour estimation unit 202 specifies a relative positional relation between the reference points N13A and N13Q and subordinate points indicating positions on the xy coordinates of two strain gauges arranged at both sides of the strain gauges 13A and 13Q corresponding to the reference points N13A and N13Q.

Also, the contour estimation unit 202 according to this embodiment defines a combination of one reference point (for example, the reference point N13A) and subordinate points (for example, N13B1, N13C1, N13D1, etc.) continuously arranged in series at both sides of the reference point associated through the above-described relative positional relation as a bundle of one set.

Here, strain gauges arranged to be adjacent to both sides of the strain gauge 13A are a strain gauge 13B and a strain gauge 13O (see FIGS. 21 and 22). In this case, the contour estimation unit 202 specifies positions on the xy coordinates of subordinate points N13B1 and N13O1 by designating a subordinate point indicating a relative position of the strain gauge 13B based on the position (xa, ya) of the reference point N13A as the subordinate point N13B1 and designating a subordinate point indicating a relative position of the strain gauge 13O based on the position of the reference point N13A as the subordinate point N13O1.

Also, strain gauges arranged to be adjacent to both sides of a virtual strain gauge 13Q are a strain gauge 13H and a strain gauge 13I (see FIGS. 21 and 22). In this case, the contour estimation unit 202 specifies positions on the xy coordinates of subordinate points N13H2 and N13I2 by designating a subordinate point indicating a relative position of the strain gauge 13H based on the position (xq, yq) of the reference point N13Q as the subordinate point N13H2 and designating a subordinate point indicating a relative position of the strain gauge 13I based on the position of the reference point N13Q as the subordinate point N13I2.

A process in which the contour estimation unit 202 according to this embodiment specifies a relative positional relation of subordinate points for the reference points N13A and N13Q is similar to that of the first embodiment (see FIG. 8).

However, the contour estimation unit 202 uses the fact that a distance from the reference point N13A to the subordinate point N13O1 is a distance P1B (<distance P) input by the operator when the relative position of the subordinate point N13O1 for the reference point N13A is specified. Specifically, the contour estimation unit 202 sets a point at which an integrated amount of a micro distance dP from the reference point N13A becomes a distance P1B as a subordinate point N13O1 in FIG. 8. Also, the contour estimation unit 202 uses the fact that a distance from the reference point N13A to the subordinate point N13B1 is a distance P when the relative position of the subordinate point N13B1 for the reference point N13A is specified.

Likewise, the contour estimation unit 202 specifies the relative position from the subordinate point N13H2 using the fact that a distance from the reference point N13Q to the subordinate point N13H2 is a distance P1A (<distance P) input by the operator. Specifically, the contour estimation unit 202 sets a point at which an integrated amount of a micro distance dP from the reference point N13Q becomes the distance P1A as the subordinate point N13H2 in FIG. 8.

Further, the contour estimation unit 202 specifies the relative position from the subordinate point N13I2 using the fact that a distance from the reference point N13Q to the subordinate point N13I2 is a distance (P-P1A). Specifically, the contour estimation unit 202 sets a point at which an integrated amount of a micro distance dP from the reference point N13Q becomes the distance (P-P1A) as the subordinate point N13I2 in FIG. 8.

Also, in the above-described case, the contour estimation unit 202 according to this embodiment specifies relative positions of the subordinate points N13H2 and N13I2 for the reference point N13Q under the assumption that the curvature acquired by the virtual strain gauge 13Q arranged at the second base point β is zero (a curvature radius is infinite).

Figure 24:
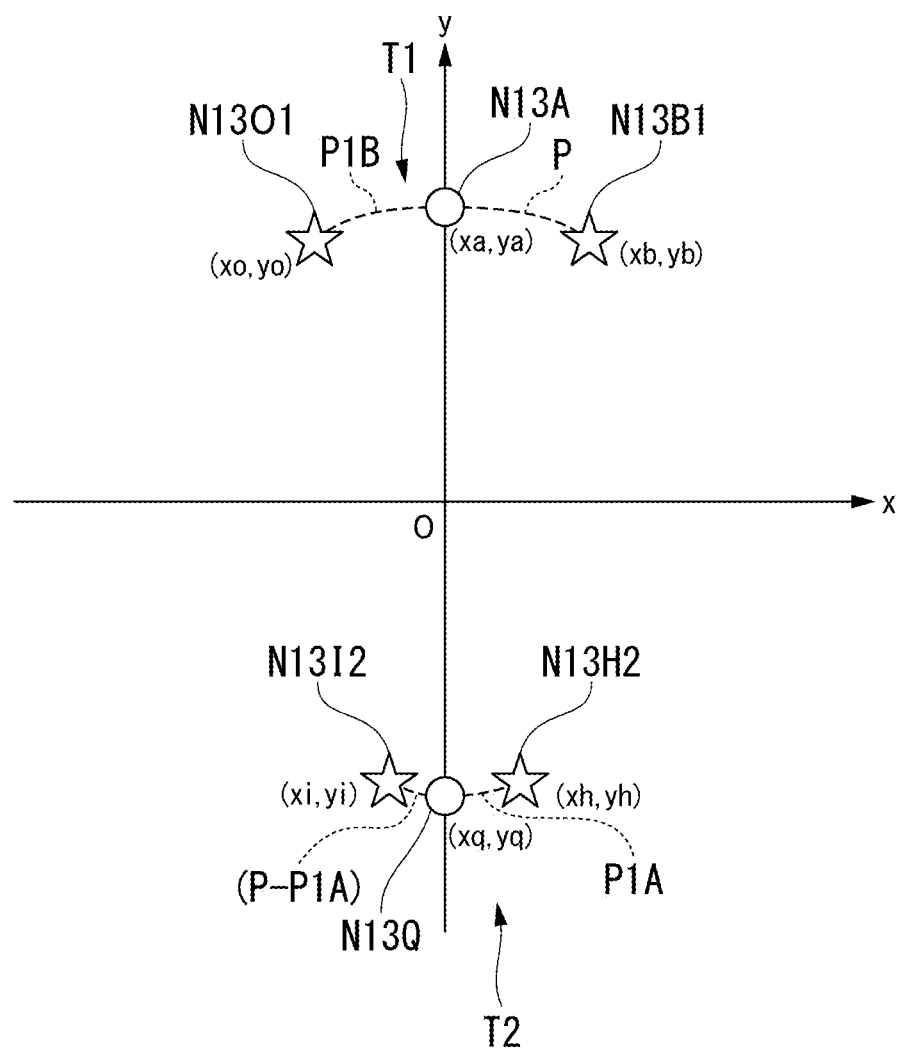
FIG. 24 is a second diagram illustrating specific content of a process of the contour estimation unit according to the third embodiment.
Figure 25:
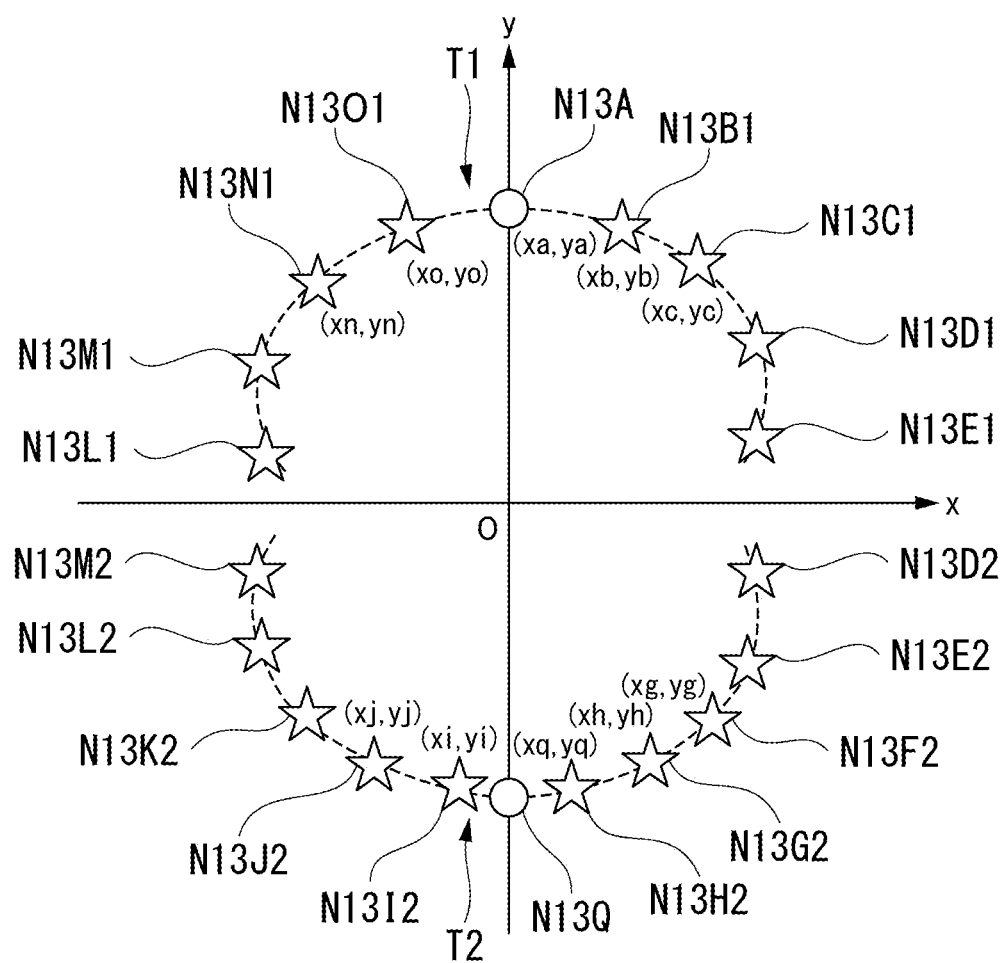
FIG. 25 is a third diagram illustrating specific content of a process of the contour estimation unit according to the third embodiment.

FIG. 24 illustrates a state in which the contour estimation unit 202 specifies positions of subordinate points adjacent to reference points N13A and N13Q on the basis of the reference points N13A and N13Q through the above process.

As illustrated in FIG. 24, the contour estimation unit 202 specifies a relative position (xb, yb) of the subordinate point N13B1 and a relative position (xo, yo) of the subordinate point N13O1 based on a position (xa, ya) of the reference point N13A. Likewise, the contour estimation unit 202 specifies a relative position (xh, yh) of the subordinate point N13H2 and a relative position (xi, yi) of the subordinate point N13I2 based on a position (xq, yq) of the reference point N13Q.

Further, the contour estimation unit 202 according to this embodiment specifies a position of a subordinate point further subordinate to each subordinate point by iterating the process illustrated in FIG. 8. For example, the contour estimation unit 202 specifies a position (xc, yc) of a subordinate point N13C1 (a subordinate point corresponding to the strain gauge 13C) adjacent to the subordinate point N13B1 based on a position (xb, yb) of the subordinate point N13B1. Likewise, the contour estimation unit 202 specifies a position (xn, yn) of a subordinate point N13N1 (a subordinate point corresponding to the strain gauge 13N) adjacent to the subordinate point N13O1 based on a position (xo, yo) of the subordinate point N13O1.

The contour estimation unit 202 specifies a position of each of subordinate points N13B1 to N13E1 which are subordinate in series at one side of the reference point N13A and a position of each of subordinate points N13L1 to N13O1 which are subordinate in series at the other side of the reference point N13A by iterating the above-described process. Thereby, a position of the bundle T1 around the reference point N13A is provisionally determined (see FIG. 25).

Likewise, the contour estimation unit 202 specifies a position (xg, yg) of a subordinate point N13G2 (a subordinate point corresponding to a strain gauge 13G) adjacent to the subordinate point N13H2 based on a position (xh, yh) of the subordinate point N13H2. Likewise, the contour estimation unit 202 specifies a position (xj, yj) of a subordinate point N13J2 (a subordinate point corresponding to a strain gauge 13J) adjacent to the subordinate point N13I2 based on a position (xi, yi) of the subordinate point N13I2.

The contour estimation unit 202 specifies a position of each of subordinate points N13D2 to N13H2 which are subordinate in series at one side of the reference point N13Q and a position of each of subordinate points N13I2 to N13M2 which are subordinate in series at the other side of the reference point N13Q by iterating the above-described process. Thereby, a position of the bundle T2 around the reference point N13Q is provisionally determined (see FIG. 25).

Here, as described above, subordinate points N13D1 and N13E1 belonging to the bundle T1 are points virtually indicating positions of the strain gauge 13D and the strain gauge 13E arranged on the measurement belt 10. On the other hand, subordinate points N13D2 and N13E2 belonging to the bundle T2 are also points virtually indicating positions of the strain gauge 13D and the strain gauge 13E arranged on the measurement belt 10.

That is, two subordinate points N13D1 and N13D2 belonging to different bundles (T1 or T2) indicate the position of the same strain gauge 13D. Also, two subordinate points N13E1 and N13E2 belonging to a different bundle indicate the position of the same strain gauge 13E. Likewise, two subordinate points N13L1 and N13L2 belonging to different bundles indicate the position of the same strain gauge 13L. Two subordinate points N13M1 and N13M2 belonging to different bundles indicate the position of the same strain gauge 13M.

Accordingly, in this case, it is considered that the subordinate points N13D1 and N13D2 are displayed at the same coordinate position, the subordinate points N13E1 and N13E2 are displayed at the same coordinate position, the subordinate points N13L1 and N13L2 are displayed at the same coordinate position, and the subordinate points N13M1 and N13M2 are displayed at the same coordinate position.

Consequently, the contour estimation unit 202 performs a process of moving positions on the xy coordinates by changing coordinate positions of points (reference points and subordinate points) included in the bundles T1 and T2 so that positions of subordinate points N13D1, N13E1, N13L1 and N13M1 included in the bundle T1 match positions of subordinate points N13D2, N13E2, N13L2, and N13M2 included in the bundle T2 in the third step S12 (FIG. 6). At this time, the contour estimation unit 202 changes (moves in parallel) coordinate positions of points while relative position relations between reference points and subordinate points included in the bundle T1 and the bundle T2 are maintained.

Figure 26:
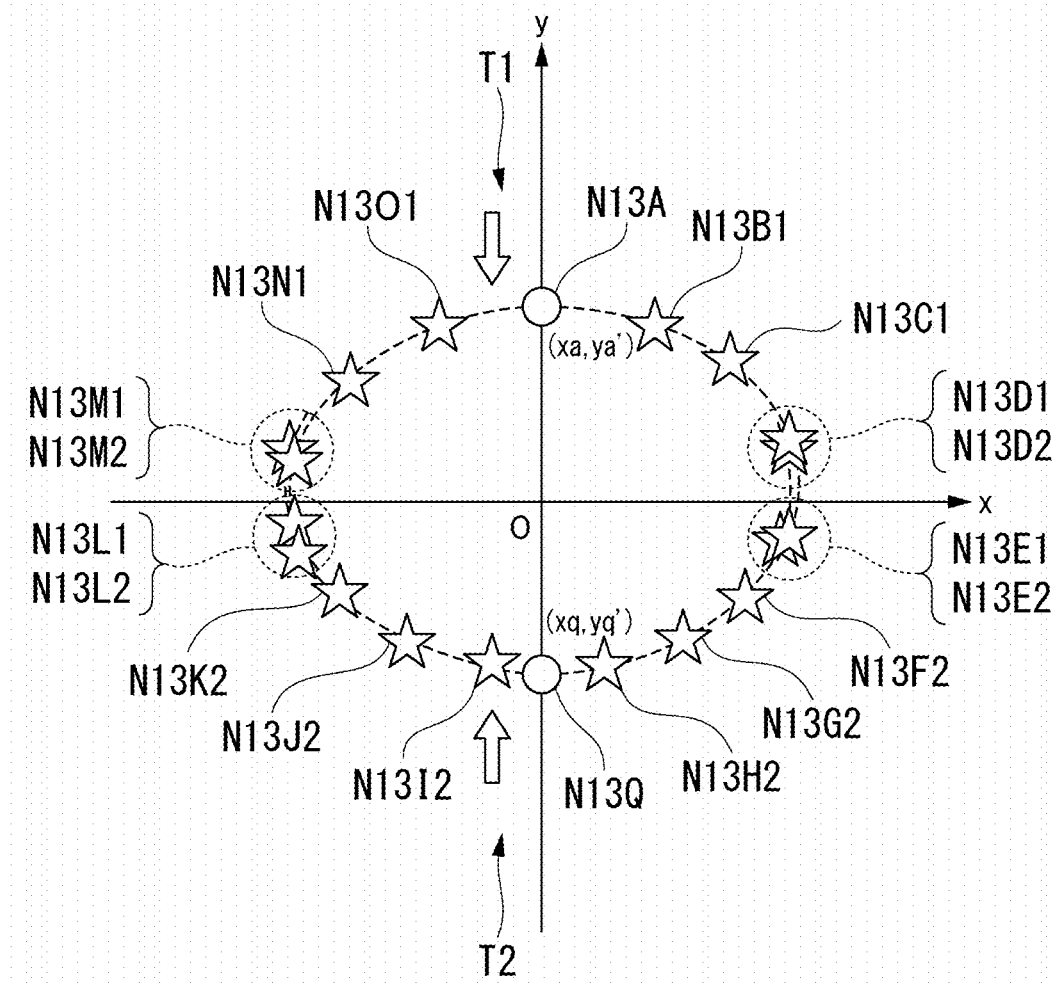
FIG. 26 is a fourth diagram illustrating specific content of a process of the contour estimation unit according to the third embodiment.

FIG. 26 illustrates a process in which the contour estimation unit 202 moves coordinate positions of points (reference points and subordinate points) included in the bundles T1 and T2 in parallel.

At this time, the contour estimation unit 202 moves the coordinate positions to positions at which a sum of errors of coordinate positions of the subordinate points N13D1 and N13D2 indicating the position of the same strain gauge 13D, coordinate positions of the subordinate points N13E1 and N13E2 indicating the position of the same strain gauge 13E, coordinate positions of the subordinate points N13L1 and N13L2 indicating the position of the same strain gauge 13L, and coordinate positions of the subordinate points N13M1 and N13M2 indicating the position of the same strain gauge 13M is minimized.

Specifically, the contour estimation unit 202 performs a process of changing coordinate positions so that the bundle T1 is moved in parallel in a −y direction along the y-axis. Here, the contour estimation unit 202 changes coordinates (xa, ya) of the reference point N13A of the bundle T1 to coordinate (xa, ya') (ya>ya'). Likewise, the contour estimation unit 202 performs a process of changing coordinate positions so that the bundle T2 is moved in parallel in a +y direction along the y-axis. Here, the contour estimation unit 202 changes coordinates (xq, yq) of the reference point N13Q of the bundle T2 to coordinate (xq, yq') (yq<yq') As illustrated in FIG. 26, final positions of the bundles T1 and T2 are specified at positions at which a sum of errors of positions in a pair of N13D1 and N13D2, a pair of N13E1 and N13E2, a pair of N13L1 and N13L2, and a pair of N13M1 and N13M2 which are pairs of subordinate points belonging to a region in which the bundle T1 and the bundle T2 overlap is minimized.

Subsequently, the contour estimation unit 202 specifies a center point between subordinate points belonging to the bundles T1 and T2 indicating the same strain gauge as a point indicating a position of the strain gauge (step S13 (FIG. 16)).

Figure 27:
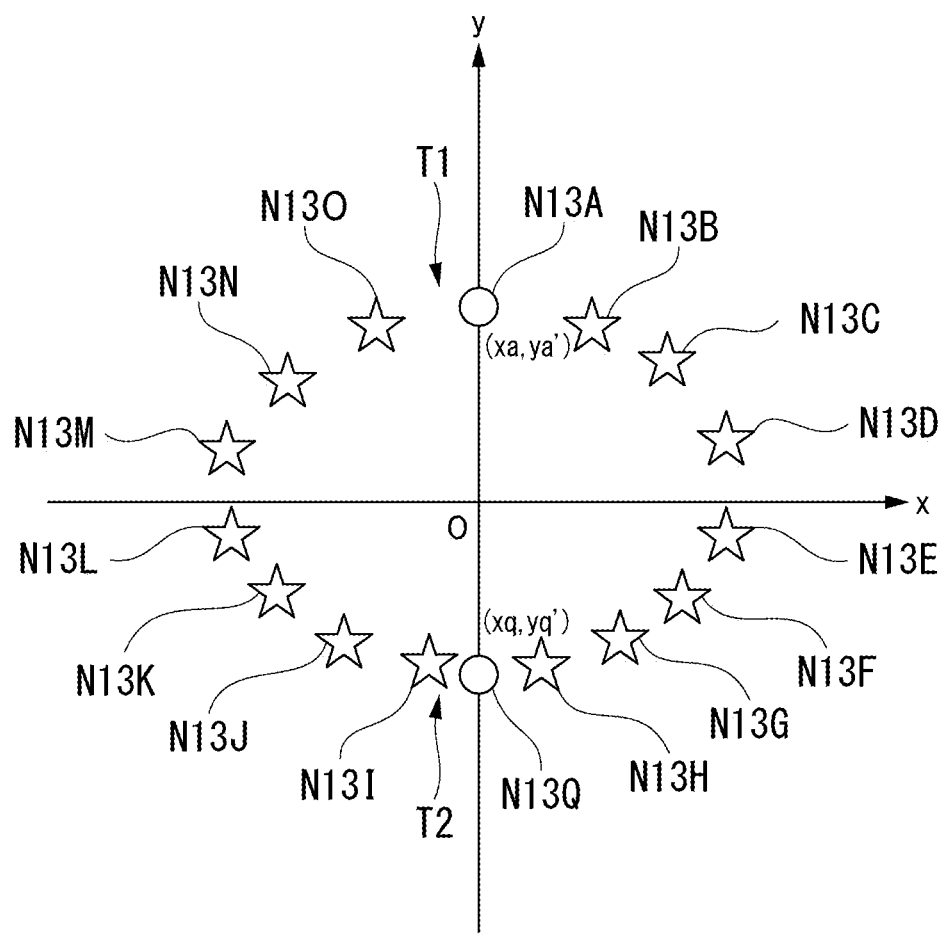
FIG. 27 is a fifth diagram illustrating specific content of a process of the contour estimation unit according to the third embodiment.

FIG. 27 illustrates a state immediately after the above-described fourth step S13 is completed. Also, in FIG. 27, the subordinate points N13B to N13O indicate positions on the xy coordinates corresponding to the strain gauges 13B to 13O. Here, the subordinate points N13B, N13C, N13N, and N13O have the same positions as those of the subordinate points N13B1, N13C1, N13N1, and N13O1 belonging to the bundle T1, respectively. Also, the subordinate points N13F, N13G, N13H, N13I, N13J, and N13K have the same positions as those of the subordinate points N13F2, N13G2, N13H2, N13I2, N13J2, and N13K2 belonging to the bundle T2, respectively. Subordinate points N13D, N13E, N13L, and N13M belonging to a region in which the bundles T1 and T2 overlap become a center position between the subordinate points N13D1 and N13D2, a center position between the subordinate points N13E1 and N13E2, a center position between the subordinate points N13L1 and N13L2, and a center position between the subordinate points N13M1 and N13M2 belonging to the bundles T1 and T2, respectively.

The contour estimation unit 202 specifies positions on the xy coordinates of fifteen strain gauges 13A to 13O (and a virtual strain gauge 13Q) through the processes of the above first step S10 to the fourth step S13.

Also, because the shape specifying process S2 and the size specifying process S3 subsequent to the relative position specifying process S1 are similar to those of the first embodiment, description thereof will be omitted.

(Effects)

As described above, the contour estimation unit 202 according to the third embodiment specifies a coordinate position of the strain gauge 13A arranged at a predetermined position (first base point α) on a symmetric axis (an axis which connects the sternum body and the spine protrusion) of the measurement target object X among a plurality of strain gauges 13A to 13P as predetermined initial coordinate values in the first step S10 of the relative position specifying process S1. In this case, the initial coordinate values become a predetermined position on the axis (y-axis) corresponding to the symmetric axis of the above-described measurement target object X.

Thereby, it is possible to precisely estimate a contour when the relative position specifying process S1 is executed as a constraint condition where the strain gauge 13A is arranged on the axis corresponding to the symmetric axis of the measurement target object X.

Also, the contour estimation unit 202 according to the third embodiment regards a virtual strain gauge 13Q as being arranged at a position on the symmetric axis of the measurement target object X and executes the relative position specifying process S1 when no strain gauge is arranged at a position (second base point β) on the symmetric axis of the measurement target object X on the measurement belt 10 wrapped around the measurement target object X. That is, the contour estimation unit 202 specifies a coordinate position of the virtual strain gauge 13Q (reference point N13Q) arranged at a position (second base point β) on the symmetric axis of the measurement target object X as predetermined initial coordinate values. In this case, the initial coordinate values also become a predetermined position on an axis (y-axis) corresponding to the symmetric axis of the measurement target object X.

Thereby, the contour estimation unit 202 executes the relative position specifying process S1 as a constraint condition where the virtual strain gauge 13Q is arranged on the axis corresponding to the symmetric axis of the measurement target object X. Thereby, even when no strain gauge is arranged on the symmetric axis of the measurement target object X if the measurement belt 10 is wrapped around the measurement target object X, it is possible to precisely estimate a contour.

Further, the contour estimation unit 202 separately acquires distances (distances P1A and P1B) between each of a plurality of strain gauges 13A to 13P arranged on the wrapped measurement belt 10 and the first base point α and between each of the plurality of strain gauges 13A to 13P and the second base point β. Using the acquired distances, the contour estimation unit 202 can precisely calculate relative coordinate values indicating a coordinate position of each subordinate point for coordinate positions of the reference points N13A and N13Q (for example, relative coordinate values of the subordinate points N13H2 and N13I2 for the reference point N13Q) in the second step S11.

Although the EIT measurement device 1 according to the third embodiment has been described in detail, a specific aspect of the EIT measurement device 1 according to this embodiment is not limited to the above description, but various design changes and modifications, etc. can be made without departing from the subject matter.

Figure 28:
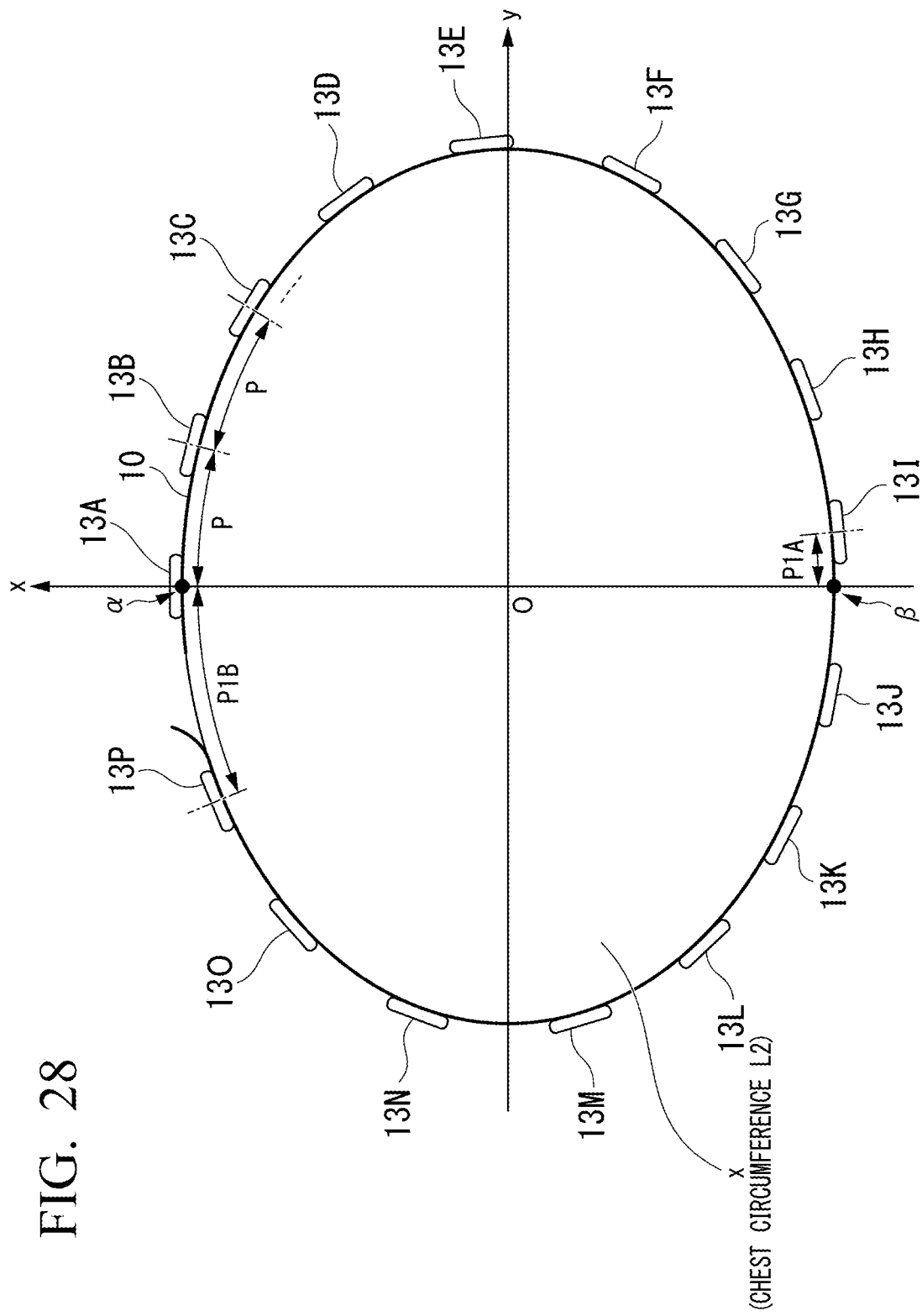
FIG. 28 is a diagram illustrating a state in which a measurement belt is wrapped according to a modified example of the third embodiment.

FIG. 28 is a diagram illustrating a state in which a measurement belt according to a modified example of the third embodiment is wrapped.

FIG. 28 illustrates the case in which the measurement belt 10 is wrapped around the chest portion of the chest circumference L2 serving as the measurement target object X. Here, a length of the chest circumference L2 is longer than a length from the strain gauge 13A arranged at one end of the measurement belt 10 to the strain gauge 13P arranged on the other end.

Even in this case, the measurement belt 10 is wrapped while the strain gauge 13A arranged at the end of the measurement belt 10 is aligned with a center (sternum body) of the chest portion of the measurement target object X. In this case, because an integer multiple (16 times in this embodiment) of an interval (distance P) for each of the strain gauges 13A to 13P does not match the chest circumference L2, strain gauges other than the strain gauge 13A are arranged at positions shifted from the x-axis and the y-axis when the x-axis is defined as a symmetric axis along a front-back direction of the measurement target object X (measurement target person) and the y-axis is defined as a symmetric axis along a left-right direction.

Accordingly, as in the EIT measurement device 1 according to the first embodiment, an error occurs when a contour (thorax) estimation process is performed under the assumption that four of the strain gauges are constantly arranged on the x-axis and the y-axis which are mutually orthogonal.

Even in this case, the operator specifies a position on the measurement belt 10 matching a position of the spine protrusion of the measurement target object X as a second base point β. Specifically, the operator specifies a pair of strain gauges (strain gauges 13I and 13J in this embodiment) arranged with interleaving the spine protrusion of the measurement target object X among the strain gauges 13A to 13P. Further, the operator measures a distance P1A from the strain gauge (strain gauge 13I) to the spine protrusion (second base point β) of the measurement target object X.

Subsequently, when the measurement belt 10 is wrapped around the measurement target object X, the operator specifies a position of the strain gauge (the strain gauge 13P in this embodiment) closest to the first base point α among strain gauges in contact with the measurement target object X at the other end side of the measurement belt 10. Specifically, the operator measures a distance P1B from the strain gauge 13P to the first base point α. Thereby, it is possible to specify a positional relation between the strain gauges 13A to 13P on the measurement belt 10 and the first base point α and the second base point β which are prescribed separately.

Hereinafter, it is possible to estimate a shape of a contour of the measurement target object X by executing a process similar to the process described in the third embodiment.

Therefore, it is possible to cope with a situation in one measurement belt 10 even when the chest circumference (chest circumference L2) of the measurement target object X is large. Thereby, it is possible to reduce the cost of the device because it is unnecessary to prepare a plurality of various types of measurement belts according to a physique of the measurement target object X (measurement target person).

Also, the case in which the operator measures a distance (distance P1A or P1B) from the first base point α or the second base point β to an adjacent strain gauge using the EIT measurement device 1 according to the third embodiment has been described.

However, an aspect in which the EIT measurement device 1 according to a modified example of the third embodiment automatically acquires the above-described distances P1A and P1B may be provided.

For example, the EIT measurement device 1 according to the modified example may include electrode pads periodically arranged at intervals more dense than intervals (distances P) at which the strain gauges 13A to 13P are arranged on the measurement belt 10. In this case, the EIT measurement device 1 acquires electrical impedance occurring between the periodically arranged electrode pads.

The EIT measurement device 1 detects a range in which the measurement belt 10 wrapped around the measurement target object X is in close contact with the measurement target object X on the basis of a change in the electrical impedance occurring between the periodically arranged electrode pads. Here, the impedance between the above-described electrode pads changes according to whether the measurement target object X which is a living body is in close contact with the electrode pad.

Thereby, the EIT measurement device 1 can automatically specify the strain gauge of the other end side arranged to be adjacent to the strain gauge (strain gauge 13A) of one end side and a distance P1B from the strain gauge of the other end side on the basis of a relative positional relation between the electrode pads in close contact with the measurement target object X and the strain gauges 13A to 13P.

Further, the EIT measurement device may specify a position of the second base point β on the measurement belt 10 by detecting unique electrical impedance occurring between electrode pads arranged at a spine protrusion portion of the measurement target object X among the above-described periodically arranged electrode pads. Here, because the above-described electrode pad and a bone within the living body are in close contact in the spine protrusion portion of the measurement target object X, different unique electrical impedance is shown from electrode pads in contact with another portion of the measurement target object X. Thereby, the EIT measurement device 1 can automatically specify a position of the second base point β, a strain gauge adjacent to the second base point β, and a distance P1A from the strain gauge.

Also, although the case in which the EIT measurement device 1 according to the third embodiment specifies relative positions of subordinate points N13H2 and N13I2 for the reference point N13Q under the assumption that the curvature acquired by the virtual strain gauge 13Q arranged at the second base point β is zero has been described, the EIT measurement device 1 according to another embodiment is not limited to this aspect. For example, the EIT measurement device 1 may divide a distance between the subordinate point N13I2 and the subordinate point N13H2 into micro distances dP and obtain a curvature at a position corresponding to the reference point N13Q arranged between the subordinate point N13I2 and the subordinate point N13H2 by performing an interpolation using the curvature (actually measured value) acquired by each of the strain gauges 13I and 13H.

Also, although the EIT measurement devices 1 according to the first to third embodiments and their modified examples have been described to precisely estimate a shape of a contour of the measurement target object X on the basis of curvature data acquired from "strain gauges" (strain gauges 13A to 13P) periodically arranged on the measurement belt 10, the "strain gauge" is only one aspect for acquiring curvature data at a position at which each of the strain gauges is arranged. The EIT measurement device 1 according to the above-described embodiments does not need to necessarily use a strain gauge for acquiring curvature data, but may use another curvature sensor capable of acquiring curvature data. As an aspect of the curvature sensor, for example, a curvature sensor to which a conductive ink is applied, etc. are included. The curvature sensor using the conductive ink is manufactured using a change in electrical resistance of the conductive ink by expanding or contracting the conductive ink coated (printed) on a surface of a bendable substrate in accordance with bending of the substrate.

Also, the EIT measurement devices 1 according to the first to third embodiments and their modified examples in which all the electrode pads 12A, 12B, . . . and the strain gauges 13A, 13B, . . . are periodically arranged at regular intervals (intervals P) in the measurement belt 10 has been described, but the electrode pads 12A, 12B, . . . and the strain gauges 13A, 13B, . . . do not have to be periodically arranged in the EIT measurement device 1 according to another embodiment. That is, when intervals between the electrode pads 12A, 12B, . . . and the strain gauges 13A, 13B, . . . are known in the EIT measurement device 1 according to another embodiment, they may be arranged at mutually different intervals.

Also, the EIT measurement main body unit 20 according to each embodiment internally has a computer system as described above in the above description. A process of the processing in the above-described EIT measurement main body unit 20 is stored in a computer-readable recording medium in the form of a program. The above-described process is performed when a computer reads and executes the program. Here, the computer-readable recording medium is a magnetic disk, a magneto-optical disc, a compact disc read-only memory (CD-ROM), a semiconductor memory, or the like. In addition, the computer program may be distributed to the computer through a communication line, and the computer receiving the distributed program may execute the program.

While some embodiments of the present invention have been described above, these embodiments are examples of the invention and are not intended to limit the scope of the invention. These embodiments may be performed in various other forms and various omissions, substitutions, and changes can be made without departing from the subject matter of the present invention. These embodiments and modifications are also considered to be included in the scope and subject matter of the present invention and these are also included in the invention disclosed in the appended claims and its equivalent scope.

Fourth Embodiment

According to the EIT measurement device, EIT measurement method, and the non-transitory recording medium storing program according to the first embodiment to the third embodiment of the present invention described above, it is possible to measure the shape and the size of the contour more simply and accurately. However, the present invention is not limited to the disclosure of the first embodiment to the third embodiment described above. More specifically, for example, according to a contour shape estimation device according to the fourth embodiment described below, it is possible to estimate the contour shape and measure the perimeter without using the EIT measurement method.

Figure 29:
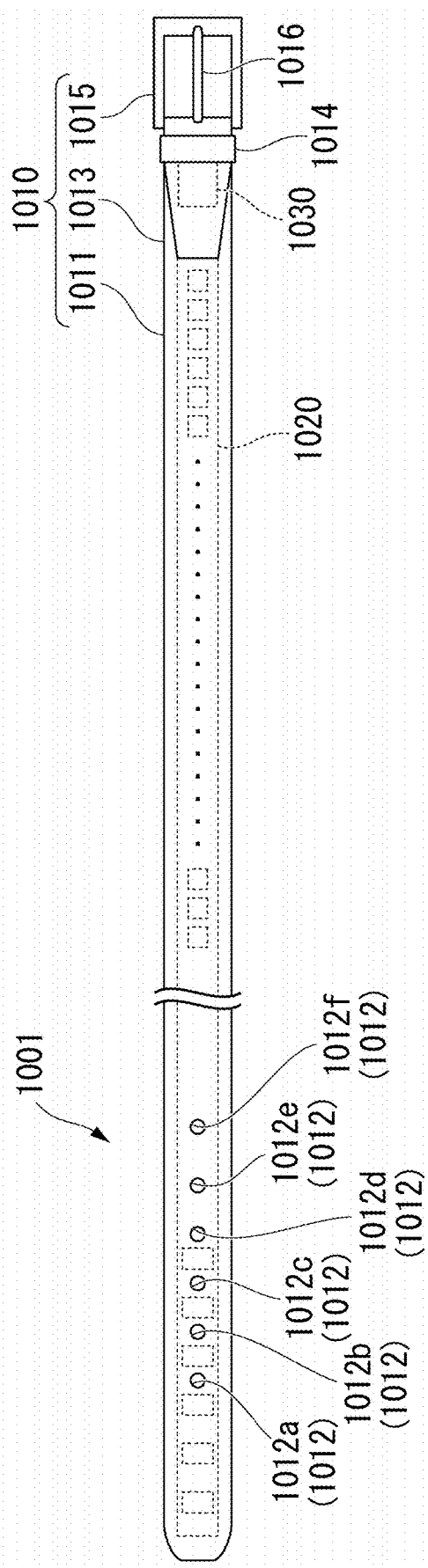
FIG. 29 is a schematic view showing a configuration of a contour estimation device according to a fourth embodiment of the present invention.

FIG. 29 is a view showing a schematic configuration example of the contour estimation device according to the fourth embodiment of the present invention. A contour-shape estimation device 1001 shown in FIG. 29 is summarized and implemented (integrated) in a belt. In other words, each configuration of the contour-shape estimation device 1001 is disposed in the belt main body 1010. The belt main body 1010 has a belt 1011, a cosmetic case 1013, a ring 1014, and a buckle 1015. The buckle 1015 has a needle 1016. Hereinafter, between two ends of the belt main body 1010 in the longitudinal direction, one end having the buckle 1015 is described as a forehead end and the other end opposite to the forehead end is described as a tail end.

The contour-shape estimation device 1001 is configured to determine the perimeter of the measurement target part of the measurement target object and estimate the contour shape. More specifically, when the belt main body 1010 is wrapped around the measurement target object, the contour-shape estimation device 1001 is configured to determine the perimeter of the measurement target part around which the belt main body 1010 is wrapped, and estimate the contour shape.

Hereinafter, a case of describing a person as the measurement target object and the abdomen (circumference of the waist) as the measurement target part will be described. However, the measurement target object of the contour-shape estimation device 1001 is not limited to the person and the measurement target part of the contour-shape estimation device 1001 is not limited to the abdomen. For example, the contour-shape estimation device 1001 may be configured to determine the perimeter of the abdomen of an animal and estimate the contour shape. For example, the belt main body 1010 may be wrapped around an arm of the person, and the contour-shape estimation device 1001 may be configured to determine the perimeter of the arm and estimate the contour shape.

On the other hand, in the case in which the measurement target object is the person and the measurement target part is the abdomen, the contour-shape estimation device 1001 can be implemented in the belt for daily use as the belt main body 1010. Accordingly, the user can determine the contour shape and the perimeter of the abdomen by using the belt for daily use as usual. Thus, it is not necessary for the user to equip a device configured specifically for the determination and perform a specific operation for the determination. The user can use the information of the contour shape and the perimeter of the abdomen in the health management such as the management of the obesity index and the like.

The belt 1011 is formed to have six holes arranged in the longitudinal direction of the belt 1011. The longitudinal direction of the belt 1011 is also the longitudinal direction of the belt main body 1010. Hereinafter, the holes formed in the belt 1011 will be described as the belt hole 1012a, the belt hole 1012b, . . . , and the belt hole 1012f sequentially from the tail end side of the belt 1011. Also, the belt holes 1012a to 1012f are generically described as the belt holes 1012. The length of a loop formed by the belt can be adjusted by passing the needle 1016 through any of the belt holes 1012. Hereinafter, the length of the loop formed by the belt is described as the circumference of the belt.

Also, a flexible substrate 1020 is disposed in the belt 1011. More specifically, the flexible substrate 1020 is sandwiched between the two pieces of leather forming the belt 1011. The number of the belt holes 1012 only has to be equal to or more than 2 and is not limited to six as shown in FIG. 29.

The cosmetic case 1013 is disposed close to the buckle 1015, and the cosmetic case 1013 is configured to fix a cuff of the belt 1011 formed by folding a part of the buckle 1015. The cosmetic case 1013 is configured to sandwich a part of the ring 1014 to fix the ring 1014 to the belt 1011. A circuit substrate 1030 is disposed in the cosmetic case 1013.

The ring 1014 is configured for passing the odd part of the belt 1011 after passing the needle 1016 through the belt hole 1012. It is possible to prevent the odd part of the belt 1011 from hanging down to be an obstruction by passing the odd part of the belt 1011 through the ring 1014. The buckle 1015 is a metal fitting configured to hold the state in which the needle 1016 passes through the belt hole 1012.

Figure 30:
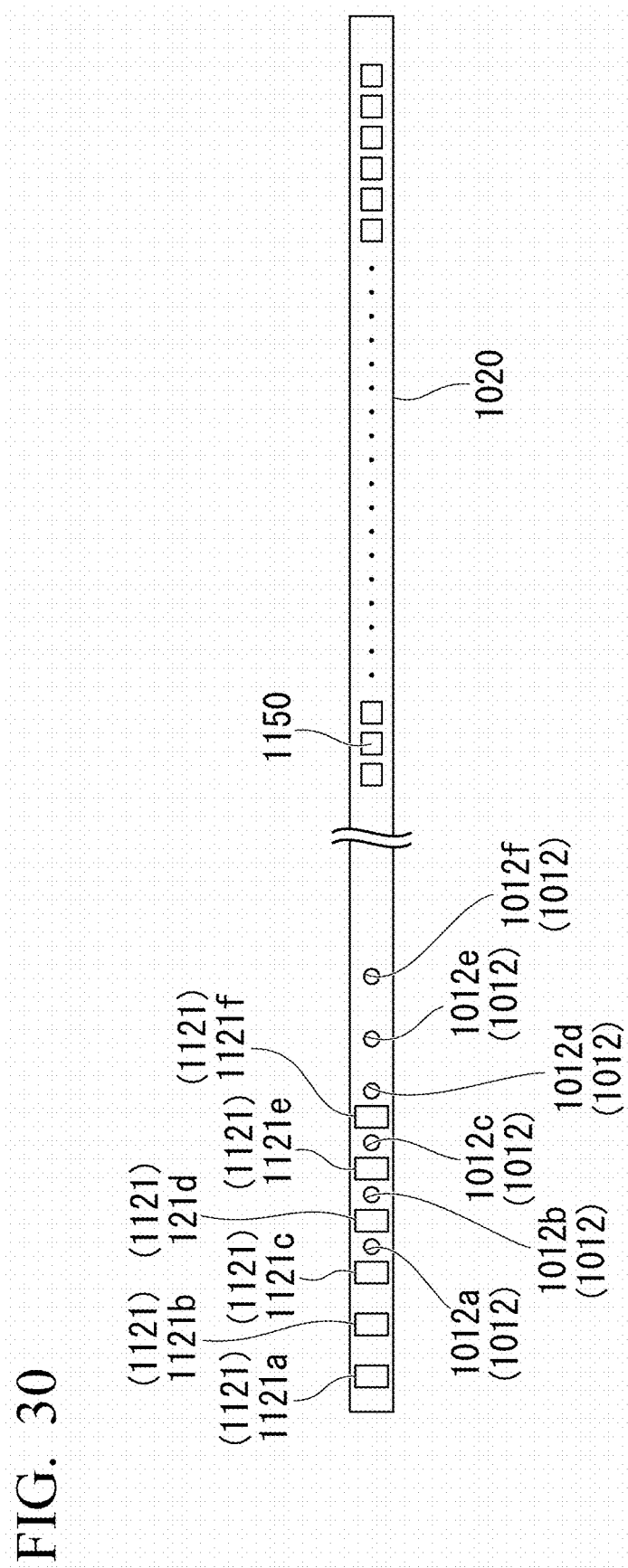
FIG. 30 is a view showing a configuration example of sensors provided on a flexible substrate according to the fourth embodiment.

FIG. 30 is a view showing a configuration example of sensors provided on the flexible substrate 1020. In the contour-shape estimation device 1001, the first electrode 1121 and the second electrode 1131 are used as part of the sensors configured to seek the circumference length of the belt main body 1010. Accordingly, the first electrode 1121 and the second electrode 1131 are described as the sensors.

As shown in FIG. 30, in the flexible substrate 1020, six first electrodes 1121 are arranged in the longitudinal direction of the flexible substrate 1020. The longitudinal direction of the flexible substrate 1020 coincides with the longitudinal direction of the belt main body 1010 in the state in which the flexible substrate 1020 is implemented in the belt main body 1010.

Hereinafter, the first electrodes 1121 are described as the first electrode 1121a, the first electrode 1121b, . . . , and the first electrode 1121f sequentially from the tail end side of the belt main body 1010. The two ends of the flexible substrate 1020 in the longitudinal direction thereof are distinguished from the forehead end side and the tail end side of the belt main body 1010 when the flexible substrate 1020 is implemented in the belt main body 1010.

In the flexible substrate 1020, a plurality of curvature sensor 1150 are arranged in the longitudinal direction of the flexible substrate 1020. Here, the curvature sensor refers to the sensor configured to measure the curvature by which the curvature sensor itself is bent. The curvature measured by the curvature sensor 1150 indicates the curvature of the position on the belt main body 1010 at which the curvature sensor 1150 is disposed.

In the flexible substrate 1020, six holes are opened and arranged in the longitudinal direction of the flexible substrate 1020. Hereinafter, the holes of the flexible substrate 1020 are described as the substrate hole 1021a, the substrate hole 1021b, . . . , and the substrate hole 1021f sequentially from the tail end side of the belt main body 1010. The substrate holes 1021a to 1021f are generally described as the substrate holes 1021.

The substrate hole 1021a, the substrate hole 1021b, . . . , and the substrate hole 1021f are opened at the positions coinciding with the positions of the belt hole 1012a, the belt hole 1012b, . . . , and the belt hole 1012f, respectively in the state in which the flexible substrate 1020 is implemented in the belt main body 1010.

The configuration example of the sensors shown in FIG. 30 is not limited thereto. For example, in FIG. 30, the first electrodes 1121 are arranged at the tail end side of the belt main body 1010, the curvature sensors 1150 are arranged at the forehead side of the belt main body 1010, and the arrangement area of the first electrodes 1121 is separated from the arrangement area of the curvature sensors 1150. However, the first electrodes 1121 and the curvature sensors 1150 may be arranged such that the arrangement area of the first electrodes 1121 and the arrangement area of the curvature sensors 1150 is superimposed on each other across part or whole of the belt 101. Such a configuration can be realized using the multi-layer substrate technology or the technology of stacking multiple substrates.

Figure 31:
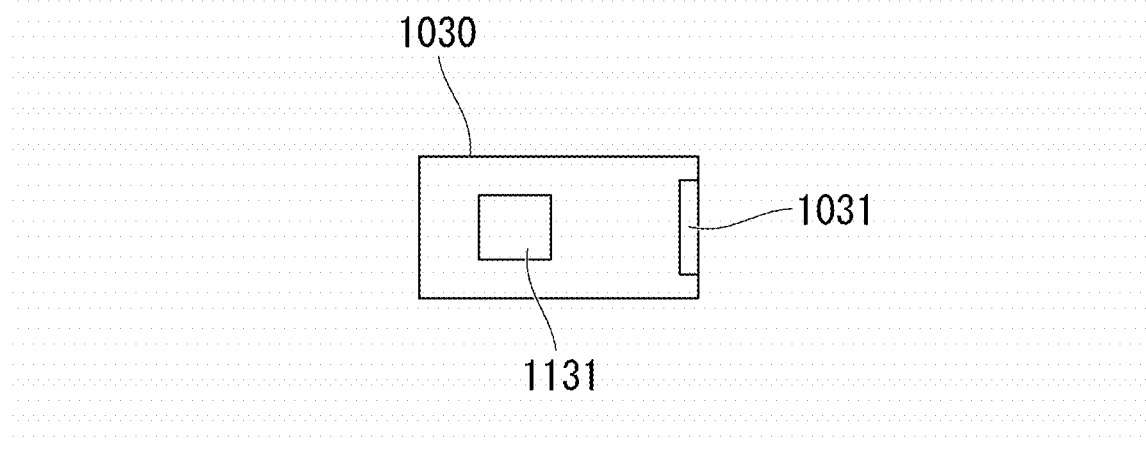
FIG. 31 is a view showing a configuration example of sensors provided on a circuit substrate according to the fourth embodiment.

FIG. 31 is a view showing a configuration example of sensors provided on the circuit substrate 1030. As shown in FIG. 31, the second electrode 1131 is disposed on the circuit substrate 1030.

A connector 1031 is disposed on the circuit substrate 1030. The connector 1031 is a connector for electrically connecting the flexible substrate 1020 and the circuit substrate 1030.

Figure 32:
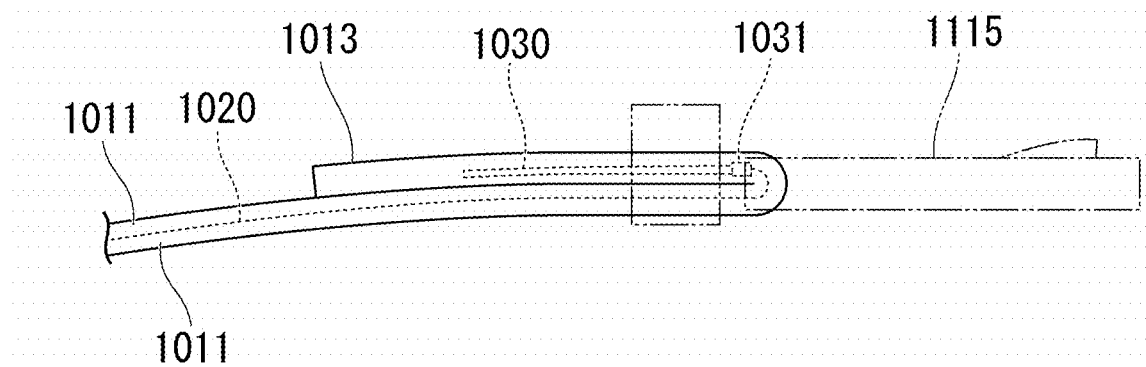
FIG. 32 is a view showing the configuration example of the circuit substrate according to the fourth embodiment.

FIG. 32 is a view showing a configuration example of the circuit substrate 1030. As described above, the flexible substrate 1020 is configured to be sandwiched by the two pieces of leather of the belt 1011. The circuit substrate 1030 is accommodated in the cosmetic case 1013.

The circuit substrate 1030 is configured such that the connector 1031 faces the side of the buckle 1015. The end portion at the side of the buckle 1015 of the flexible substrate 1020 is folded and connected to the connector 1031. The exterior appearance of the belt main body 1010 is the same as that of the belt for daily use.

Figure 33:
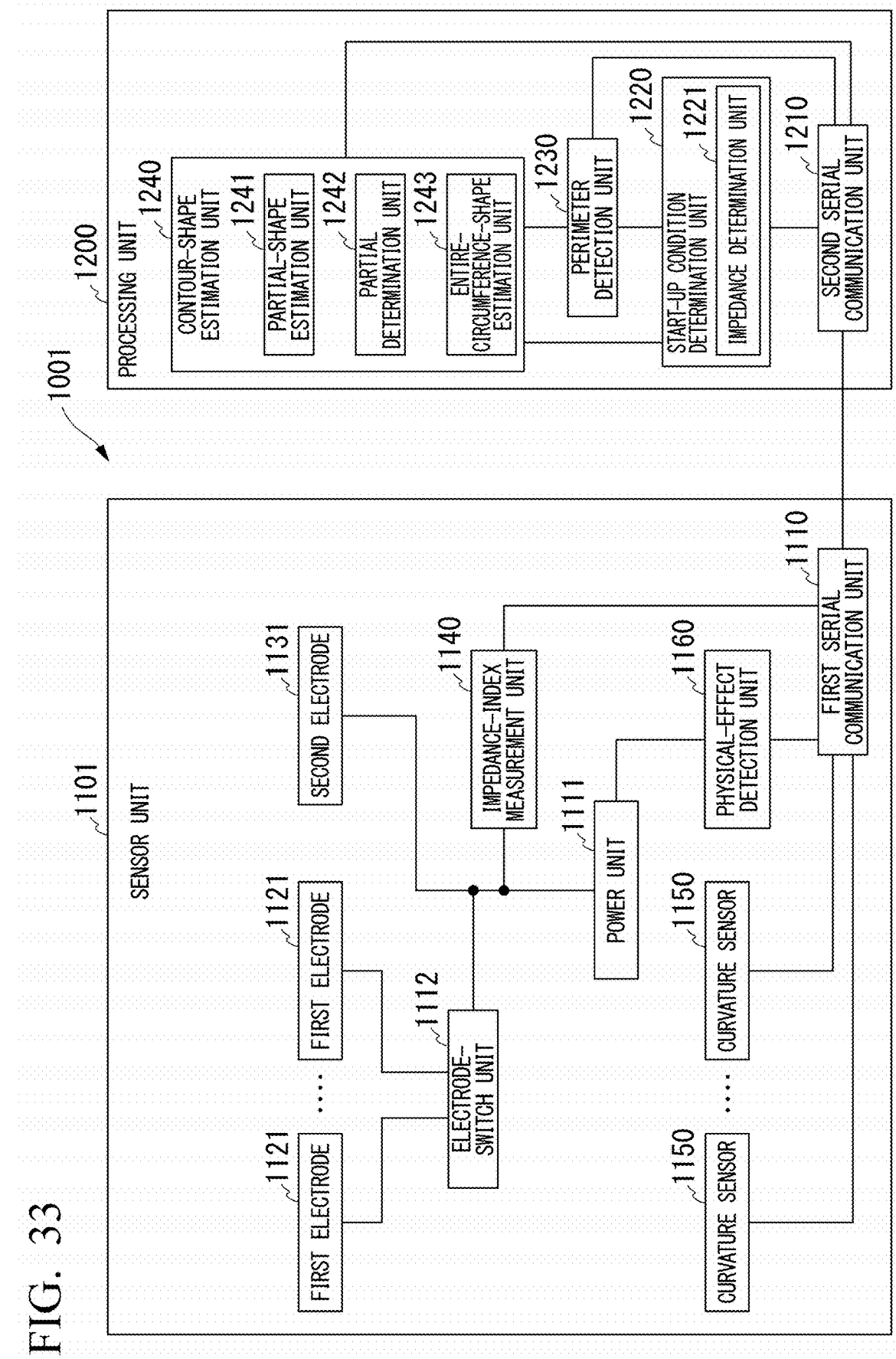
FIG. 33 is a schematic block diagram showing functional configurations of the contour estimation device according to the fourth embodiment.

FIG. 33 is a schematic block diagram showing the functional configurations of the contour-shape estimation device 1001. As shown in the figure, the contour-shape estimation device 1001 has a sensor unit 1100 and a processing unit 1200. The sensor unit 1100 has a first serial communication unit 1110, a power supply 1111, an electrode-switching unit 1112, the first electrode 1121, the second electrode 1131, an impedance-index measurement unit 1140, the curvature sensor 1150, and the physical-effect detection unit 1160. The processing unit 1200 has a second serial communication unit 1210, a start-condition determination unit 1220, a perimeter detection unit 1230, and a contour-shape estimation unit 1240. The start-condition determination unit 1220 has an impedance determination unit 1221. The contour-shape estimation unit 1240 has a partial-shape estimation unit 1241, a partial determination unit 1242, and an entire-circumference-shape estimation unit 1243.

A case in which each unit (all units) of the contour-shape estimation device 1001 is implemented in the belt main body 1010 will be described. However, the contour estimation device may be configured to have some units arranged in another device different from the belt main body 1010. For example, the processing unit 1200 may be configured as another device with respect to the belt main body 1010.

On the other hand, by implementing each unit of the contour-shape estimation device 1001 in the belt main body 1010, the user can use the contour-shape estimation device 1001 in the same way as that of the belt for daily use so as to provide a high convenience for the user.

The sensor unit 1100 is configured to have the sensors for measuring the state of the belt main body 1010. Among the configurations of the sensor unit 1100, the first serial communication unit 1110, the electrode-switching unit 1112, the first electrode 1121, the impedance-index measurement unit 1140, and the curvature sensor 1150 are disposed on the flexible substrate 1020. On the other hand, the power supply 1111, the second electrode 1131, and the physical-effect detection unit 1160 are disposed on the circuit substrate 1030. However, the power supply 1111, the electrode-switching unit 1112, the impedance-index measurement unit 1140 and the physical-effect detection unit 1160 may be disposed on either of the flexible substrate 1020 and the circuit substrate 1030.

The first serial communication unit 1110 is configured to transmit each measurement value acquired by the sensor unit 1100 to the processing unit 1200 via the serial communication. As described below, the first serial communication unit 1110 may be configured from a plurality of communication circuits.

The power supply 1111 is configured to have a power source such as a button battery and the like for supplying the power to each unit of the contour-shape estimation device 1001. Particularly, the power supply 1111 is configured to supply (apply) an AC voltage to the first electrode 1121 and the second electrode 1131. The power supply 1111 is configured to supply a DC voltage to the curvature sensor 1150. The power supply 1111 is configured to supply a relatively high frequency AC voltage such as equal to or higher than 1100 kHz and the like. Accordingly, the electrostatic induction effect may be enhanced when the first electrode 1121 and the second electrode 1131 face each other so as to function as a capacity.

The electrode-switching unit 1112 is configured to switch the first electrodes 1121 in time-division manner during the measurement (detection) of the circumference length of the belt main body 1010, wherein the voltage from the power supply 1111 is applied on the first electrodes 1121.

The voltage from the power supply 1111 is applied on the first electrodes 1121 and the second electrodes 1131. Particularly, the voltage from the power supply 1111 is applied on the first electrodes 1121*a*-1121*f* in time-division manner via the electrode-switching unit 1112. The impedance index measurement unit 1140 is configured to measure the index value indicating the impedance between the first electrode 1121 and the second electrode 1131.

Figure 34:
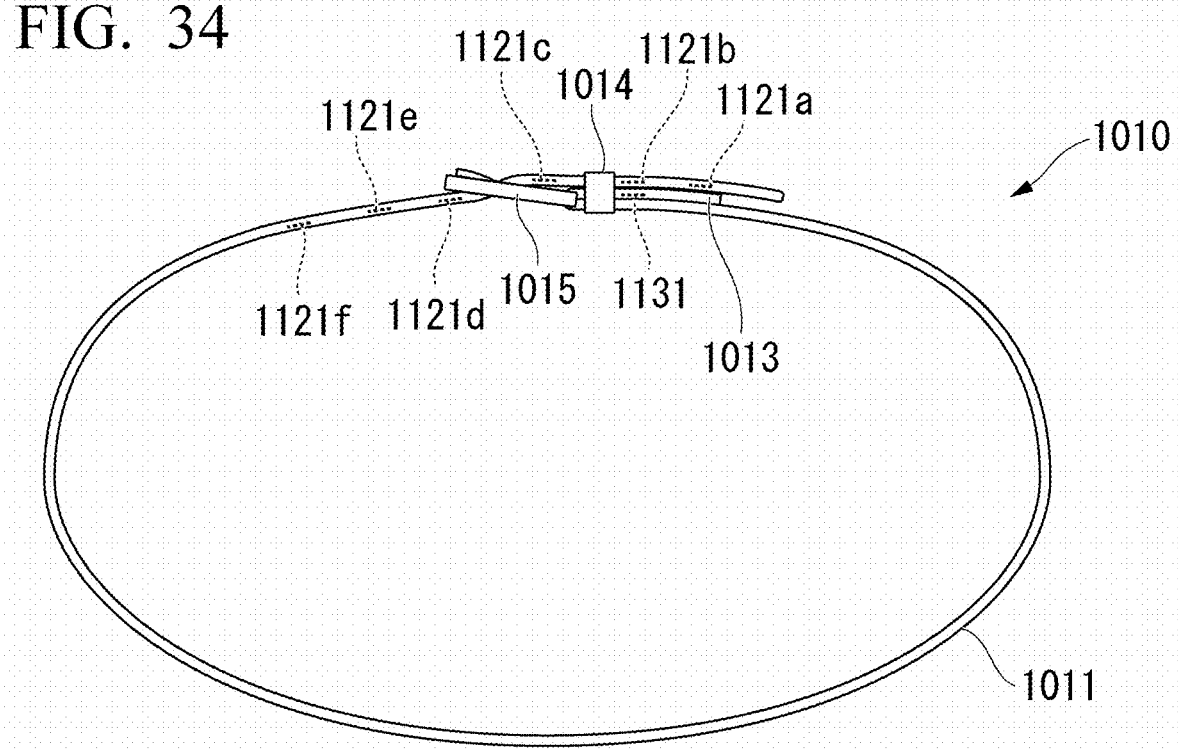
FIG. 34 is a view showing a positional relationship between a first electrode and a second electrode when the contour estimation device is attached to a user according to the fourth embodiment.

FIG. 34 is a view showing a positional relationship between the first electrode 1121 and the second electrode 1131 in the state in which the contour-shape estimation device 1001 (belt main body 1010) is attached to the user.

As shown in FIG. 34, in the state in which the contour-shape estimation device 1001 is attached to the user, the belt main body 1010 forms a ring. The contour-shape estimation device 1001 is configured to determine the circumference length of the belt main body 1010 in this state as the perimeter of the measurement target part. Generally, the contour-shape estimation device 1001 (belt main body 1010) is wrapped around the abdomen of the user to be used. In this state, the contour-shape estimation device 1001 is configured to determine the circumference length (abdominal circumference) of the abdomen of the user.

The first electrodes 1121 is disposed at the positions such that any of the first electrodes 1121 opposites the second electrode 1131 (the surface of the first electrode 1121 faces the surface of the second electrode 1131) in the state in which the contour-shape estimation device 1001 (the belt main body 1010) is attached to the user. More specifically, when the needle 1016 is passed through the belt hole 1012*a*, the first electrode 1121*a* is disposed to face the second electrode 1131. Similarly, when the needle 1016 is passed through the belt hole 1012*b*, 1012*c*, . . . , 1012*f*, the first electrode 1121*b*, 1121*c*, . . . , 1121*f* is disposed to face the second electrode 1131, respectively.

In FIG. 34, the example of passing the needle 1016 through the belt hole 1012*b* is shown, and the first electrode 1121*b* is disposed to face the second electrode 1131.

In the present embodiment, the partial-shape estimation unit 1241 is configured to estimate the partial shape that is the shape of part of the contour of the whole circumference of the measurement target portion according to the sensor value of the curvature sensor 1150 (the curvature measured by the curvature sensor 1150). The partial-shape estimation unit 1241 according to the present embodiment is configured to operate according to the same principle of the contour estimation unit 202 according to the first embodiment described above and the description in detail will be omitted.

Figure 35:
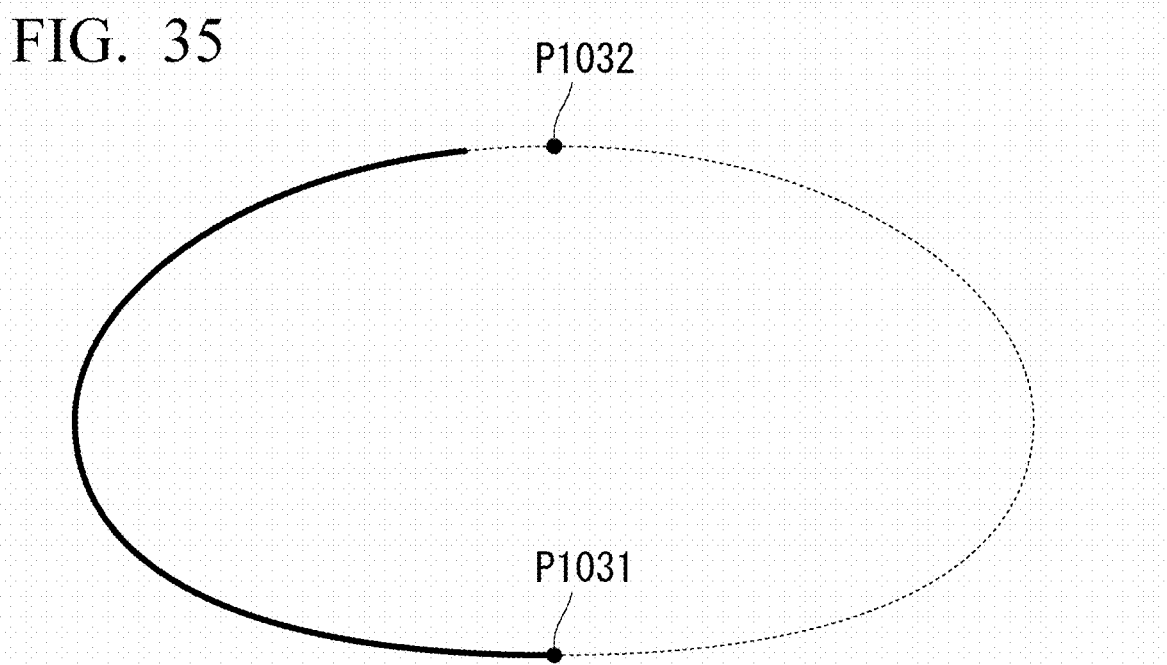
FIG. 35 is a view showing an example of positions estimated by a partial determination unit according to the fourth embodiment.

FIG. 35 is a view showing an example of estimating the positions by the partial determination unit 1242. In FIG. 35, the partial shape estimated by the partial-shape estimation unit 1241 is shown in solid line, and the remaining part of the whole circumference of the measurement target portion (the other part than the part whose shape is estimated by the partial-shape estimation unit 1241) is shown in dashed line. The position which is estimated by the partial determination unit 1242 to be the center position at the back side is shown as the point P1031, and the position which is estimated to be the center position at the abdomen side is shown as the point P1032.

In the example shown in FIG. 35, there is not any curvature sensor 1150 disposed in the part having the cosmetic case 1013 in the belt main body 1010. Accordingly, in the vicinity of the point P1032 (the center position at the abdomen side), the partial-shape estimation unit 1241 does not estimate the shape thereof. However, the distance from the boundary position of the buckle 1015 and the cosmetic case 1013 to the curvature sensor 1150 is already known, thus the buckle 1015 is configured to be able to estimate the point P1031 (the center position of the back side). In the example shown in FIG. 35, the curvature sensor 1150 is disposed the part covering more than half length of the belt main body 1010, and the partial-shape estimation unit 1241 is configured to estimate the partial shape with respect to the range covering more than half of the contour of the measurement target portion. Accordingly, the partial determination unit 1242 is configured to estimate that the position of the point P1031 is in the range in which the partial shape is estimated by the partial-shape estimation unit 1241.

Or the partial determination unit 1242 may be configured to estimate the center position at the back side in the range in which the curvature becomes minimum. For example, the partial determination unit 1242 is configured to extract the curvatures equal to or less than the predetermined threshold value among the curvatures measured by the curvature sensor 1150. Then, the partial determination unit 1242 is configured to estimate the range corresponding to the extracted curvatures (the range in which the partial-shape estimation unit 1241 performs the contour shape approximation according to the curvatures) as the range of the back side. Subsequently, the partial determination unit 1242 is configured to estimate the estimated center position of the back side as the center position of the back side (the point P1031 is FIG. 35).

The partial determination unit 1242 is configured to estimate the position from the estimated center position of the back side by half of the perimeter as the center position of the abdomen side.

The whole-circumference-shape estimation unit 1243 is configured to estimate the shape of the whole circumference shape of the measurement target portion from the partial shape according to the determination result of the partial determination unit 1242 and the assumption that the contour shape of the whole circumference of the target portion is linearly symmetrical.

More specifically, the whole-circumference-shape estimation unit 1243 is configured to divide the partial shape estimated by the partial-shape estimation unit 1241 into two parts by the estimated center position of the back side that is estimated by the partial determination unit 1242 and extract the wider part thereof as the partial shape of the duplication target. In the example shown in FIG. 35, the whole-circumference-shape estimation unit 1243 is configured to extract the partial shape in the range shown in bold line as the partial shape of the duplication target.

Then, the whole-circumference-shape estimation unit 1243 is configured to perform a horizontal inversion (that is, perform a line symmetry) with respect to the extracted partial shape and duplicate the extracted partial shape.

Figure 36:
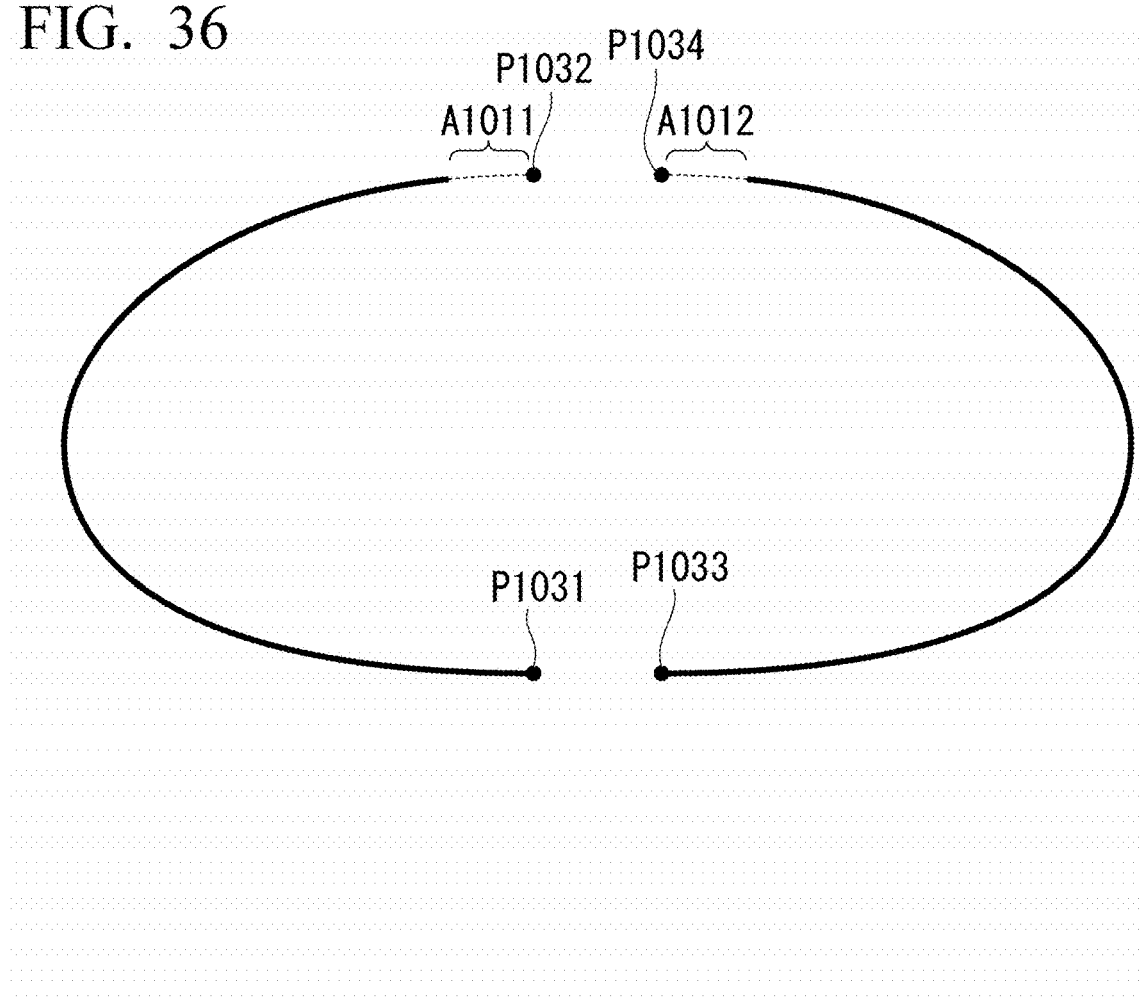
FIG. 36 is a view showing an example of a partial shape reproduced by an entire-circumference-shape estimation unit according to the fourth embodiment.

FIG. 36 is a view showing the example of the partial shape duplicated by the whole-circumference-shape estimation unit 1243. In the example shown in FIG. 36, the whole-circumference-shape estimation unit 1243 is configured to acquire the partial shape in the range from the point P1033 to the point P1034 by performing the horizontal inversion with respect to the partial shape from the point P1031 to the point P1032 which is extracted as the partial shape of the duplication target and duplicating the partial shape thereof.

The whole-circumference-shape estimation unit 1243 is configured to connect the partial shape acquired by the duplication to the original partial shape. At this time, the shape of the part corresponding to the buckle 1015 (in the example of FIG. 36, the parts of the region A1011 and the region A1012) is unknown such that there are degrees of freedom in the connection method. The whole-circumference-shape estimation unit 1243 is configured to connect the partial shape of the duplication source and the partial shape acquired by the duplication by connecting the point P1031 and the point P1033 and smoothing the connection portion (an angle at the local site is 180 degrees).

Figure 37:
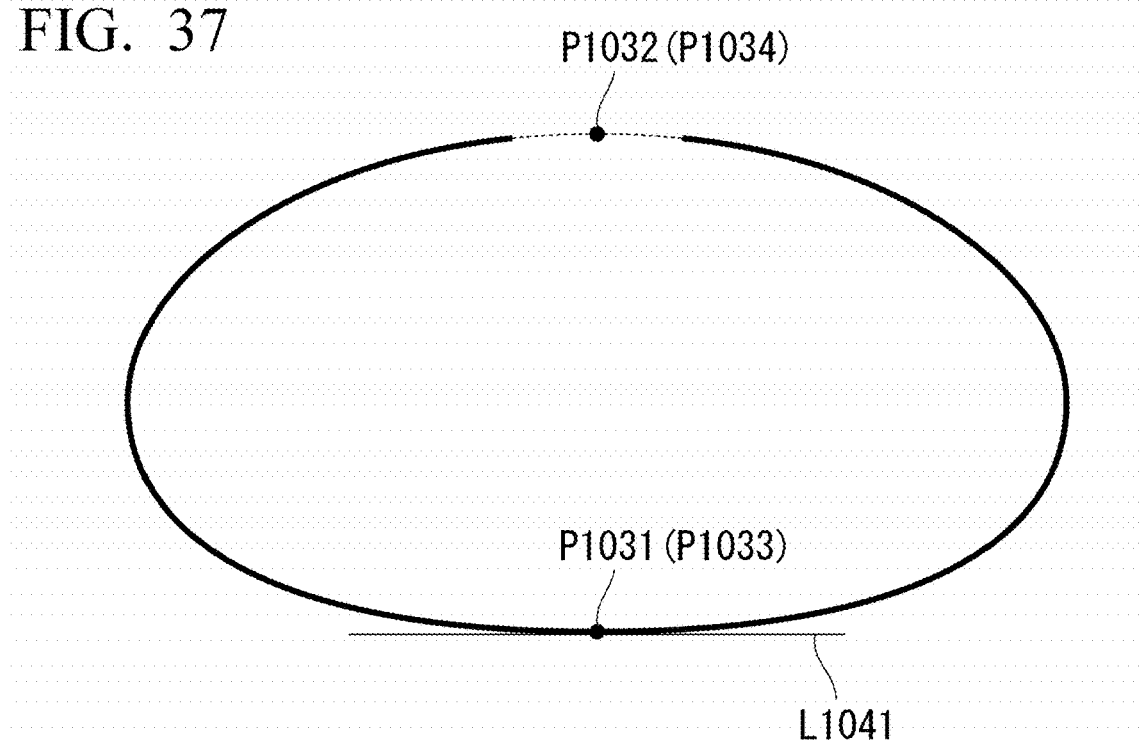
FIG. 37 is a view showing an example of joining the original partial shape and the reproduced partial shape according to the fourth embodiment.

FIG. 37 is a view showing the example of connecting the partial shape of the duplication source and the partial shape acquired by the duplication. In FIG. 37, the point P1031 and the point P1033 are connected with each other. Also, the connection portion is smoothed. More specifically, the angle at the local site of the connection portion is 180 degrees such that the tangential line L1041 is uniquely determined.

The whole-circumference-shape estimation unit 1243 is configured to complete the shape of the portion corresponding to the buckle 1015 and estimate the whole contour shape of the measurement target.

The whole-circumference-shape estimation unit 1243 may be configured to perform an interpolation by approximating the part corresponding to the buckle 1015 with a straight line. Or the whole-circumference-shape estimation unit 1243 may perform the interpolation by approximating the part corresponding to the buckle 1015 with a non-linear figure such as a circular arc.

The whole-circumference-shape estimation unit 1243 may be configured to determine the position of the point P1032 with respect to the point P1031 and the position of the point P1034 with respect to the point P1033 by estimating the shape of the part corresponding to the buckle 1015. In this case, the whole-circumference-shape estimation unit 1243 is configured to connect the partial shape of the duplication source and the partial shape acquired by the duplication by connecting the point P1031 with the point P1033 and connecting the point P1032 and the point P1034.

Next, operations of the contour-shape estimation device 1001 will be described by referring to FIG. 38 and FIG. 39.

Figure 38:
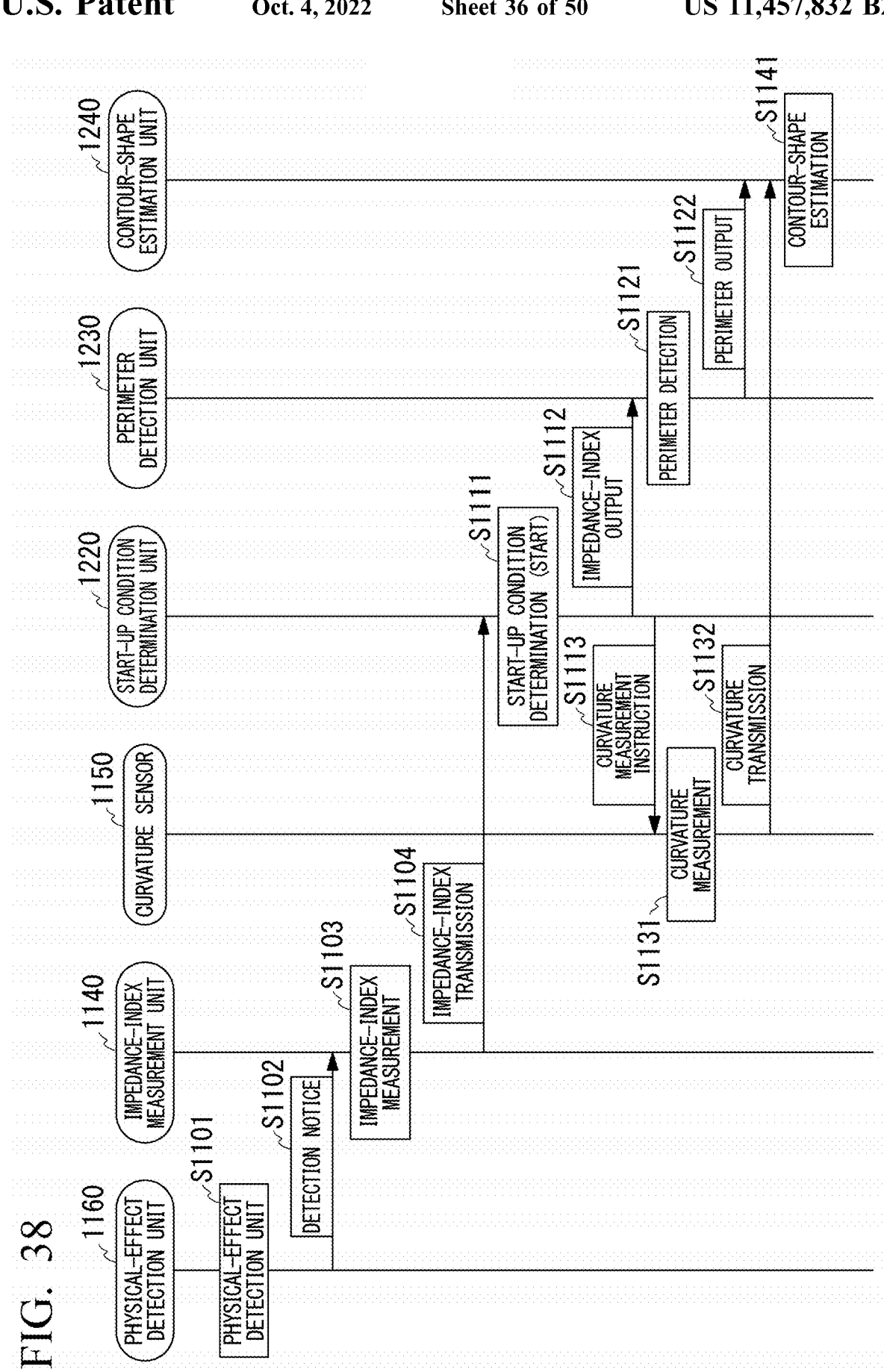
FIG. 38 is a diagram showing an example of processing procedures for determining the perimeter and estimating the contour shape of the measurement object portion by the contour shape estimation device according to the fourth embodiment.

FIG. 38 is a view showing a diagram showing an example of processing procedures for determining the perimeter and estimating the contour shape of the measurement object portion by the contour shape estimation device 1001.

In the processing shown in FIG. 38, when the physical-effect detection unit 1160 detects the predetermined physical effect (sequence S1101), the physical-effect detection unit 1160 is configured to output a notice indicating the detection to the impedance-index measurement unit 1140 (sequence S1102).

The impedance-index measurement unit 1140 receiving the notice from the physical-effect detection unit 1160 is configured to measure the index value indicating the impedance between each of the first electrodes 1121 and the second electrode 1131 (sequence S1103), and the impedance-index measurement unit 1140 is configured to output the acquired index values to the start-up condition determination unit 1220 (sequence S1104).

The start-up condition determination unit 1220 is configured to determine whether or not the start-up condition for determining the perimeter of the measurement target portion and estimating the contour shape of the measurement target portion is fulfilled according to the index values acquired by the impedance-index measurement unit 1140 (sequence S1111). Accordingly, the start-up condition determination unit 1220 is configured to determine whether to start the determination of the perimeter of the measurement target portion and the estimation of the contour shape of the measurement target portion. In the example shown in FIG. 38, the start-up condition determination unit 1220 has determined to start the determination of the perimeter of the measurement target portion and the estimation of the contour shape of the measurement target portion.

On the other hand, when the start-up condition determination unit 1220 determines to not to start the determination of the perimeter of the measurement target portion and the estimation of the contour shape of the measurement target portion, the processing shown in FIG. 38 is finished.

The start-up condition determination unit 1220 which has decided to start the determination of the perimeter of the measurement target portion and the estimation of the contour shape of the measurement target portion is configured to output (transmit) the index values acquired in the sequence S1104 to the perimeter detection unit 1230 (sequence S1112).

The perimeter detection unit 1230 is configured to determine the perimeter of the measurement target portion according to the acquired index values (sequence S1121). The perimeter detection unit 1230 is configured to output the determined perimeter to the contour-shape estimation unit 1240 (sequence S1122).

The start-up condition determination unit 1220 which has decided to start the determination of the perimeter of the measurement target portion and the estimation of the contour shape of the measurement target portion is configured to control the sensor unit 1100 to make the curvature sensors 1150 to measure the curvature (sequence S1113). Specifically, the start-up condition determination unit 1220 is configured to control the power supply 1111 so as to supply the power to each of the curvature sensor 1150.

Each of the curvature sensors 1150 is configured to measure the curvature (sequence S1131). Each of the curvature sensors 1150 is configured to output the acquired curvature to the contour-shape estimation unit 1240 (sequence S1132).

The contour-shape estimation unit 1240 is configured to estimate the contour shape of the measurement target portion according to the perimeter acquired in the sequence S1122 and the curvatures acquired in the sequence S1132 (sequence S1141).

Figure 39:
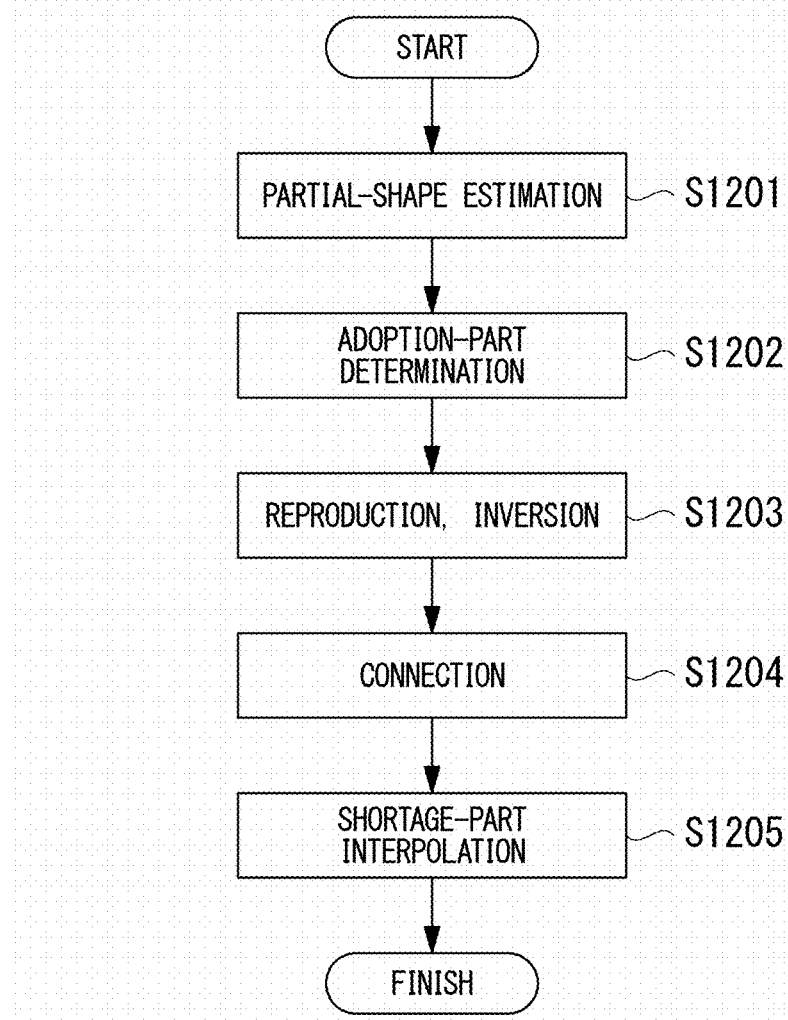
FIG. 39 is a flowchart showing an example of processing procedures for estimating the contour shape of the measurement object portion according to the fourth embodiment.

FIG. 39 is a flowchart showing an example of the processing procedures of the contour-shape estimation unit 1240 for estimating the contour shape of the measurement target portion. The contour-shape estimation unit 1240 is configured to perform the processing shown in FIG. 39 during the sequence 1141 shown in FIG. 38.

In the processing shown in FIG. 39, the partial-shape estimation unit 1241 of the contour-shape estimation unit 1240 is configured to estimate the partial shape of the measurement target portion (step S1201).

Subsequently, the partial determination unit 1242 is configured to determine the part used in the estimation of the whole contour shape from the partial shape estimated by the partial-shape estimation unit 1241 in the step S1201 (Step S1202).

Subsequently, the whole-circumference-shape estimation unit 1243 is configured to perform the horizontal inversion with respect to the part determined by the partial determination unit 1242 in the partial shape estimated by the partial-shape estimation unit 1241 and duplicate the part (Step S1203).

The whole-circumference-shape estimation unit 1243 is configured to connect the partial shape of the duplication source and the part acquired by the duplication (Step S1204).

The whole-circumference-shape estimation unit 1243 is configured to interpolate the insufficient part with respect to the contour shape acquired in the Step S1204 (Step S1205). Accordingly, the whole-circumference-shape estimation unit 1243 is configured to estimate the shape of the whole circumference contour of the measurement target portion.

As described above, the physical-effect detection unit 1160 is configured to detect the specified physical effect with respect to the belt main body 1010.

The impedance determination unit 1221 is configured to determine whether there is a first electrode 1121 whose impedance with respect to the second electrode 1131 is equal to or less than the predetermined impedance. The contour-shape estimation 1240 is configured to estimate the contour shape of the measurement target portion according to the sensor values of the curvature sensors 1150 in the case when the physical-effect detection unit 1160 detects the specified physical effect and the impedance determination unit 1221 determines that there is a first electrode 1121 whose impedance with respect to the second electrode 1131 is equal to or less than the predetermined impedance.

Accordingly, the contour-shape estimation device 1001 is configured to determine whether the belt main body 1010 is wrapped (the state in which whether the needle 1016 is passed through any of the belt holes 1012), and the subsequent processing can be prevented when the belt main body 1010 is determined to be not wrapped. Accordingly, the power consumption of the contour-shape estimation device 1001 can be reduced.

The physical-effect detection unit 1160 is configured to detect the movement of the belt main body 1010. Accordingly, the contour-shape estimation device 1001 can determine whether to estimate the contour shape of the perimeter of the measurement target triggered by moving the belt for attaching the belt to the user. The processing of the contour-shape estimation device 1001 can be prevented when the user does not move the belt, and the power consumption of the contour-shape estimation device 1001 can be reduced.

The physical-effect detection unit 1160 is also to be able to detect the pressure on the specified portion of the belt main body 1010. Accordingly, the contour-shape estimation device 1001 can detect the state in which the specified portion is pressed when the belt main body 1011 is attached to the user such as the user passes the belt through the buckle 1015. The processing of the contour-shape estimation device 1001 is prevented when the pressing with respect to the specified portion is not detected, and the power consumption of the contour-shape estimation device 1001 can be reduced.

The perimeter detection unit 1230 is configured to determine the perimeter of the measurement target portion according to the impedance between the first electrode 1121 and the second electrode 1131.

Accordingly, the contour-shape estimation device 1001 can determine whether to estimate the contour shape of the perimeter of the measurement target using the first electrodes 1121 and the second electrode 1131 for detecting the perimeter. The configuration of the contour-shape estimation device 1001 can be simplified since it is not necessary to provide other electrode exclusively used for determining whether to estimate the contour shape of the perimeter of the measurement target.

The perimeter detection unit 1230 is configured to detect the perimeter of the measurement target portion when the physical-effect detection unit 1160 detects the predetermined physical effect and the impedance determination unit 1221 determines that there is the first electrode 1121 whose impedance with respect to the second electrode 1131 is equal to or less than the predetermined impedance.

Accordingly, the contour-shape estimation device 1001 is configured to determine the state whether the belt main body 1010 is wrapped (the state in which whether the needle 1016 is passed through any of the belt holes 1012), and it is possible to prevent both of the estimation of the contour shape of the measurement target portion and the detection of the perimeter of the measurement target portion when the belt main body 1010 is determined not to be wrapped. Thus, the power consumption of the contour-shape estimation device 1001 can be further reduced.

The partial-shape estimation unit 1241 is configured to estimate the shape of part of the whole circumference contour of the measurement target portion as the partial shape according to the sensor values of the curvature sensor 1150.

The partial determination unit 1242 is configured to determine the part of the whole circumference contour of the measurement target portion to which the partial shape estimated by the partial-shape estimation unit 1241 corresponds, according to the perimeter.

The entire-circumference-shape estimation unit 1243 is configured to estimate the shape of the whole circumference contour shape of the measuring target portion according to the determination result of the partial determination unit 1242 and the assumption that the contour shape of the whole circumference of the target portion is linearly symmetrical.

Accordingly, the contour-shape estimation device 1001 can estimate the contour shape of the whole circumference of the measuring target portion without disposing the curvature sensors 1150 covering whole of the belt 1011. The number of the curvature sensors 1150 can be reduced and the configuration of the contour-shape estimation device 1001 can be simplified.

<Modification>

Figure 40:
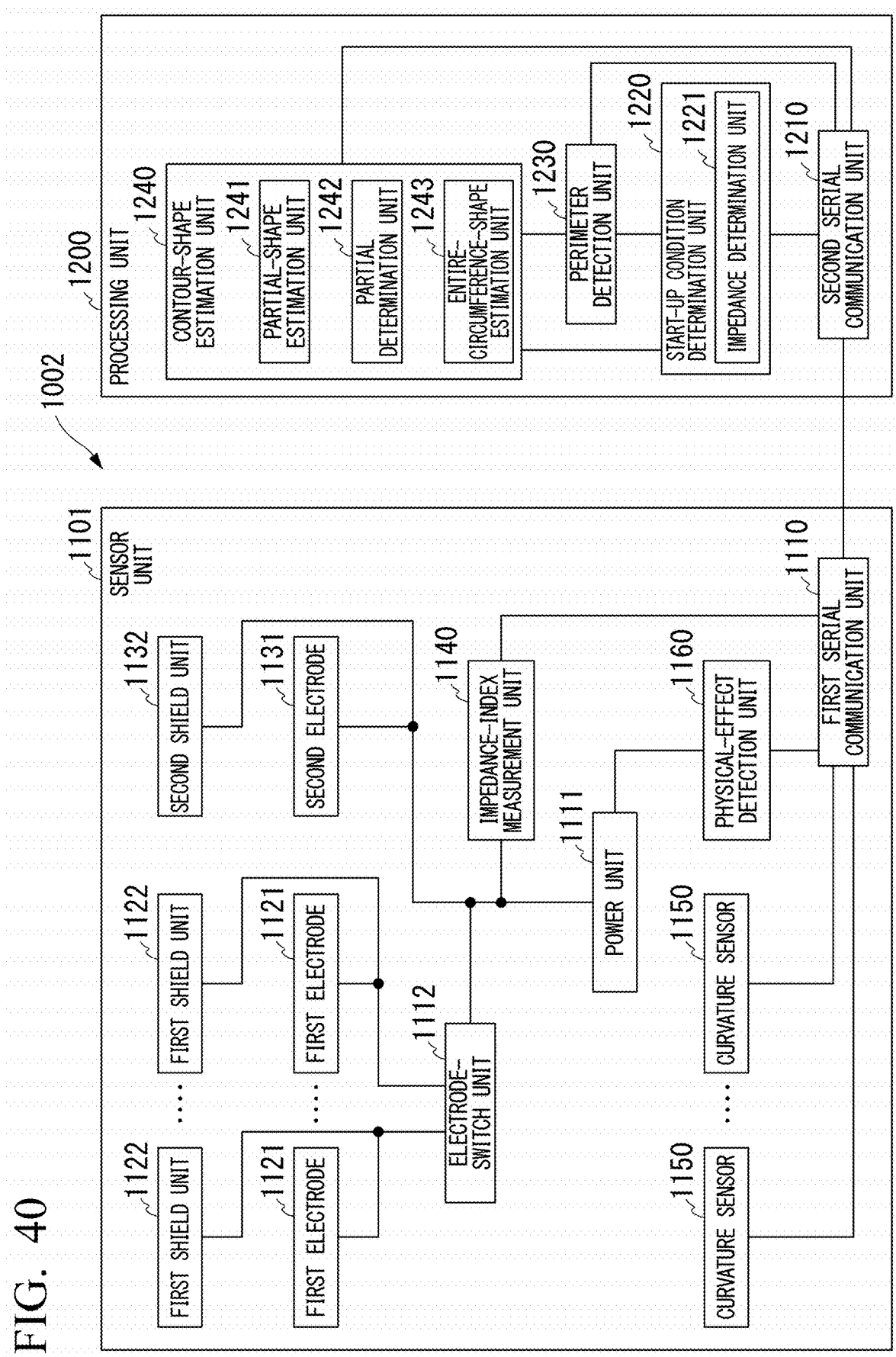
FIG. 40 is a schematic block diagram showing functional configurations of a contour shape estimation device according to a modification of the fourth embodiment of the present invention.

FIG. 40 is a schematic block diagram showing the functional configurations of a contour-shape estimation device according to a modification of the fourth embodiment of the present invention. As shown in FIG. 40, a contour-shape estimation device 1002 has a sensor unit 1101 and a processing unit 1200. The sensor unit 1101 has a first serial communication unit 1110, a power unit 1111, an electrode-switch unit 1112, first electrodes 1121, first shield units 1122, a second electrode 1131, a second shield unit 1132, an impedance-index measurement unit 1140, curvatures sensors 1150, and a physical-effect detection unit 1160. The processing unit 1200 has a second serial communication unit 1210, a start-up condition determination unit 1220, a perimeter detection unit 1230, and a contour-shape estimation unit 1240. The start-up condition determination unit 1220 has an impedance determination unit 1221. The contour-shape estimation unit 1240 has a partial-shape estimation unit 1241, a partial determination unit 1242, and an entire-circumference-shape estimation unit 1243.

In FIG. 40, the configurations having the same functions with those disclosed FIG. 33 are assigned with the same reference numerals (1110, 1121, 1131, 1140, 1150, 1160, 1200, 1210, 1220, 1221, 1230, 1240-1243) and the descriptions are omitted.

In the contour-shape estimation device 1002 is different from the contour-shape estimation device 1 in the point of having the first shield units 1122 and the second shield unit 1132.

In the contour-shape estimation device 1002, the configuration of the belt main body 1010, the arrangement of the flexible substrate 1020 and the circuit substrate 1030 in the belt main body 1010, and the arrangement of the first electrodes 1121, the second electrode 1131, the curvature sensors 1150, and the connector 1031 are the same as the description referring to FIGS. 29-32, thus the description in detail will be omitted.

Figure 41:
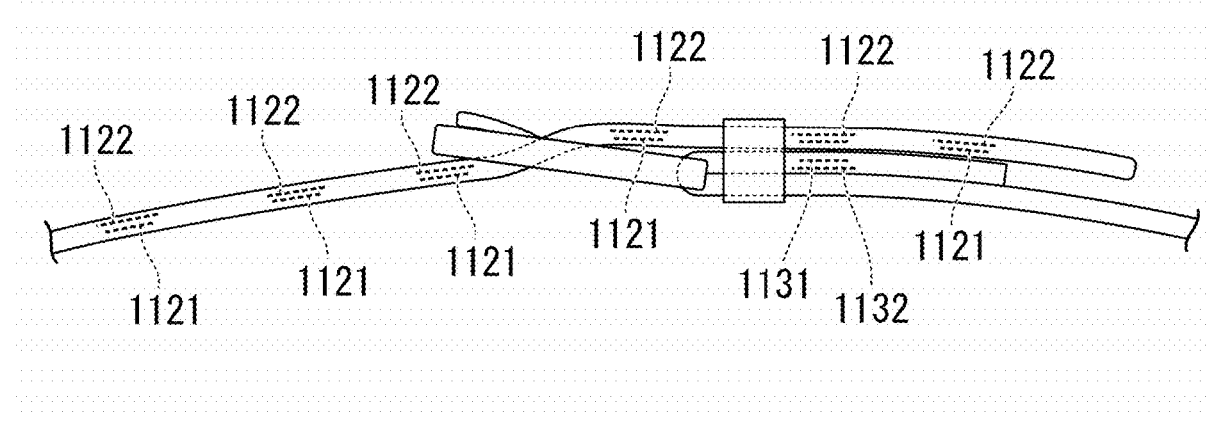
FIG. 41 is a view showing a configuration example of a first shield portion and a second shield portion according to the modification of the fourth embodiment.

FIG. 41 is a view showing a configuration example of disposing the first shield unit 1122 and the second shield unit 1132. In the same figure, the positional relationship between the first electrodes 1121 and the first shield units 1122, and a positional relationship between the second electrode 1131 and the second shield unit 1132 are shown, when the user views the belt main body 1010 from above (at the side of the user's face) in the state in which the contour-shape estimation device 1002 (belt main body 1010) is attached to the user.

As shown in FIG. 41, the first shield units 1122 are arranged in either of the front or the back of the belt main body 1010 such that the first shield units 1122 are disposed at one side of the first electrodes 1121 respectively with respect to the belt main body 1010. The second shield unit 1132 is disposed at the other side of the second electrode 1131 with respect to the belt main body 1010.

More specifically, as shown in FIG. 41, in the case in which the first electrodes 1121 opposite to the second electrode 1131, the first shield units 1122 and the second shield unit 1132 are arranged so as to sandwich the first electrodes 1121 and the second electrode 1131. As shown in FIG. 41, in the case in which the second electrode 1131 is disposed at the inner side of the first electrode 1121 when viewed by the user, each first shield unit 1122 is disposed at the outer side of each first electrode 1121 so as to face the first electrode 1121, and the second shield unit 1132 is disposed at the inner side of the second electrode 1131 so as to face the second electrode 1131.

On the other hand, in the case in which the second electrode 1131 is disposed at the outer side of the first electrode 1121 when viewed by the user, each first shield unit 1122 is disposed at the inner side of each first electrode 1121 so as to face the first electrode 1121, and the second shield unit 1132 is disposed at the outer side of the second electrode 1131 so as to face the second electrode 1131.

Figure 42:
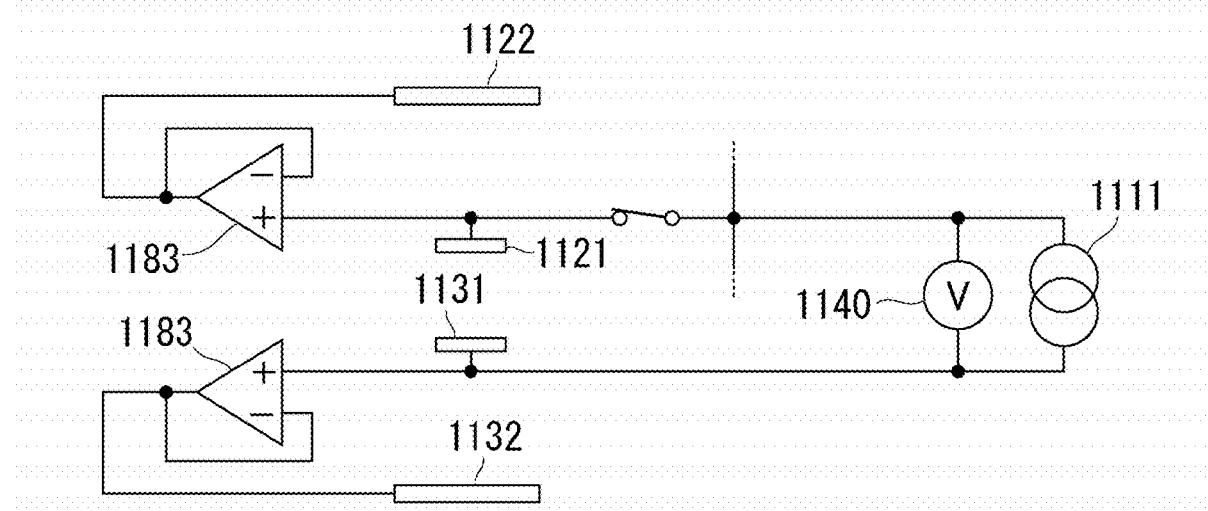
FIG. 42 is a view showing a circuit configuration example for applying voltages to the first shield portion and the second shield portion according to the modification of the fourth embodiment.

FIG. 42 is a view showing the example of the circuit configuration for applying voltages to the first shield units 1122 and the second shield unit 1132.

In the example shown in FIG. 42, the AC voltage from the power supply 1111 is applied on the first electrodes 1121 and the second electrode 1131, the impedance-index measurement unit 1140 is configured to measure the index values indicating the impedance between each first electrode 1121 and the second electrode 1131.

In FIG. 42, the voltage applied on the first electrode 1121 and the second electrode 1131 is also applied on the operational amplifiers 1183. The operational amplifier 1183 at the first electrode 1121 side is connected to the first shield unit 1122, and the operational amplifier 1183 at the second electrode 1131 side is connected to the second shield unit 1132. The operational amplifiers 1183 are configured to adjust the amplitude of the voltage while maintaining the phase of the voltage supplied from the power supply 1111.

In FIG. 42, among the plurality of first electrodes 1121, the electrode 1121 facing the second electrode 1131 is shown. With regard to the other first electrodes 1121, as same as the case shown in FIG. 42, the operational amplifier 1183 and the first shield unit 1122 are provided.

According to the configuration shown in FIG. 42, the voltage with the same phase as the voltage applied on the first electrode 1121 is applied on the first shield unit 1122. The voltage with the same phase as the voltage applied on the second electrode 1131 is applied on the second shield unit 1132. The power supply 1111 applying such voltages is considered to be the example of the voltage application unit.

The voltages with the same phase are applied on the first shield unit 1122 and the first electrode 1121 such that the first shield unit 1122 is configured to operate as an active shield for restricting the flow of the electromagnetic field from the first electrode 1121. Accordingly, the electromagnetic field from the first electrode 1121 is caused to flow to the second electrode 1131 side (opposite side of the first shield unit 1122). Similarly, the voltages with the same phase are applied on the second shield unit 1132 and the second electrode 1131 such that the second shield unit 1132 is configured to operate as the active shield for restricting the flow of the electromagnetic filed from the second electrode 1131. Accordingly, the electromagnetic filed from the second electrode 1131 is caused to flow to the first electrode 1121 side (opposite side of the second shield unit 1132).

The electromagnetic filed from the first electrode 1121 flows to the second electrode 1131 side and the electromagnetic filed from the second electrode 1131 flows to the first electrode 1121 side such that the impedance between the first electrode 1121 and the second electrode 1131 becomes less. Accordingly, improvement of the determination precision by the impedance determination unit 1221 can be expected. Thus, improvement of the perimeter detection precision by the perimeter detection unit 1230 can also be expected. Specifically, even in the case of the power supply having a relative low voltage, the impedance determination unit 1221 can determine with a high precision. Also, in the case of the power supply having a relative low voltage, the perimeter detection unit 1230 can detect the perimeter with a high precision.

As described above, the first shield units 1122 are arranged in either of the front or the back of the belt main body 1010 such that the first shield units 1122 are disposed at one side of the first electrodes 1121 respectively with respect to the belt main body 1010 for restricting the flow of the electromagnetic waves. The second shield unit 1132 is arranged on the other side of the second electrode 1131 with respect to the belt main body 1010 for restricting the flow of the electromagnetic waves.

Accordingly, it is possible to reduce the noise mixed into the first electrodes 1121 and the second electrode 1131, and the improvement of the determination precision of the impedance determination unit 1121 can be expected. The improvement of the detection precision by the perimeter detection unit 1230 can also be expected.

The power supply 1111 is configured to apply the AC voltages with the same phase to at least one of the first electrodes 1121 and the first shield unit 1122, and the power supply 1111 is configured to apply the AC voltages with the same phase to the second electrode 1131 and the second shield unit 1132.

Accordingly, the improvement of the determination precision by the impedance determination unit 1221 can be expected. The improvement of the detection precision by the perimeter detection unit 1230 can also be expected. Specifically, even in the case of the power supply having the relative low voltage, the impedance determination unit 1221 can determine with a high precision. Also, in the case of the power supply having a relative low voltage, the perimeter detection unit 1230 can detect the perimeter with a high precision.

According to either of the fourth embodiment and the modification, calibration with respect to the curvature sensors 1150 may be performed. For example, instead of the strain gauges, electrical resistance (resistor) with high accuracy may be configured. Electrical resistance having an assumed resistance value same as the resistance value of the strain gauge in the unbent state can be used. In order to switch the strain gauge and the electrical resistance, the strain gauge and the electrical resistance can be disposed parallely in advance, and either of the strain gauge or the electrical resistance can be selected using a switch.

In this manner, by replacing the strain gauge with the electrical resistance, it is possible to figure out the change of the detection voltage due to the difference between the expected resistance value of the strain gauge and the actual resistance value. It is possible to measure the curvatures with a higher precision using the curvature sensors 1150 by adding the change of the detection voltage to the amplifier as an offset in advance.

Also, a constant voltage power supply with high precision may be prepared in advance, and the detection voltage and the voltage from the constant voltage power supply may be switched. In this case, the constant voltage power supply indicating the assumed voltage value same as the detection voltage value of the strain gauge in the unbent state can be used.

Accordingly, it is possible to figure out the difference between the assumed detection voltage and the actual detection voltage. It is possible to measure the curvatures with a higher precision using the curvature sensors 1150 by adding the change of the detection voltage to the amplifier as the offset in advance.

Also, the curvature sensors 1150 may be bent in a known curvature by fitting the belt main body 1010 in a mold having the known curvature. In this case, the amplification (calibration curve) by the amplifier is adjusted so as to make the output of the curvature sensors 1150 to be coincide with the known curvature. Accordingly, it is possible to measure the curvatures with a higher precision using the curvature sensors 1150.

Figure 43:
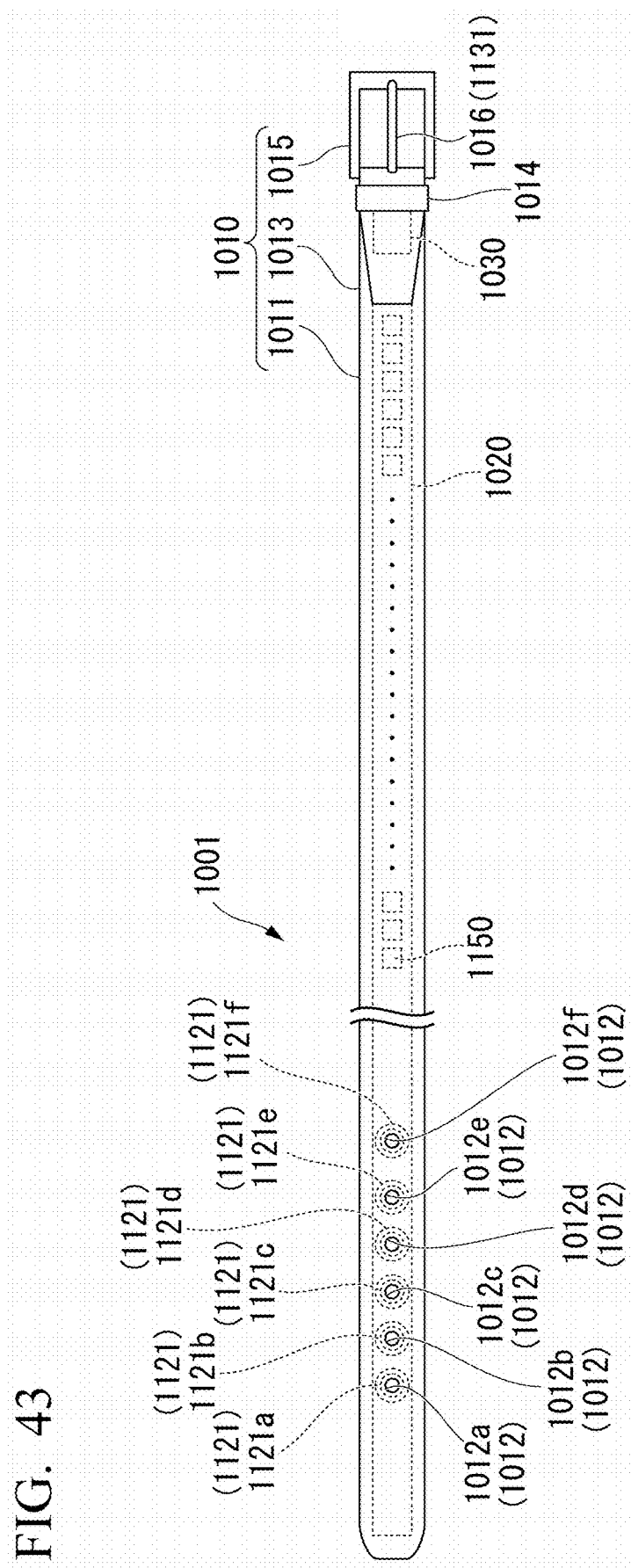
FIG. 43 is a view showing an electrode arrangement example in a case when the needle portion according to the fourth embodiment is utilized as the second electrode.

According to the fourth embodiment described above, the needle 1016 may be used as the second electrode 1131. FIG. 43 is a view showing the example of the arrangement in the case of using the needle 1016 as the second electrode 1131.

As same as described in FIGS. 29-32, in the example shown in FIG. 43, the belt main body 1010 is configured to include the belt 1011, the cosmetic case 1013, the ring 1014, and the buckle 1015, and the buckle 1015 includes the needle 1016. Also, the arrangement of the belt holes 1012, the arrangement of the flexible substrate 1020, the arrangement of the circuit substrate 1030, and the arrangement of the curvature sensors 1150 are same as the case shown in FIGS. 29-32.

On the other hand, in the example shown in FIG. 43, the arrangement of the first electrodes 1121 and the second electrode 1131 are different from that in the FIGS. 29-33. In the example shown in FIG. 43, the second electrode 1131 is disposed on the needle 1016. Specifically, the needle 1016 is configured as the second electrode 1131. The first electrodes 1121 are disposed around the belt holes 1012 respectively by every belt hole 1012.

According to the configuration shown in FIG. 43, the needle 1016 is used as the second electrode 1131 such that it is not necessary to provide the second electrode 1131 separately. In the configuration shown in FIG. 43, the same effect as the fourth embodiment described above can be achieved. Specifically, it is possible to determine whether the needle 1016 is passed through the belt hole 1012. In the case in which the needle 1016 is passed through any of the belt hole 1012, as same as described above, it is possible to detect the belt hole 1012 through which the needle 1016 is passed.

Also, it is possible to record a program for realizing the functions of the processing unit 200 on a computer-readable recording medium and causing a computer system to read and execute the program recorded on the recording medium. The computer system refers to a system including an operating system (OS) and hardware such as peripheral devices.

The computer system also refers to a homepage providing environment (or homepage displaying environment) in the case of using the WWW system.

The computer-readable recording medium refers to a removable medium such as a flexible disk, a magneto-optical disk, a read-only memory (ROM), and a compact disk read-only memory (CD-ROM), and a storage unit such as a hard disk disposed inside the computer system. Furthermore, in a case that the program is transferred through a network such as the internet and a communication line such as the telephone line, the computer-readable recording medium may refer to the communication line that is configured to maintain the program temporarily and dynamically, and in this case, the computer-readable recording medium may also refer to the device configured to maintain the program for a certain period such as a volatile memory inside the computer system used as a server or a client. The program may be a program for realizing part of the functions described above and the program may be combined with the program recorded in the computer system to realize the functions.

Fifth Embodiment

Figure 44:
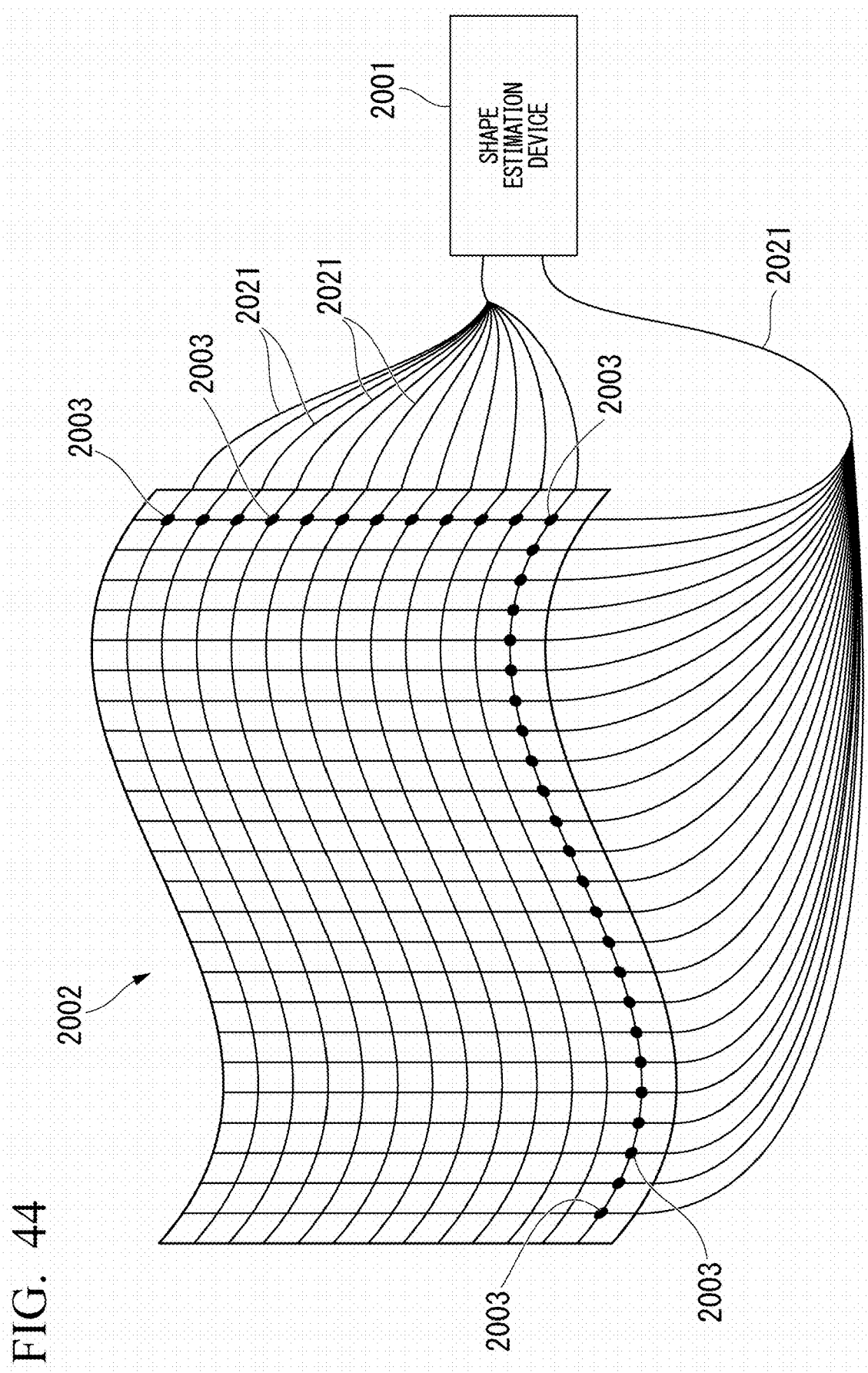
FIG. 44 is a block diagram showing a configuration of a shape estimation system according to a fifth embodiment of the present invention.

Hereinafter, a shape estimation device according a fifth embodiment of the present invention will be described. FIG. 44 is a block diagram showing a configuration of a shape estimation system according to the present embodiment. The shape estimation system shown in FIG. 44 has a shape estimation device 2001 and a sheet 2002. The sheet 2002 is made from a plurality of yarns, and the electroconductive yarns 2021 used as the base material for attaching the curvature sensors 2003 thereto are stretched horizontally and vertically. Each electroconductive yarn 2021 is insulated by using the insulation film. In the sheet 2002, for example, the electroconductive yarns 2021 are stretched horizontally and vertically by being spaced from each other with intervals. For example, if the sheet 2002 is formed in a square shape, the yarns 2021 are sewn in the vertical direction (first direction) to have the predetermined intervals and also in the horizontal direction (second direction by rotating the first direction by 90 degrees) to have the predetermined intervals. In the present embodiment, the expressions of horizontal direction and the vertical direction are used to describe, however, when the whole sheet is rotated, it is obvious that the directions in which the electroconductive yarns 2021 are stretched in the sheet 2002 are not the horizontal direction and the vertical direction. In order to make the description of the present embodiment to be simple, it is described that the electroconductive yarns 2021 are stretched in the horizontal direction and the vertical direction of the sheet. The electroconductive yarns in the first direction and the second direction may not be intersected at a 90 degrees angle.

Various curvature sensors 2003 are disposed on the sheet 2002. The curvatures sensors 2003 are disposed at the intersection points formed by the electroconductive yarns stretched in the vertical direction and the electroconductive yarns stretched in the horizontal direction. In the sheet 2002 shown in FIG. 44, it is shown that curvature sensors 2003 are disposed only on a part of the intersection points of the electroconductive yarns 2021 by omitting some reference numerals of the curvature sensor 2003, however, the curvature sensors 2003 may be disposed on all of the intersection points. In the square-shaped sheet, the curvature sensors 2003 are configured to detect both the curvature in the vertical direction and the curvature in the horizontal direction at the positions where the curvature sensors 2003 are disposed. That is, the curvature sensors 2003 may have two sensors inside so as to detect the curvatures in the two axial directions including the x-axis and the y-axis. The curvature sensors 2003 are configured to output the signals indicating the curvature information having the curvature value and the ID of the curvature sensors 2003.

The signals of the curvature information detected by the curvatures sensors 2003 are input to the shape estimation device 2001 by being transmitted through the electroconductive yarns 2021 stretched in the vertical direction and the electroconductive yarns 2021 stretched in the horizontal direction, respectively. That is, the shape estimation device 2001 is configured to acquire the curvature information detected by one curvature sensor 2003 via each of the electroconductive yarn 2021 stretched in the vertical direction and the electroconductive yarn 2021 stretched in the horizontal direction. The shape estimation device 2001 is configured to determine the position of the curvature sensor 2003 in the sheet from which the curvature information is transmitted according to the identification number (ID) of the two electroconductive yarns 2021 transmitting the signals of the curvature information. The shape estimation device 2001 may also configured to read the ID of the curvature sensor 2003 which is included in the curvature information so as to specify the curvature sensor 2003. The shape estimation device 2001 is configured to determine the vertical curvature and the horizontal curvature of the curvature sensor 2003 from the curvature information. The shape estimation device 2001 is configured to estimate the shape of the sheet 2002 according to the curvature information of all the curvature sensors 2003 disposed on the sheet 2002. In a state in which the sheet 2002 is covered on the object, the shape estimation device 2001 can estimate the shape of the covered object. In the state in which the sheet 2002 is covered on the object, when different regions of the sheet 2002 are superimposed with each other, the information of the curvature sensors 2003 disposed on the upper side or the lower side in the superimposed regions may be removed.

Figure 45:
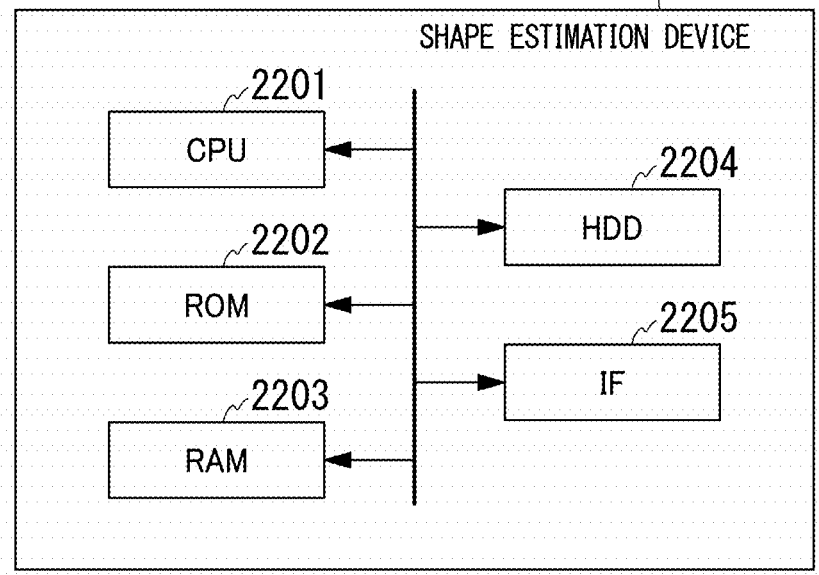
FIG. 45 is a view showing the hardware configuration of a shape estimation device according to the fifth embodiment.

FIG. 45 is a view showing a hardware configuration of the shape estimation device 2001.

The shape estimation device 2001 is a computer configured by various hardware including a Central Processing Unit (CPU) 2201, a Read Only Memory (ROM) 2202, a Random Access Memory (RAM) 2203, a Hard Disk Drive (HDD) 2204, and an Interface (IF) 2205.

Figure 46:
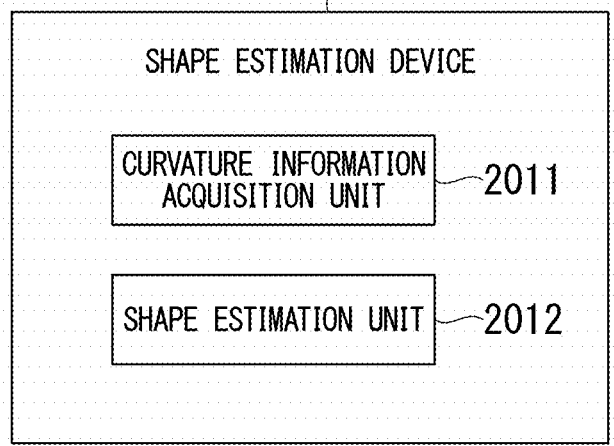
FIG. 46 is a block diagram showing functions of the shape estimation device according to the fifth embodiment.

FIG. 46 is a functional block diagram of the shape estimation device 2001.

The shape estimation device 2001 has the ROM 2202 and the HDD 2204 in which the shape estimation program is recorded. The CPU 2201 of the shape estimation device 2001 is configured to read the shape estimation program and execute the program according to the operation of the user. When the CPU 2201 of the shape estimation device 2001 executes the shape estimation program, the shape estimation device 2001 is provided with the functions of the curvature information acquisition unit 2011 and the shape estimation unit 2012.

The curvature information acquisition unit 2011 is configured to acquire the curvature information of each curvature sensor 2003 provided in the sheet 2002.

The shape estimation unit 2012 is configured to estimate the shape of the sheet 2002 according to the curvature information.

Figure 47:
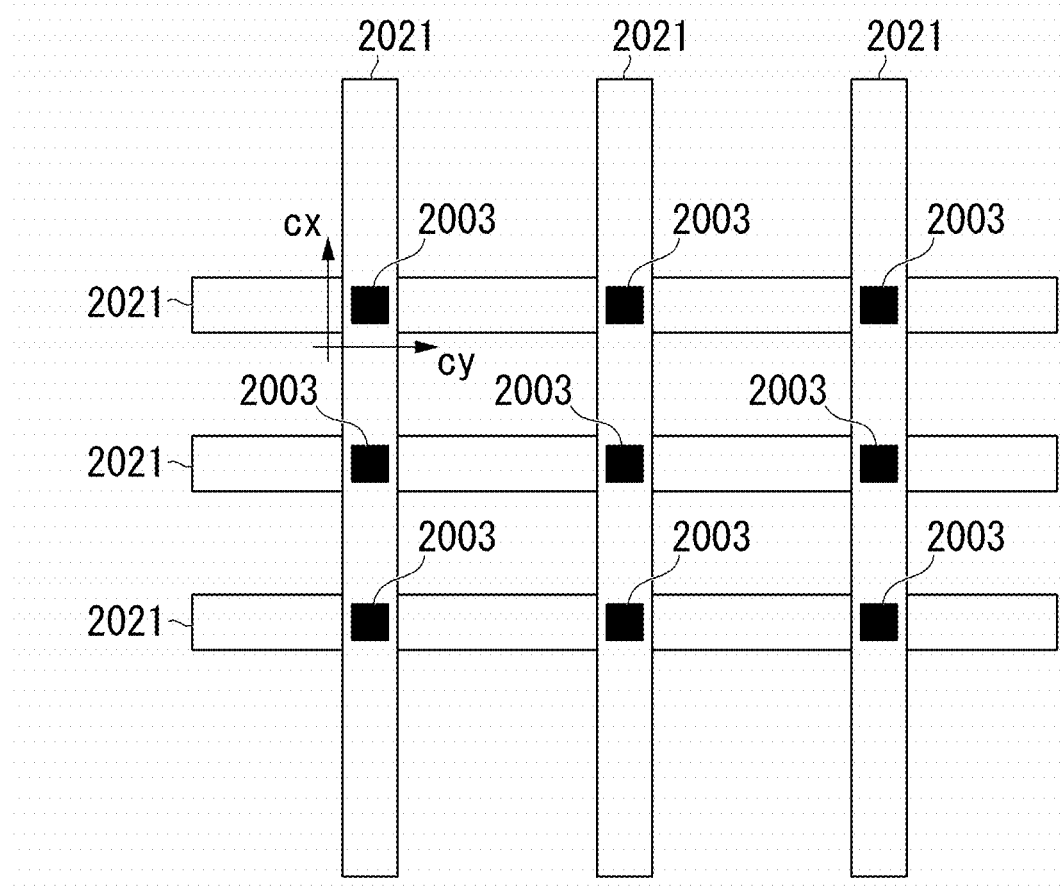
FIG. 47 is an enlarged view showing a sheet according to the fifth embodiment.

FIG. 47 is an enlarge view of the sheet 2002. In the enlarge view of the sheet 2002 shown in FIG. 47, only the positional relationship of the electroconductive yarns 2021 and the curvature sensors 2003 are shown. For example, the curvature sensors 2003 may be provided at the intersection points formed by the electroconductive yarns stretched in the horizontal direction and the electroconductive yarns stretched in the vertical direction. The yarns made from fibers without electrical conductivity such as the cotton, the silk and the like, or other synthetic fibers may be sewn among the electroconductive yarns 2021 to form the sheet 2002. As described above, the curvature sensors 2003 are configured to output the curvature information including the detected curvatures values and the IDs of the curvatures sensors 2003 to the shape estimation device 2001 via the electroconductive yarns 2021. The curvature sensors 2003 may output the curvature information indicating the curvature values in the vertical direction via the electroconductive yarns 2021 stretched in the vertical direction, and the curvature sensors 2003 may output the curvature information indicating the curvature values in the horizontal direction via the electroconductive yarns 2021 stretched in the horizontal direction. The curvature sensors 2003 may be configured by the conventional known technology. The curvature values included in the curvature information are the curvatures in the vertical direction or in the horizontal direction at the positions at which the curvatures are disposed. The curvature in the vertical direction is regarded as cy, and the curvature in the horizontal direction is regarded as cx.

In FIG. 47, it is described that the curvature sensors 2003 are disposed at the intersection points of the electroconductive yarns 2021 which are stretched in the vertical direction and the horizontal direction, however, the curvature sensors 2003 may be disposed at other positions besides the intersection points of the electroconductive yarns 2021. The curvature sensors 2003 disposed in the electroconductive yarns 2021 in the vertical direction are configured to determine the curvatures of the vertical direction (same direction as the first direction). The curvature sensors 2003 disposed in the electroconductive yarns 2021 in the horizontal direction are configured to determine the curvatures of the horizontal direction (same direction as the second direction). When the dimension of the curvature sensor 2003 is large, the curvatures sensor 2003 may be attached to the sheet 2002 across multiple adjacent electroconductive yarns 2021.

Figure 48:
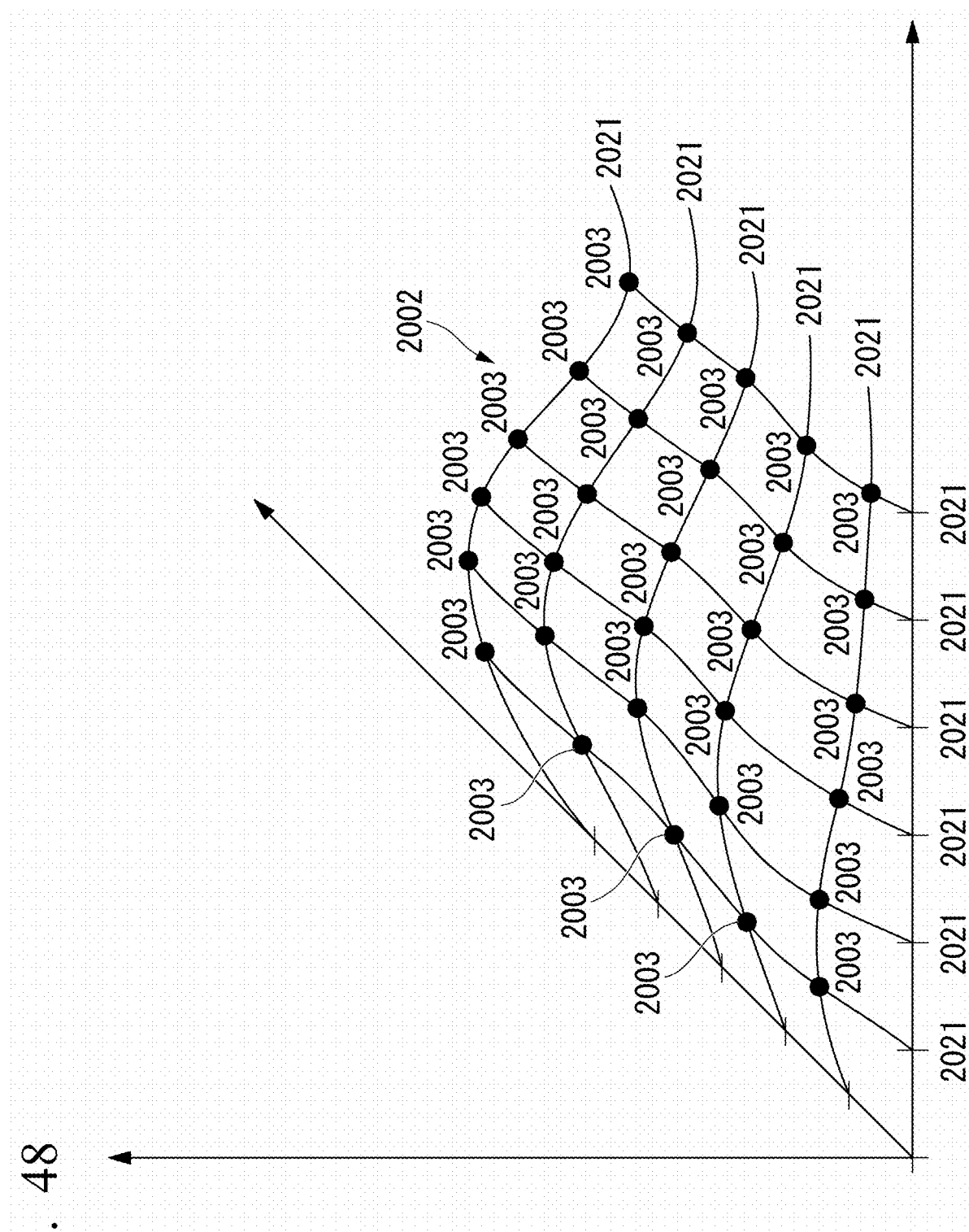
FIG. 48 is a view showing a three-dimensional waving state of the sheet in a three-dimensional coordinate system.

FIG. 48 is a view showing the sheet 2002 in an undulating state using a three-dimensional coordinate system. In the case of the sheet 2002 in the three-dimensional undulating state, each curvature sensor 2003 is configured to output the curvature information indicating the curvatures of the sheet 2002 in the vertical direction and the horizontal direction. The shape estimation device 2001 is configured to estimate the shape in the coordinate system shown in FIG. 48 according to the position of each curvature sensor 2003 in the sheet 2002, the relative positional relationship grasped in advance, and the curvature information acquired from each curvature sensor 2003.

Figure 49:
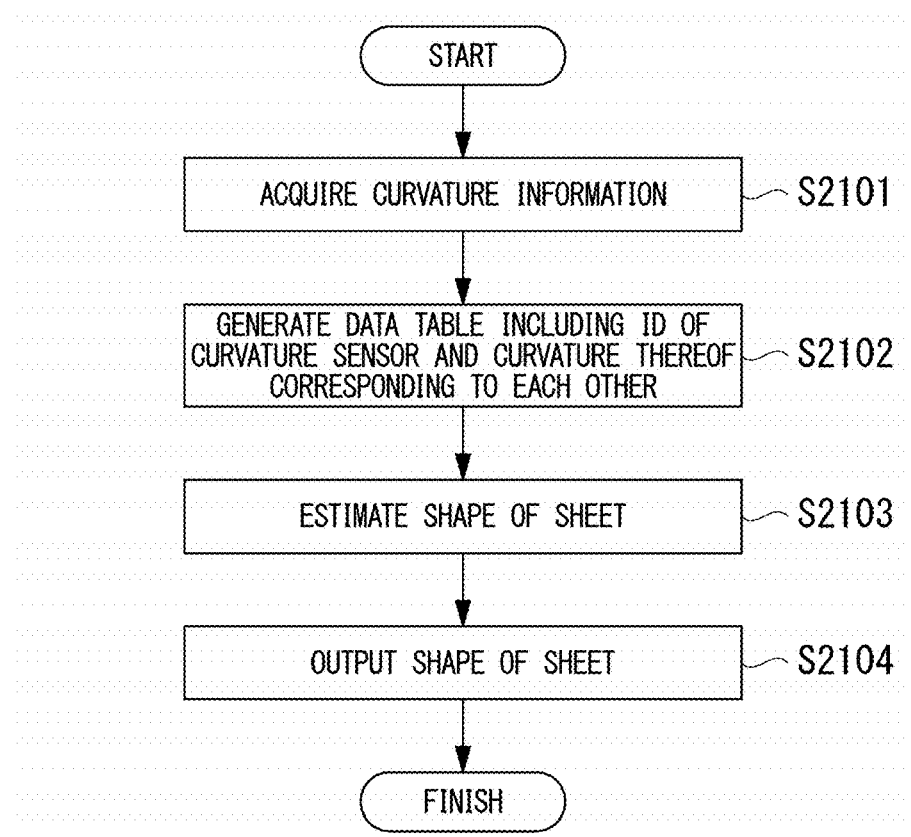
FIG. 49 is a flowchart showing processing procedures of the shape estimation device according to the fifth embodiment.

FIG. 49 is a view showing the processing flow of the shape estimation device 2001.

When the shape estimation device 2001 starts up according to the operation of the user, the power is supplied to each curvature sensor 2003 of the sheet 2002 via the electroconductive yarns 2021. The user covers the object with the sheet 2002 in such a state. Each curvature sensor 2003 outputs the curvature information including the curvature in the vertical direction cy and the curvature in the horizontal direction cx to the shape estimation device 2001. The curvature information acquisition unit 2011 of the shape estimation device 2001 acquires the curvature information (step S2101). The curvature information acquisition unit 2011 is configured to output the curvature information acquired from all the curvature sensors 2003 via the electroconductive yarns 2021 to the shape estimation unit 2012. The shape estimation unit 2012 is configured to detect the IDs of the curvature sensors 2003 and the curvatures cx, cy from the curvature information acquired via the electroconductive yarns 2021 in the vertical direction. The shape estimation unit 2012 is configured to generate a data table by associating the IDs of the curvatures sensors 2003 with the curvatures cx, cy (Step S2102). The shape estimation unit 2012 finishes the generation of the data table by writing all the IDs of the curvature sensors 2003 and the curvatures cx, cy into the data table.

Subsequently, the shape estimation unit 2012 is configured to acquire the curvatures cx, cy of each curvature sensor 2003 from the data table. The shape estimation unit 2012 is configured to memorize the intervals between the curvature sensors 2003 in advance. The shape estimation unit 2012 is configured to estimate the shape of the sheet 2002 in the three-dimensional coordinate system shown in FIG. 48 using the curvatures cx, cy of each curvature sensor 2003 and the values of the intervals between the curvature sensors 2003 (Step S2103). When the shape estimation unit 2012 has estimated the shape of the sheet 2002, the shape estimation unit 2012 outputs the estimated shape on the display unit such as the monitor (Step S2104).

The sheet 2002 may be used to configure clothes. Also, the sheet 2002 may be used to configure the cloth of a specified region of the clothes only. In this case, the shape estimation unit 2012 can detect and output the shape and the movement of the body part of the person wearing the clothes (the object dressed in the clothes) to the display portion of the monitor. For example, it is possible to detect whether the left arm or the right arm has raised.

Sixth Embodiment

Next, a motion detection device according to a sixth embodiment of the present invention will be described.

Figure 51:
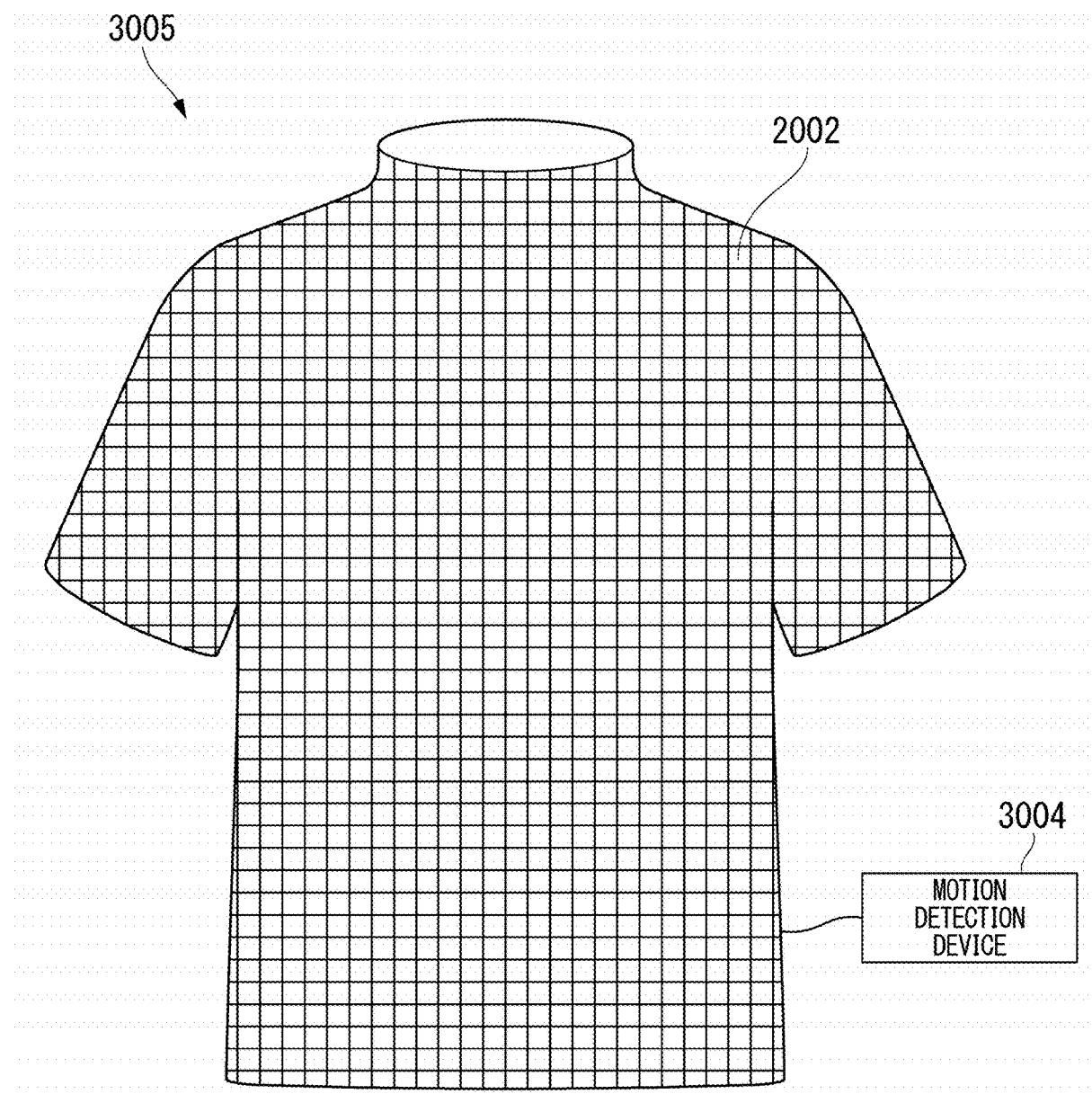
FIG. 51 is a view showing clothes configured by a sheet according to the sixth embodiment.

FIG. 51 is a view showing the functional blocks of the motion detection device 3004 according to the present embodiment. The hardware configuration of the motion detection device 3004 is the same as the hardware configuration of the shape estimation device 2001 shown in FIG. 45 according to the fifth embodiment described above.

The motion detection program is recorded in the ROM 2202 and the HDD 2204 of the motion detection device 3004. The CPU 2201 of the motion detection device 3004 is configured to read the motion detection program and execute the program according to the operation of the user. When the CPU 2201 of the motion detection device 3004 executes the motion detection program, the motion detection device 3004 is provided with the functions of the curvature information acquisition unit 3041, the shape estimation unit 3042, and the motion detection unit 3043.

The curvature information acquisition unit 3041 is configured to acquire the curvature information of each curvature sensor 2003 provided in the clothes configured by the sheet 2002.

The shape estimation unit 3042 is configured to estimate the shape of the clothes according to the curvature information.

The motion detection unit 3043 is configured to detect the motion of the object such as the person dressed in the clothes according to the shape of the clothes.

Figure 52:
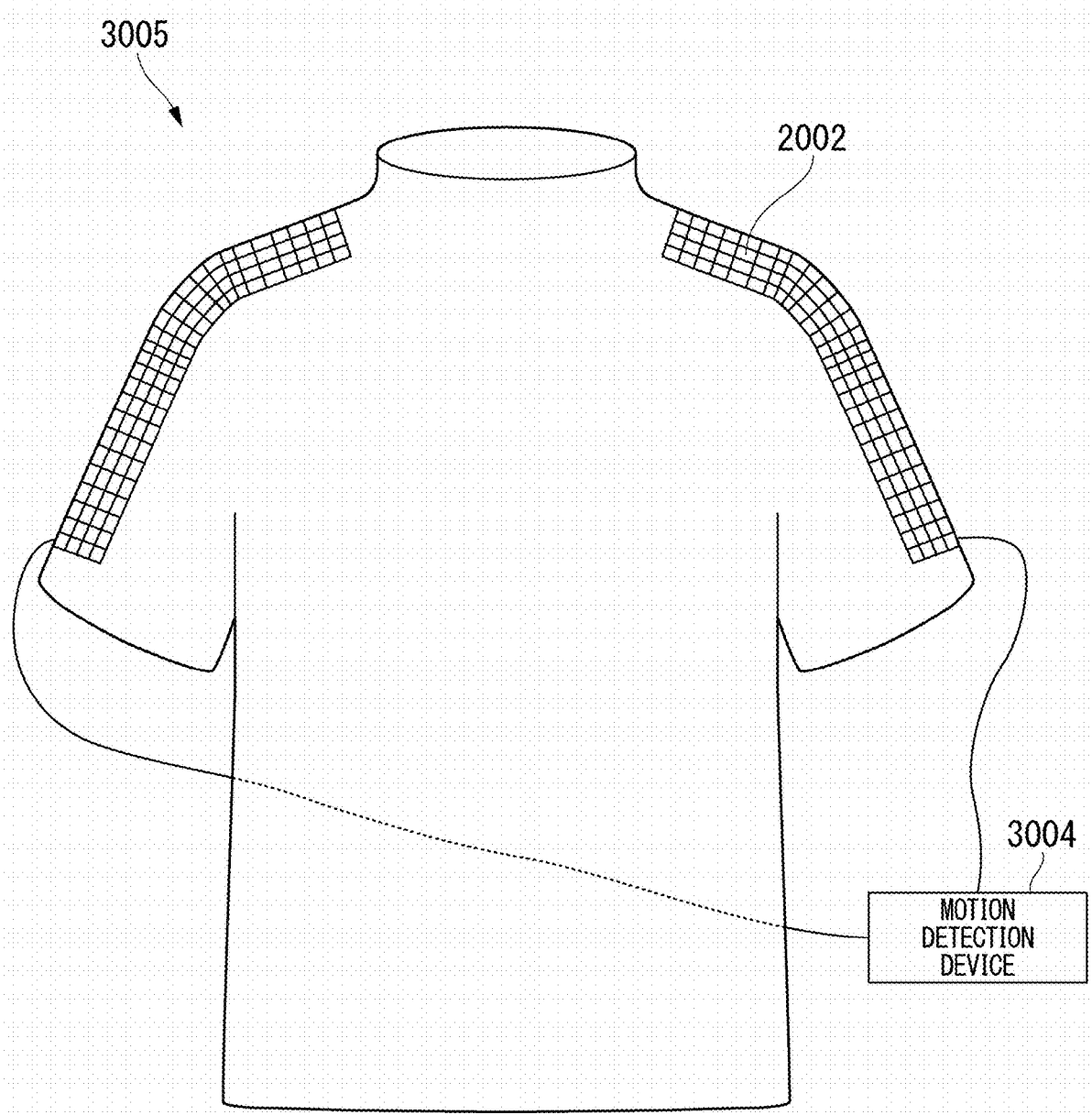
FIG. 52 is a view showing clothes having a specific region configured by the sheet according to the sixth embodiment.

FIG. 51 is a view showing the clothes configured by the sheet 2002. FIG. 52 is a view showing the clothes having a specified region configured by the sheet 2002.

In the case in which the entire clothes 3005 are configured by the sheet 2002, the electroconductive yarns 2021 are disposed and stretched around the entire clothes 3005. Although it is not shown in FIG. 51, the curvature sensors 2003 are disposed at the intersection points of the electroconductive yarns 2021. The electroconductive yarns 2021 are connected to the motion detection device 3004. In the case in which the person moves while wearing the clothes 3005, the motion detection device 3004 can detect the motion of the person according to the shape of the clothes 3005.

As shown in FIG. 52, the specified region of the clothes 3005 may be configured by the sheet 2002. The electroconductive yarns 2021 are disposed and stretched around the specified region. In the same manner shown in FIG. 51, although it is not shown in FIG. 52, the curvature sensors 2003 are disposed at the intersection points of the electroconductive yarns 2021. The electroconductive yarns 2021 are connected to the motion detection device 3004. When the person moves while wearing the clothes 3005, for example, in the case in which the region near the shoulder part of the clothes 3005 is configured by the sheet 2002, the motion detection device 3004 can detect the raising and lowering of the arms of the person according to the shape of the sheet 2002 close to the shoulder part.

Figure 53:
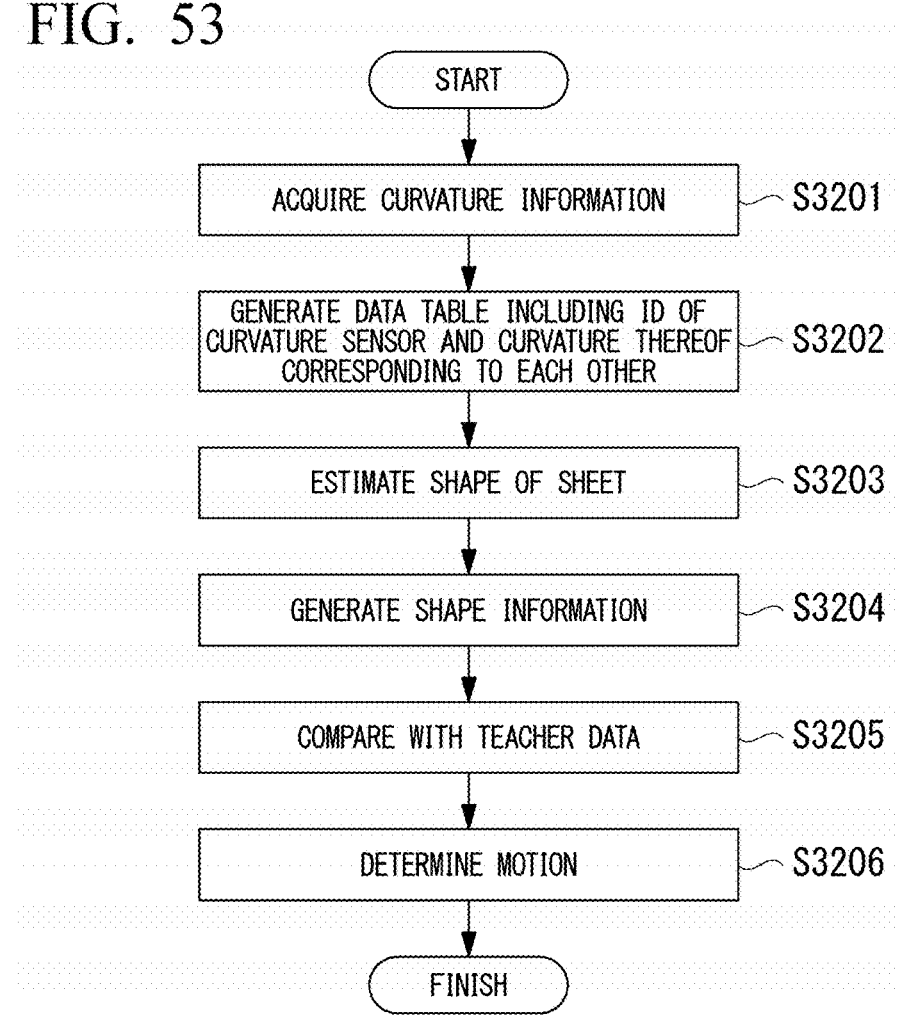
FIG. 53 is a flowchart showing processing procedures of the movement detection device according to the sixth embodiment.

FIG. 53 is a view showing the processing flow of the motion detection device 3004 according to the present embodiment.

When the motion detection device 3004 starts up according to the user operation, the power is supplied to each curvature sensor 2003 of the clothes 3005 via the electroconductive yarns 2021. Each curvature sensor 2003 is configured to output the curvature information including the curvature cy in the vertical direction and the curvature cx in the horizontal direction to the motion detection device 3004 according to the motion of the user wearing the clothes 3005. The curvature information acquisition unit 3041 of the motion detection device 3004 is configured to acquire the curvature information (Step S3201). The curvature information acquisition unit 3041 is configured to output the curvature information acquired from the whole curvature sensors 2003 via the electroconductive yarns 2021 to the shape estimation unit 3042. The shape estimation unit 3042 is configured to detect the IDs of the curvature sensors 2003 and the curvatures cx, cy from the curvature information acquired via the electroconductive yarns 2021 in the vertical direction. The shape estimation unit 3042 is configured to generate a data table by associating the IDs of the curvatures sensors 2003 with the curvatures cx, cy (Step S3202). The shape estimation unit 3042 finishes the generation of the data table by writing all the IDs of the curvature sensors 2003 and the curvatures cx, cy into the data table.

Subsequently, the shape estimation unit 3042 acquires the curvatures cx, cy of each curvature sensor 2003 from the data table. The shape estimation unit 3042 is configured to memorize the intervals between the curvature sensors 2003 in advance. The shape estimation unit 3042 is configured to estimate the shape of the clothes 3005 in the three-dimensional coordinate system using the curvatures cx, cy of each curvature sensor 2003 and the values of the intervals between the curvature sensors 2003 (Step S3203). The shape estimation unit 3042 is configured to estimate the shape of the clothes 3005 and generates the information of the shape thereof (Step S3204). The shape estimation unit 3042 outputs the shape information to the motion detection unit 3043. The shape information acquired by the motion detection unit 3043 may be the 3D modeling data of the shape of the clothes 3005 acquired from the curvatures of each curvature sensor 2003, and the shape information may be the information indicating the corresponding relationship between the IDs and the curvature values of each curvature sensor 2003 disposed on the clothes. In the case in which the shape information is the 3D modeling data, for example, the motion detection unit 3043 is configured to compare the shape information with the 3D modeling teacher data corresponding to the motion of different person which is recorded in the data base (Step S3205). The motion detection unit 3043 compares the shape information with the 3D modeling teacher data, and in the case in which the shape information coincides with the teacher data, the motion detection unit 3043 determines that the motion indicated by the teacher data has been performed (Step S3206). The motion detection unit 3043 may output the determination result to the monitor or other device. The motion detection unit 3043 may only output the acquired shape information of the clothes to the monitor and the like.

According to the motion detection device 3004 according to the present embodiment described above, it is possible to figure out the motor function due to the accumulation of the motion information of the person wearing the clothes 3005.

In the case in which the person wearing the clothes 3005 is a caregiver, the motion detection device 3004 can be applied in the care assistance due to the motion detection. For example, it is possible to detect the problems during the care operation.

In the case in which the person wearing the clothes 3005 is a driver of a vehicle, it is possible to record the operation history indicating the driving operations.

In the case in which the person wearing the clothes 3005 is a labor, it is possible to perform the labor management such as preventing the machine operation accident and the like.

Further, the motion detection device 3004 may be configured to detect the motions of an animal wearing the clothes. Accordingly, it is possible to accumulate the motion information of the animal.

Seventh Embodiment

Next, a scanning device according to a seventh embodiment of the present invention will be described.

Figure 54:
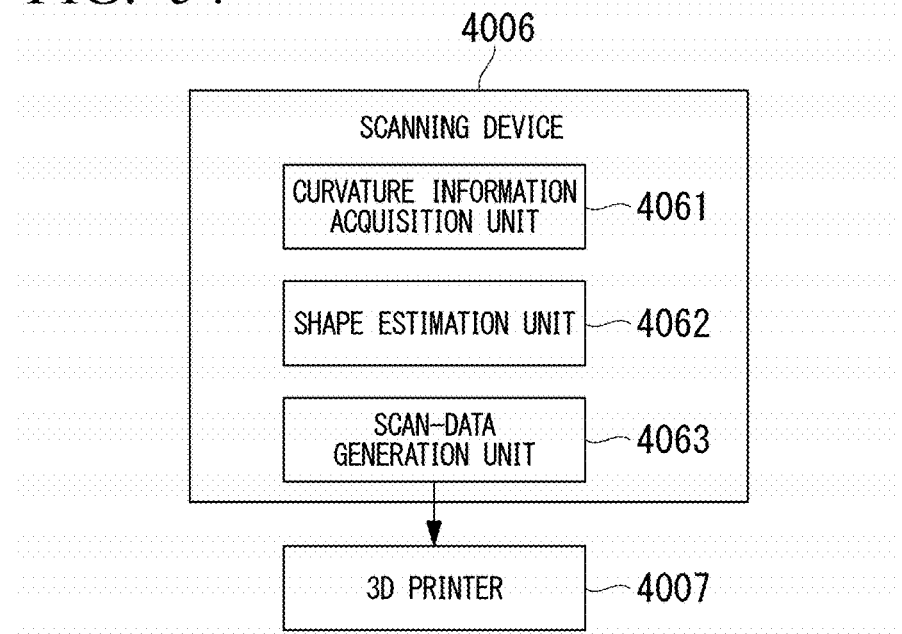
FIG. 54 is a block diagram showing functions of a scanning device according to a seventh embodiment of the present invention.

FIG. 54 is a functional block diagram of the scanning device 4006 according to the present embodiment. The hardware configuration of the scanning device 4006 is the same as the hardware configuration of the shape estimation device 2001 according to the fifth embodiment shown in FIG. 45.

The scanning program is recorded in the ROM 2202 and the HDD 2204 of the scanning device 4006. The CPU 2201 of the scanning device 4006 is configured to read the scanning program and execute the program according to the operation of the user. When the CPU 2201 of the scanning device 4006 executes the scanning program, the scanning device 4006 is provided with the functions of the curvature information acquisition unit 4061, the shape estimation unit 4062, and the scan-data generation unit 4063.

The curvature information acquisition unit 4061 is configured to acquire the curvature information of each curvature sensor 2003 provided in the sheet 2002.

The shape estimation unit 4062 is configured to estimate the shape of the sheet 2002 according to the curvature information.

The scan-data generation unit 4063 is configured to generate the three-dimensional scan data according to the shape of the sheet 2002.

Instead of the shape estimation device 2001 according to the fifth embodiment shown in FIG. 44, the scanning device 4006 is connected to the sheet 2002 via the electroconductive yarns 2021.

As shown in FIG. 54, the scanning device 4006 may be connected to the 3D-printer 4007 by communication. In this case, the scan-data generation unit 4063 is configured to output the generated three-dimensional scan data to the 3D-printer 4007.

Figure 55:
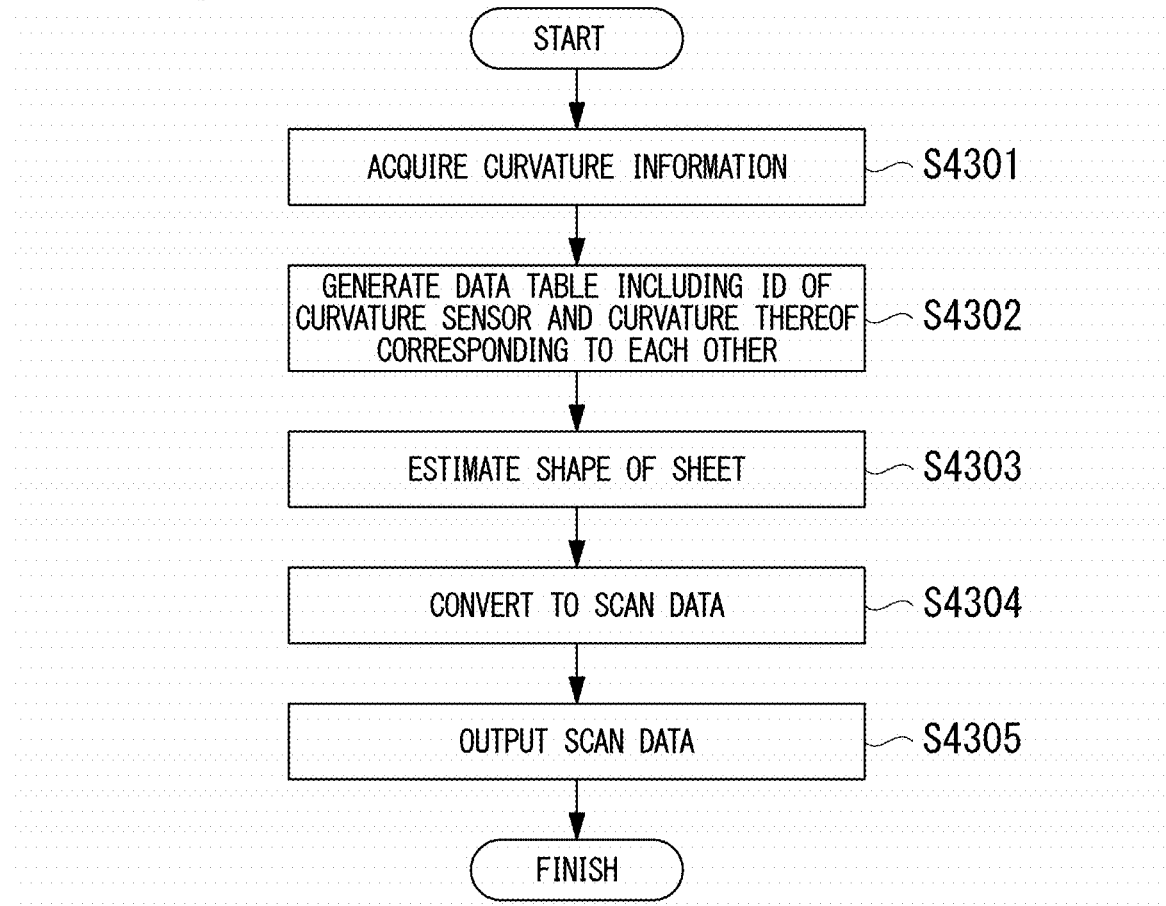
FIG. 55 is a flowchart showing processing procedures of the scanning device according to the seventh embodiment.

FIG. 55 is a view showing the processing flow of the scanning device 4006 according to the present embodiment.

When the scanning device 4006 starts up according to the user operation, the power is supplied to each curvature sensor 2003 of the sheet 2002 via the electroconductive yarns 2021. In this state, the user covers the object with the sheet 2002. Each curvature sensor 2003 is configured to output the curvature information including the curvature cy in the vertical direction and the curvature cx in the horizontal direction to the scanning device 4006. The curvature information acquisition unit 4061 of the scanning device 4006 is configured to acquire the curvature information (Step S4301). The curvature information acquisition unit 4061 is configured to output the curvature information acquired from the whole curvature sensors 2003 via the electroconductive yarns 2021 to the shape estimation unit 4062. The shape estimation unit 4062 is configured to detect the IDs of the curvature sensors 2003 and the curvatures cx, cy from the curvature information acquired via the electroconductive yarns 2021 in the vertical direction. The shape estimation unit 4062 is configured to generate a data table by associating the IDs of the curvatures sensors 2003 with the curvatures cx, cy (Step S4302). The shape estimation unit 4062 finishes the generation of the data table by writing all the IDs of the curvature sensors 2003 and the curvatures cx, cy into the data table.

The shape estimation unit 4062 acquires the curvatures cx, cy of each curvature sensor 2003 from the data table. The shape estimation unit 4062 is configured to memorize the intervals between the curvature sensors 2003 in advance. The shape estimation unit 4062 is configured to estimate the shape of the sheet 2002 in the three-dimensional coordinate system using the curvatures cx, cy of each curvature sensor 2003 and the values of the intervals between the curvature sensors 2003 (Step S4303). The shape estimation unit 4062 is configured to estimate the shape of the sheet 2002 and outputs the 3D modeling data indicating the shape thereof to the scan-data generation unit 4063. The scan-data generation unit 4063 is configured to covert the 3D modeling data into the scan data with the format that can be handled by the 3D-printer 4007 (Step S4304). The scan-data generation unit 4063 outputs the scan data to the 3D-printer 4007 (Step S4305). The 3D-printer 4007 performs the printing operation according to the acquired scan data.

According to the above processing, the scanning device 4006 can generate the scan data corresponding to the shape of the covered object by covering the object with the sheet 2002 only. In the case in which the clothes 3005 is configured by from the sheet 2002, the scanning device 4006 can generate the scan data of the body in motion of the user wearing the clothes 3005.

According to the fifth embodiment to the seventh embodiment of the present invention described above, the example of disposing the curvature sensors 2003 in the sheet 2002 is described, however, the present invention is not limited thereto. For example, as shown in FIG. 56, the shape estimation device 2001, the motion detection device 3004, and the scanning device 4006 may be configured to have a curvature-sensor-mounting base member 8 instead of the sheet 2002.

Figure 56:
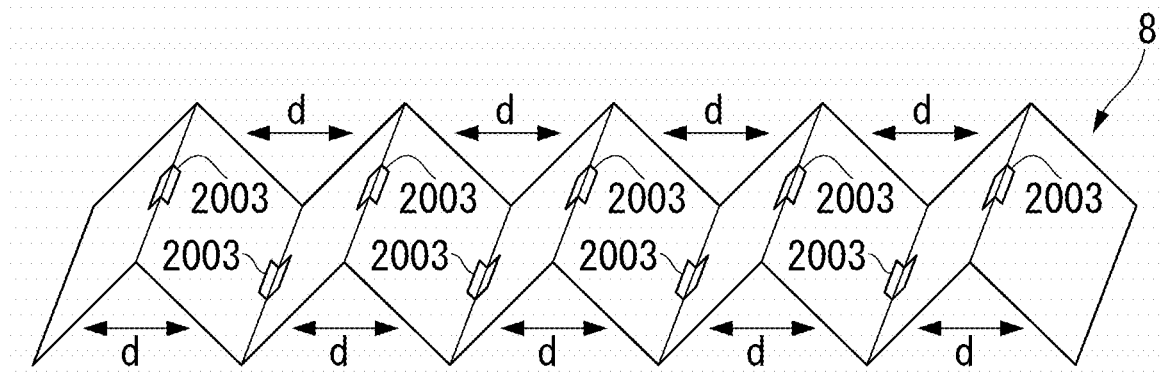
FIG. 56 is a view showing a first example of a curvature-sensor-attaching substrate according to the above-mentioned embodiments.

FIG. 56 is a first view showing the configuration example of the curvature-sensor-mounting base member 8. Hereinafter, the curvature-sensor-mounting base member 8 shown in FIG. 56 will be referred to the first base member 8. The first base member 8 shown in FIG. 56, for example, is configured from the materials such as the vinyl chloride, the plastic, and the like. The first base member 8 is configured by connecting the short sides of plate members having rectangular shapes such that the plate members are bendable with respect to each other. According to the structure, the first base member 8 can be extended and contracted along the direction of connecting the plate members. In FIG. 56, the arrows show the extending and contracting direction. The first base member 8 extends and contracts due to the change of the interval L between the ridgeline formed by the connected plate members and another adjacent ridgeline. The first base member 8 deforms from the linear shape to the circular arc shape when the different intervals L extend or contract by different lengths.

Figure 50:
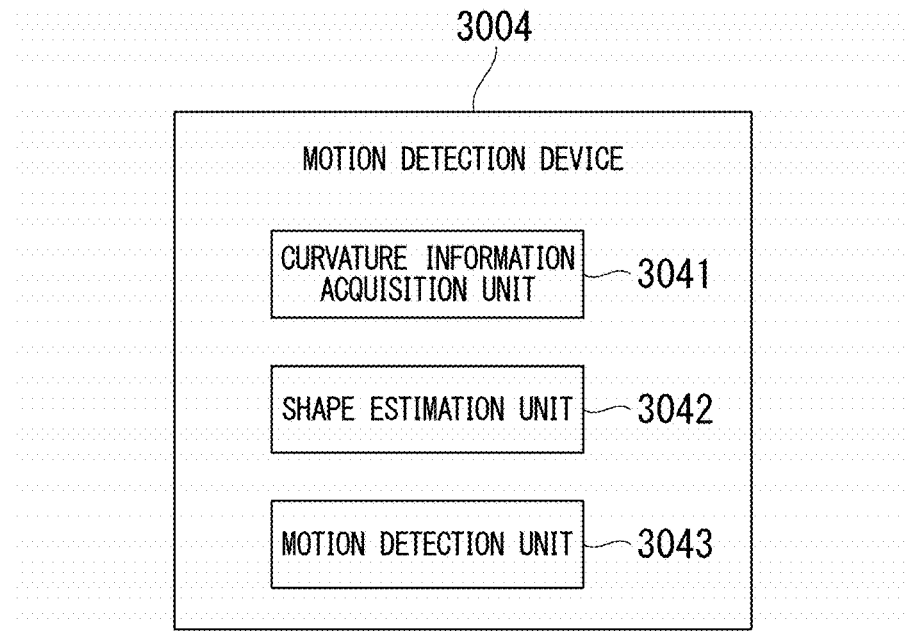
FIG. 50 is a block diagram showing functions of a movement detection device according to a sixth embodiment of the present invention.

Each curvature sensor 2003 disposed on the first base member 8 is attached to be across the plate members at the position where the plate members are connected with each other such that the curvature sensor 2003 can detect the curvature formed by the surfaces of the plate members. The curvature sensor 2003 outputs the curvature information indicating this curvature. For example, in the case in which the clothes are the body suit, as shown in FIG. 56, the first base member 8 is attached to the position for determining the shape. The attachment position of the first base member 8 is same as the region in which the sheet 2002 is disposed as shown in FIG. 48, for example, may be in the region from the shoulder to the arm. The first base member 8 may be disposed in other regions. Accordingly, the shape estimation device 2001, the motion detection device 3004, and the scanning device 4006 can estimate the shape of the body suit according to the motion of the body of the person wearing the body suit. In FIG. 50, the electroconductive yarns 2021 are not shown, however, the electroconductive yarns 2021 are disposed on the first base member 8 to be connected to each curvature sensor 2003.

As described above, in the first base member 8, the adjacent plate members are connected with each other to form the angle at the connection position, however, an arc may be formed at the connection position such that the whole of the first base member 8 has a wave shape.

In the first base member 8 described above, each curvature sensor 2003 is disposed at the center along the extending direction of the first base member 8, however, two curvature sensors 2003 may be disposed at the connection positions of the plate members in the vicinity of the left and right ends in a width direction of the plate member perpendicular to the extending direction of the first base member, respectively. In this case, when the whole first base member 8 is deformed to a swirl shape, a difference occurs between the distance d at the left side with respect to the extending direction of the first base member 8 (the distance d at the back side of the paper in FIG. 56) and the distance d at the right side (the distance d at the front side of the paper in FIG. 56). It is possible to measure the three-dimensional deformation of the first base member 8 by combining the curvature information of each curvature sensor 2003.

Figure 57B:
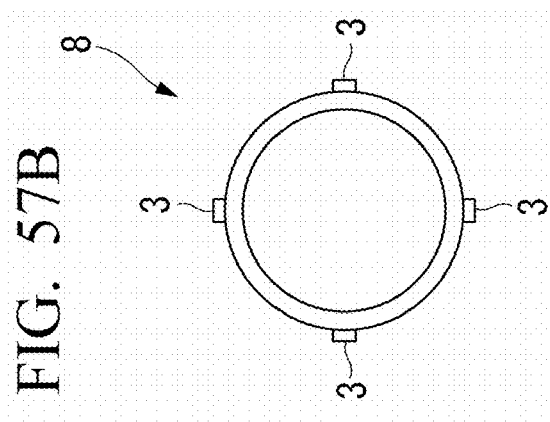
FIG. 57B is a view showing the second example of the curvature-sensor-attaching substrate according to the above-mentioned embodiments.
Figure 57A:
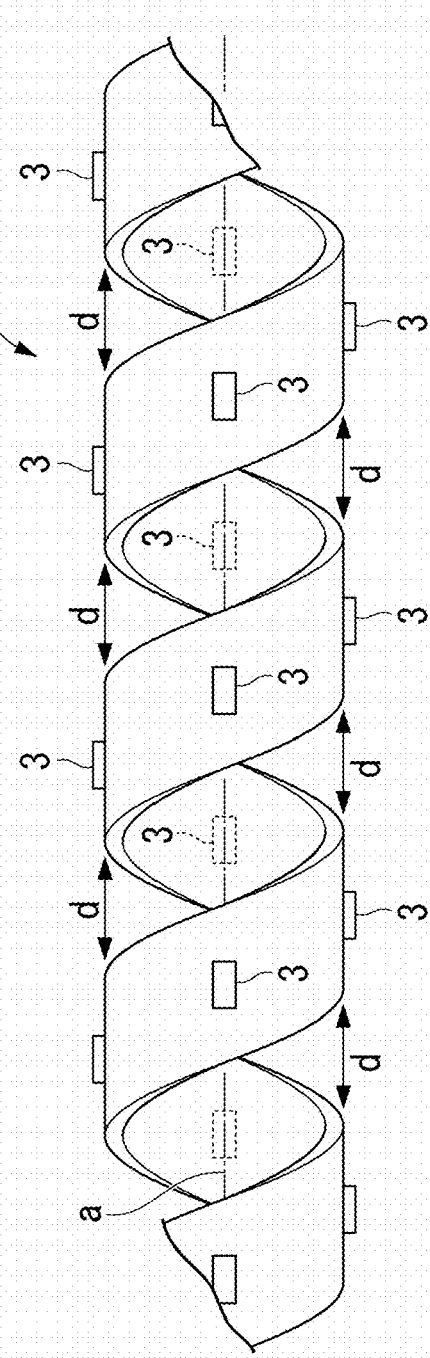
FIG. 57A is a view showing a second example of the curvature-sensor-attaching substrate according to the above-mentioned embodiments.

FIGS. 57A and 57B are views showing another example of the curvature-sensor-attachment base member.

Hereinafter, the curvature-sensor-attachment base member 9 shown in FIGS. 57A and 57B is referred to a second base member 9. The second base member 9 shown in FIGS. 57A and 57B are also made from the materials having flexibility such as the vinyl chloride, the plastic, and the like. The second base member 9 is formed in a helical shape by winding a rectangular sheet into a spiral shape around the axial line a as the center, wherein the sheet has a first side pair and a second side pair and the length of the first side pair is considerably longer that the length of the second side pair. FIG. 57A is a view showing the second base member 9 when viewed from the lateral direction with respect to the axial line a. FIG. 57B is a view showing the second base member 9 when viewed along the direction of the axial line a. According to the structure, the second base member 9 can be extended and contracted along the axial direction. The arrows in FIG. 57A show the extending and contracting direction of the second base member 9. The second base member 9 extends and contracts due to the change of the intervals L of the spiral shape. When the different intervals L extends and contracts by different lengths, the second base member 9 is deformed such that the axial line thereof changes from the linear shape to the circular arc shape.

The curvature sensors 2003 are disposed on the second base member 9 at positions where the second base member 9 is rotated by 45 degrees around the axial line as the rotation center. The curvature sensors 2003 of the second base member 9 output the curvature information indicating the curvatures. The curvature sensors 2003 of the second base member 9 may be configured to determine the curvatures in the arc direction of the circle having the axial line as the center and output the curvature information indicating the curvatures thereof. In the case such as that the clothes are the body suit, as shown in FIGS. 57A and 57B, the second base member 9 is attached to the position for determining the shape. Similar to the region in which the sheet 2002 is disposed as shown in FIG. 48, the attachment position of the second base member 9 may be the region from the shoulder to the arm. The attachment position of the second base member 9 may be in other regions. Accordingly, the shape estimation device 2001, the motion detection device 3004, and the scanning device 4006 can estimate the shape of the body suit according to the motion of the body of the person wearing the body suit. In FIGS. 57A and 57B, the electroconductive yarns 2021 are not shown, however, the electroconductive yarns 2021 are disposed on the second base member 9 to be connected to each curvature sensor 2003.

Similar to the description of the first base member 8, it is possible to measure the three-dimensional deformation of the second base member 9 by combining the curvature information of each curvature sensor 2003 disposed in the second base member 9.

In the case in which the first base member 8 and the second base member 9 are formed in enough narrow shapes, such base members may be used to form the sheet 2002 instead of the electroconductive yarns 2021.

The shape estimation device 2001 according to the fifth embodiment of the present invention, the motion detection device 3004 according to the sixth embodiment, and the scanning device 4006 according to the seventh embodiment have the functions of the shape estimation units 2012, 3042, 4062, respectively. With regard to these shape estimation units 2012, 3042, 4062, the processing of the shape estimation is the same. Also, these shape estimation units 2012, 3042, 4062 are operated according to the same principle as that of the contour estimation unit 202 according to the first embodiment described above, the description of the shape estimation processing in detail will be omitted.

The shape estimation device 2001 according to the fifth embodiment of the present invention, the motion detection device 3004 according to the sixth embodiment, and the scanning device 4006 according to the seventh embodiment have computer systems inside. The processing procedures described above are recorded in the computer-readable recording medium as a program, and the processing described above is performed when the program is read by the computer and executed by the computer. Here, the computer-readable recording medium is a magnetic disk, a magneto-optical disc, a compact disc read-only memory (CD-ROM), a semiconductor memory, or the like. In addition, the computer program may be distributed to the computer through a communication line, and the computer receiving the distributed program may execute the program. The program may be used for implementing part of the functions. Also, the program may be combined with the program which has been already recorded in the computer system for implementing the functions, that is, the program may be the differential file (differential program).

While some embodiments of the present invention have been described above, these embodiments are examples of the invention and are not intended to limit the scope of the invention. These embodiments may be performed in various other forms and various omissions, substitutions, and changes can be made without departing from the subject matter of the present invention. These embodiments and modifications are also considered to be included in the scope and subject matter of the present invention and these are also included in the invention disclosed in the appended claims and its equivalent scope.

The invention claimed is:

1. A measurement device comprising:
   a measurement belt to which a plurality of electrode pads arranged in a row and a plurality of strain gauges arranged in parallel to the plurality of electrode pads are integrally adhered and configured to be used after being wrapped around a measurement target portion of a living body; and
   a processor configured to:
   acquire an image of the measurement target portion of the living body while applying a current to the plurality of electrode pads and acquiring a voltage signal generated between the electrode pads; and
   estimate a contour shape of the measurement target portion of the living body and a size of the contour shape on the basis of curvature data acquired via the plurality of strain gauges,
   wherein the processor is further configured to:
   set coordinate positions of a first reference point and a second reference point as predetermined initial coordinate values, the coordinate positions of the first reference point indicating a position of a strain gauge among the plurality of strain gauges configured to be arranged in the row at a first half side of the measurement target portion of the living body and the coordinate positions of the second reference point indicating a position of a virtual strain gauge that is disposed between adjacent strain gauges among the plurality of strain gauges arranged in the row at a second half side opposite to the first half side of the measurement target portion of the living body;
   calculate relative coordinate values indicating coordinate positions of subordinate points according to the curvature data, the coordinate positions of the subordinate points indicating positions of one or more strain gauges with respect to the coordinate positions of adjacent first reference point and adjacent second reference point, and the one or more strain gauges being disposed between the strain gauges indicated by the adjacent first reference point and adjacent second reference point;
   change coordinate positions of the first reference point and the second reference point from the predetermined initial coordinate values such that a sum of errors of coordinate positions between a first subordinate point and a second subordinate point among the coordinate positions is minimized, the first subordinate point being the subordinate point whose coordinate position is determined from the relative coordinate value with respect to the coordinate position of the first reference point, the second subordinate point being the subordinate point whose coordinate position is determined from the relative coordinate value with respect to the coordinate position of the second reference point, and the first and second subordinate points indicating the position of the same strain gauge;

determine the coordinate positions of two subordinate points indicating positions of strain gauges disposed adjacently at both sides of each strain gauge indicated by each reference point as the coordinate position of a center point between the first subordinate point and the second subordinate point after the coordinate positions of the first reference point and the second reference point are changed; and estimate a contour shape based on the relative positional relation of the positions of the first and second reference and subordinate points using a predetermined function curve.

2. The measurement device according to claim 1, wherein the processor is configured to enlarge or reduce the specified contour shape such that a perimeter of the estimated contour shape matches a separately measured perimeter of the measurement target portion of the living body after the contour shape is determined.

3. The measurement device according to claim 1, wherein the processor is configured to regard the virtual strain gauge as being arranged on the symmetric axis of the measurement target portion of the living body to determine a relative positional relationship for the plurality of strain gauges, when no strain gauge is arranged at a position arranged at the opposite side of the strain gauge whose coordinate position is determined by the first reference point on the true symmetric axis of measurement target portion of the living body on the measurement belt wrapped around the measurement target portion of the living body.

4. The measurement device according to claim 1,
wherein the processor is configured to set a plurality of supplementary points for determining a curve connecting a position of one strain gauge and a position of another strain gauge adjacent to the one strain gauge when the contour shape is determined, and wherein a distance from an origin of the plurality of supplementary points is determined by a predetermine function at an angle formed by the supplementary points, the origin, and the position of the one strain gauge.

5. The measurement device according to claim 1, further comprising:

a perimeter measurement electrode pad arranged in parallel to the plurality of electrode pads and adhered to the measurement belt, wherein the processor is further configured to measure a perimeter of the measurement target portion of the living body on the basis of a voltage signal acquired via the perimeter measurement electrode pad.

6. A measurement device comprising:
a measurement belt having a plurality of first electrodes arranged on a longitudinal direction of the measurement belt, a second electrode, and a plurality of curvature sensors arranged on a longitudinal direction of the measurement belt, the measurement belt being configured to be wrapped around a measurement target portion of a living body; and a processor configured to:
detect predetermined physical effect applied to the measurement belt;

determine whether one of the plurality of first electrodes has an impedance with respect to the second electrode that is equal to or lower than a predetermined impedance value; and estimate a contour shape of the measurement target portion of the living body and a size of the contour shape on the basis of curvature data acquired via the plurality of curvature sensors, when the predetermined physical effect is detected and one of the plurality of first electrodes has an impedance with respect to the second electrode that is equal to or lower than the predetermined impedance value, wherein the processor is further configured to:
set coordinate positions of a plurality of reference points as predetermined initial coordinate values, each of the coordinate positions of the plurality of reference points indicating a position of one curvature sensor among the plurality of curvature sensors arranged in a row;

calculate relative coordinate values indicating coordinate positions of subordinate points according to the curvature data, the coordinate positions of the subordinate points indicating positions of one or more curvature sensors with respect to the coordinate positions of adjacent reference points of the plurality of reference points, and the one or more curvature sensors being disposed between the curvature sensors indicated by the adjacent reference points of the plurality of reference points, change coordinate positions of a first reference point and a second reference point different from the first reference point among the plurality of reference points from the predetermined initial coordinate values such that a sum of errors of coordinate positions between a first subordinate point and a second subordinate point among the coordinate positions is minimized, the first subordinate point being the subordinate point whose coordinate position is determined from the relative coordinate value with respect to the coordinate position of the first reference point, the second subordinate point being the subordinate point whose coordinate position is determined from the relative coordinate value with respect to the coordinate position of the second reference point, and the first and second subordinate points indicating the position of the same curvature sensor, determine the coordinate positions of two subordinate points indicating positions of curvature sensors disposed adjacently at both sides of each curvature sensor indicated by each reference point as the coordinate position of a center point between the first subordinate point and the second subordinate point after the coordinate positions of the first reference point and the second reference point are changed; and estimate a contour shape based on the relative positional relation of the positions of the reference and subordinate points using a predetermined function curve.

7. The measurement device according to claim 6, wherein the processor is configured to detect a movement of the belt.

8. The measurement device according to claim 6, wherein the processor is configured to detect a pressure force applied on a predetermined part of the belt.

9. The measurement device according to claim 6, wherein the process is further configured to measure a perimeter of the measurement target portion of the living body according to the impedance between the first electrode among the plurality of first electrodes and the second electrode.

10. The measurement device according to claim 9, wherein the processor is further configured to measure the perimeter of the measurement target portion of the living body, when the predetermined physical effect is detected and one of the plurality of first electrodes has an impedance with respect to the second electrode that is equal to or lower than the predetermined impedance value.

11. The measurement device according to claim 9, wherein the processor is further configured to:
estimate a partial shape of part of the circumference of the measurement target portion of the living body according to the curvature data acquired by the plurality of curvature sensors;
determine the part of the circumference of the measurement target portion of the living body corresponding to the estimated partial shape according to the perimeter; and
estimate a contour shape of the whole circumference of the measurement target portion of the living body using the partial shape according to the determination result indicating the part of the circumference of the measurement target portion of the living body corresponding to the estimated partial shape and an assumption that the contour shape is axial symmetry.

12. The measurement device according to claim 6, wherein the measurement belt has a buckle having a needle and a plurality of holes through which the needle can be inserted,
wherein the plurality of first electrodes are disposed at positions around the plurality of holes respectively, and
wherein the second electrode is disposed on the needle.

13. The measurement device according to claim 6, further comprises:
a first shield disposed at a first side of the plurality of first electrodes with respect to the measurement belt on either of a front surface or a rear surface of the measurement belt; and
a second shield disposed at a second side of the second electrode opposite to the first side with respect to the measurement belt, and
wherein the first shield and the second shield are configured to restrict a flow of an electromagnetic wave.

14. The measurement device according to claim 13, further comprises a power source configured to apply AC voltages with a same phase to at least one of the plurality of first electrodes and the first shield, and apply AC voltage with a same phase to the second electrode and the second shield.

15. A measurement device comprising:
a sheet having a base member on which a plurality of curvature sensors are disposed, the plurality of curvature sensors being spaced from each other at a predetermined space, and the sheet being configured to be covered on a measurement target portion of a living body; and
a processor configured to:
acquire curvature information of the plurality of curvature sensors; and
estimate a shape of the base member according to the curvature information,
wherein the processor is further configured to:
set coordinate positions of a plurality of reference points as predetermined initial coordinate values, each of the coordinate positions of the plurality of reference points indicating a position of one curvature sensor among the plurality of curvature sensors arranged on the sheet;
calculate relative coordinate values indicating coordinate positions of subordinate points according to the curvature data, the coordinate positions of the subordinate points indicating positions of one or more curvature sensors with respect to the coordinate positions of adjacent reference points of the plurality of reference points, and the one or more curvature sensors being disposed between the curvature sensors indicated by the adjacent reference points of the plurality of reference points,
change coordinate positions of a first reference point and a second reference point different from the first reference point among the plurality of reference points from the predetermined initial coordinate values such that sum of errors of coordinate positions between a first subordinate point and a second subordinate point among the coordinate positions is minimized, the first subordinate point being the subordinate point whose coordinate position is determined from the relative coordinate value with respect to the coordinate position of the first reference point, the second subordinate point being the subordinate point whose coordinate position is determined from the relative coordinate value with respect to the coordinate position of the second reference point, and the first and second subordinate points indicating the position of the same curvature sensor,
determine the coordinate positions of two subordinate points indicating positions of curvature sensors disposed adjacently at both sides of each curvature sensor indicated by each reference point as the coordinate position of a center point between the first subordinate point and the second subordinate point after the coordinate positions of the first reference point and the second reference point are changed; and
estimate a contour shape based on the relative positional relation of the positions of the reference and subordinate points using a predetermined function curve.

16. The measurement device according to claim 15, wherein the processor is configured to estimate a shape of the measurement target portion of the living body covered by the sheet according to the estimated shape of the sheet.

17. The measurement device according to claim 15, wherein the processor is configured to:
estimate a shape of clothes manufactured by the sheet according to the curvature information of the plurality of curvature sensors; and
estimate a movement of the measurement target portion of the living body wearing the clothes according to the shape of the clothes.

18. The measurement device according to claim 15, wherein the sheet is formed by a plurality of electroconductive yarns.

19. The measurement device according to claim 18, wherein the plurality of electroconductive yarns are configured to be insulated from each other, and
wherein the plurality of curvature sensors are disposed at the intersection points of the plurality of electroconductive yarns respectively.

* * * * *